US010077296B2

(12) United States Patent
Arya et al.

(10) Patent No.: US 10,077,296 B2

(45) Date of Patent: Sep. 18, 2018

(54) METHODS AND COMPOSITIONS FOR THE TREATMENT AND PREVENTION OF CANCER

(75) Inventors: Bira Arya, Lutherville, MD (US); Dan Longo, Kensington, MD (US); Igor Espinoza-Delgardo, Clarksville, MD (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 393 days.

(21) Appl. No.: 13/587,515

(22) Filed: Aug. 16, 2012

(65) Prior Publication Data

US 2012/0328640 A1 Dec. 27, 2012

Related U.S. Application Data

(62) Division of application No. 11/899,165, filed on Sep. 3, 2007, now Pat. No. 8,258,278.

(60) Provisional application No. 60/841,927, filed on Sep. 1, 2006.

(51) Int. Cl.

| | |
|---|---|
| ***C07K 14/47*** | (2006.01) |
| ***A61K 39/00*** | (2006.01) |
| ***A61K 39/39*** | (2006.01) |

(52) U.S. Cl.

CPC ...... *C07K 14/4748* (2013.01); *A61K 39/0011* (2013.01); *A61K 39/39* (2013.01); *A61K 2039/55522* (2013.01); *C07K 2319/33* (2013.01); *C07K 2319/74* (2013.01)

(58) Field of Classification Search

None

See application file for complete search history.

(56) References Cited

U.S. PATENT DOCUMENTS

2008/0044484 A1 2/2008 Minev

FOREIGN PATENT DOCUMENTS

| | | | |
|---|---|---|---|
| CA | 2 597 840 | * | 3/2008 |
| WO | 2004/012681 | A2 | 2/2004 |
| WO | 2005/073384 | A2 | 8/2005 |

OTHER PUBLICATIONS

Biragyn et al. Tumor-Associated Embryonic Antigen-Expressing Vaccines that Target CCR6 Elicit Potent CD8+ T Cell-Mediated Protective and Therapeutic Antitumor Immunity 179(2): 1381-1388, Jul. 15, 2007.*

A. Biragyn, "Chemoattractant-based vaccines which modulate APCs", National Institutes of Health, Oct. 1, 2005.

* cited by examiner

*Primary Examiner* — Alana Harris Dent

(74) *Attorney, Agent, or Firm* — Locke Lord LLP; Nicholas J. DiCeglie, Jr.

(57) ABSTRACT

The instant invention provides compositions for the treatment of cancer. Specifically, the invention provides polypeptides and nucleic acid molecules comprising tumor-associated embryonic antigens, e.g., OFA-iLRP, and chemoattractant ligands, e.g., a proinflammatory chemokine such as MIP3α/CCL20 or β-defensin mDF2β. The invention further provides cancer vaccines and methods for treating subjects having, or at risk of developing, cancer.

5 Claims, 43 Drawing Sheets

Specification includes a Sequence Listing.

| | | | | | | | | | | | | | | | | | | | | | | |
|---|---|---|---|---|---|---|---|---|---|---|---|---|---|---|---|---|---|---|---|---|---|---|
| T | + | + | + | + | + | + | + | + | + | + | + | + | + | + | + | + | + | + | + | - | - | - |
| E | + | + | + | + | + | + | + | + | + | + | + | + | + | + | + | + | + | + | + | + | + | + |
| MC | - | 0.1 | 0.1 | 0.1 | - | - | - | - | - | - | - | - | - | - | - | - | - | - | - | - | - | - |
| MC | - | - | - | - | 0.1 | 0.1 | 0.1 | - | - | - | - | - | - | - | - | - | - | - | - | - | - | - |
| | - | - | - | - | - | - | - | 0.1 | 0.1 | 0.1 | - | - | - | - | - | - | - | - | - | - | - | - |
| | - | - | - | - | - | - | - | - | - | - | 0.1 | 0.1 | 0.1 | - | - | - | - | - | - | - | - | - |
| | - | - | - | - | - | - | - | - | - | - | - | - | - | 1 | 1 | 1 | - | - | - | - | - | - |
| A20 | - | - | - | - | - | - | - | - | - | - | - | - | - | - | - | - | 1 | 1 | 1 | - | - | - |
| PTX | - | - | + | - | - | + | - | - | + | - | - | + | - | - | + | - | - | + | - | - | - | - |
| | - | - | - | + | - | - | + | - | - | + | - | - | + | - | - | + | - | - | + | - | - | - |
| | - | - | - | - | - | - | - | - | - | - | - | - | - | - | - | - | - | - | - | + | - | - |
| | - | - | - | - | - | - | - | - | - | - | - | - | - | - | - | - | - | - | - | - | + | - |
| A20 | - | - | - | - | - | - | - | - | - | - | - | - | - | - | - | - | - | - | - | - | - | + |

| T | + | + | + | + | + | + | + | + | + | + |
|---|---|---|---|---|---|---|---|---|---|---|
| E | + | + | + | + | + | + | + | + | + | + |
| mMIP3 hgp 100 | - | + | + | + | + | + | + | + | + | + |
| Laupeptin | - | - | + | - | - | - | - | - | - | - |
| Brefeldin A | - | - | - | + | - | - | - | - | - | - |
| Lactacystin | - | - | - | - | 50 | 10 | 1 | - | - | - |
| Chloroquine | - | - | - | - | - | - | - | 50 | 10 | 1 |

Survival %
Day
100
90
80
70
60
50
40
30
20
10
0
25
30
35
40
45
50
55
60
65
70
75
80
pmDF2βsFv20
pmDF3βsFv20
pmMIP3αsFv20
pMCP3sFv20
pmDF2βsFv38
PBS
p<0.0003
p<0.002

FIG. 14.1

DNA sequence of IPlead-mDF2β-(m)OFA (SEQ ID NO:1)

ATGAACCCAAGTGCTGCCGTCATTTTCTGCCTCATCCTGCTGGGTCTGAGTGGGACT
CAAGGGATCCTCGAcATGGAACT
TGACCACTGCCACACCAATGGAGGGTACTGTGTCAGAGCCATTTGTCCTCCTTCTGC
CAGGCGTCCTGGGAGCTGTTTCC
CAGAGAACAACCCCTGTTGCAAGTACATGAAAGATCTTGAATTCAACGACGCTCAG
GCGCCGAAGAGTCTCGACGGAGCC
CTTGACATCCTGCAGATGAAGGAGGAGGATGTCCTCAAATTCCTTGCTGCGGGAACC
CACTTAGGTGGCACCAACCTTGA
CTTTCAGATGGAGCAGTACATCTACAAAAGGAAAAGTGACGGTATCTACATCATAA
ACCTGAAGAGGACCTGGGAGAAGC
TGTTGCTCGCAGCTCGAGCTATTGTTGCCATCGAGAATCCTGCTGACGTCAGCGTCA
TCTCCTCCAGGAACACTGGCCAG
CGAGCTGTGCTGAAGTTTGCTGCTGCCACAGGAGCCACTCCGATCGCTGGCCGCTTC
ACACCTGGGACCTTCACTAACCA
GATCCAAGCAGCCTTCAGGGAGGCACGGNTTCTAGTGGTGACCGATCCCAGGGCTG
ACCATCAGCCACTCACAGAGGCCT
CTTATGTCAACCTGCCCACCATTGCTCTGTGTAACACAGATTCTCCCCTGCGCTATGT
GGACATTGCCATCCCATGCAAC
AACAAGGGAGCTCACTCAgTGGGtcTGATGTGGTGGATGCTGGcCAGGGAAGTAcTCC
GCATGCGAGGTACTATCTCCCG
TGAGCACCCCTGGGAGGtCATGCCTGATCtTTACTTCTACAGAGACCCagAgGAgATTG
AGAAGGAgGAGCAGGCTGCTg
cTgAgAAgGcTGTGACCaAgGAGGAATTCCagGGtGAATGGACCGCaCCaGCTCCTgaGTTc
aCTGCTGcTCAgCCTGAG
GtGGCCgACTGGTCTgaGGGtGtGCAGGTtCCcTcTGTGCCCATCCAGCAGTTCCCCACGG
AAGACTGGAGTGCACAGCC
AGCCACTGAGGATTGGTCAGCAGCTCCCACAGCGCAGGCCACTGAGTGGGTTGGAG
CCACCACTGAGTGGTCCTAA

Protein sequence of IPlead-mDF2β-(m)OFA (SEQ ID NO:2)

MNPSAAVIFCLILLGLSGTQGILDMELDHCHTNGGYCVRAICPPSARRPGSCFPENNPCC
KYMKDLEFNDAQAPKSLDGA
LDILQMKEEDVLKFLAAGTHLGGTNLDFQMEQYIYKRKSDGIYIINLKRTWEKLLLAAR
AIVAIENPADVSVISSRNTGQ
RAVLKFAAATGATPIAGRFTPGTFTNQIQAAFREARXLVVTDPRADHQPLTEASYVNLP
TIALCNTDSPLRYVDIAIPCN
NKGAHSVGLMWWMLAREVLRMRGTISREHPWEVMPDLYFYRDPEEIEKEEQAAAEKA
VTKEEFQGEWTAPAPEFTAAQPE
VADWSEGVQVPSVPIQQFPTEDWSAQPATEDWSAAPTAQATEWVGATTEWS.

FIG. 14.2

DNA sequence of IPlead-mMIP3α-(m)OFA(SEQ ID NO:3)

ATGAACCCAAGTGCTGCCGTCATTTTCTGCCTCATCCTGCTGGGTCTGAGTGGGACT
CAAGGGATCCTCGACATGGCAAGCAACTACGACTGTTGCCTCTCGTACATACAGAC
GCCTCTTCCTTCCAGAGCTATTGTGGGTTTCACAAGACAGATGGCCGATGAAGCTTG
TGACATTAATGCTATCATCTTTCACACGAAGAAAAGAAAATCTGTGTGCGCTGATCC
AAAGCAGAACTGGGTGAAAAGGGCTGTGAACCTCCTCAGCCTAAGAGTCAAGAAGA
TGGAATTCAACGACGCTCAGGCGCCGAAGAGTCTCGACGGAGCCCTTGACGTCCTG
CAGATGAAGGAGGAGGATGTCCTCAAATTCCTTGCTGCGGGAACCCACTTAGGTGG
CACCAACCTTGACTTTCAGATGGAGCAGTACATCTACAAAAGGAAAAGTGACGGTA
TCTACATCATAAACCTGAAGAGGACCTGGGAGAAGCTGTTGCTCGCAGCTCGAGCT
ATTGTTGCCATCGAGAATCCTGCTGACGTCAGCGTCATCTCCTCCAGGAACACTGGC
CAGCGAGCTGTGCTGAAGTTTGCTGCTGCCACAGGAGCCACTCCGATcgctggccgCTTC
ACACCTGGGACCTTCACTAACCAGATCCAAGCAGCCTTCAGGGAGGCACGGNTTCT
AGTGGTGACCGATCCCAGGGCTGACCATCAGCCACTCACAGAGGCCTCTTATGTCAA
CCTGCCCACCATTGCTCTGTGTAACACAGATTCTCCCCTGCGCTATGTGGACATTGCC
ATCCCATGCAACAACAAGGGAGCTCACTCAgTGGGtcTGATGTGGTGGATGCTGGcCA
GGGAAGTAcTCCGCATGCGAGGTACTATCTCCCGTGAGCACCCCTGGGAGGtCATGC
CTGATCtTTACTTCTACAGAGACCCagAgGAgATTGAGAAGGAgGAGCAGGCTGCTgcT
gAgAAgGcTGTGACCaAgGAGGAATTCCagGGtGAATGGACCGCaCCaGCTCCTgaGTTca
CTGCTGcTCAgCCTGAGGtGGCCgACTGGTCTgaGGGtGtGCAGGTtCCcTcTGTGCCCATC
CAGCAGTTCCCCACGGAAGACTGGAGTGCACAGCCAGCCACTGAGGATTGGTCAGC
AGCTCCCACAGCGCAGGCCACTGAGTGGGTTGGAGCCACCACTGAGTGGTCCTAA

Protein sequence of IPlead-mMIP3α-(m)OFA (SEQ ID NO:4)

MNPSAAVIFCLILLGLSGTQGILDMASNYDCCLSYIQTPLPSRAIVGFTRQMADEACDIN
AIIFHTKKRKSVCADPKQNWVKRAVNLLSLRVKKMEFNDAQAPKSLDGALDVLQMKE
EDVLKFLAAGTHLGGTNLDFQMEQYIYKRKSDGIYIINLKRTWEKLLLAARAIVAIENPA
DVSVISSRNTGQRAVLKFAAATGATPIAGRFTPGTFTNQIQAAFREARXLVVTDPRADH
QPLTEASYVNLPTIALCNTDSPLRYVDIAIPCNNKGAHSVGLMWWMLAREVLRMRGTIS
REHPWEVMPDLYFYRDPEEIEKEEQAAAEKAVTKEEFQGEWTAPAPEFTAAQPEVADW
SEGVQVPSVPIQQFPTEDWSAQPATEDWSAAPTAQATEWVGATTEWS

FIG. 14.3

DNA sequence of IPlead-(m)EP2-(m)OFA (SEQ ID NO:5)

ATGAACCCAAGTGCTGCCGTCATTTTCTGCCTCATCCTGCTGGGTCTGAGTGGGACT
CAAGGGATCTATTACCAAATTGT
CAACTGCAAGAAAAGTGAAGGACAATGTCAAGAATACTGTAATTTCATGGAAACAC
AAGTGGGCTACTGTTCAAAAAAGA
AAGAACCCTGCTGCTTACATCCGTTCGAATTCAACGACGCTCAGGCGCCGAAGAGTC
TCGACGGAGCCCTTGACGTCCTG
CAGATGAAGGAGGAGGATGTCCTCAAATTCCTTGCTGCGGGAACCCACTTAGGTGG
CACCAACCTTGACTTTCAGATGGA
GCAGTACATCTACAAAAGGAAAAGTGACGGTATCTACATCATAAACCTGAAGAGGA
CCTGGGAGAAGCTGTTGCTCGCAG
CTCGAGCTATTGTTGCCATCGAGAATCCTGCTGACGTCAGCGTCATCTCCTCCAGGA
ACACTGGCCAGCGAGCTGTGCTG
AAGTTTGCTGCTGCCACAGGAGCCACTCCGATCGCTGGCCGCTTCACACCTGGGACC
TTCACTAACCAGATCCAAGCAGC
CTTCAGGGAGCCACGGCTTCTAGTGGTGACCGATCCCAGGGCTGACCATCAGCCACT
CACAGAGGCCTCTTATGTCAACC
TGCCCACCATTGCTCTGTGTAACACAGATTCTCCCCTGCGCTATGTGGACATTGCCAT
CCCATGCAACAACAAGGGAGCT
CACTCAGTGGGTCTGATGTGGTGGATGCTGGCCAGGGAAGTACTCCGCATGCGAGG
TACTATCTCCCGTGAGCACCCCTG
GGAGGTCATGCCTGATCTTTACTTCTACAGAGACCCAGAGGAGATTGAGAAGGAGG
AGCAGGCTGCTGCTGAGAAGGCTG
TGACCAAGGAGGAATTCCAGGGTGAATGGACCGCACCAGCTCCTGAGTTCACTGCT
GCTCAGCCTGAGGTGGCCGACTGG
TCTGAGGGTGTGCAGGTTCCCTCTGTGCCCATCCAGCAGTTCCCCACGGAAGACTGG
AGTGCACAGCCAGCCACTGAGGA
TTGGTCAGCAGCTCCCACAGCGCAGGCCACTGAGTGGGTTGGAGCCACCACTGAGT
GGTCCTAA

Protein sequence of IPlead-(m)EP2-(m)OFA (SEQ ID NO:6)

MNPSAAVIFCLILLGLSGTQGIYYQIVNCKKSEGQCQEYCNFMETQVGYCSKKKEPCCL
HPFEFNDAQAPKSLDGALDVL
QMKEEDVLKFLAAGTHLGGTNLDFQMEQYIYKRKSDGIYIINLKRTWEKLLLAARAIVA
IENPADVSVISSRNTGQRAVL
KFAAATGATPIAGRFTPGTFTNQIQAAFREPRLLVVTDPRADHQPLTEASYVNLPTIALC
NTDSPLRYVDIAIPCNNKGA
HSVGLMWWMLAREVLRMRGTISREHPWEVMPDLYFYRDPEEIEKEEQAAAEKAVTKE
EFQGEWTAPAPEFTAAQPEVADW
SEGVQVPSVPIQQFPTEDWSAQPATEDWSAAPTAQATEWVGATTEWS

FIG. 14.4

Construct IPlead-(m)OFA-Hsp70 (SEQ ID NO:7)

This construct contains signal sequence from murine IP-10, followed with murine OFA linked with mature form of micobacterial Hsp70 (COO-end fragment starting from residue 359).

ATGAACCCAAGTGCTGCCGTCATTTTCTGCCTCATCCTGCTGGGTCTGAGTGGGACT
CAAGGGATCCTCGAcGGAGCCCTTGACGTCCTGCAGATGAaGGAGGAGGATGTCCTC
AAATTCCTTGCTGcGGGAaCCCACTTAGGTGGCACCAACCTTGAcTTTCAGATGGAGC
AGTACATCTACAAAAGGAAAAGTGACGGTATCTACATCATAAACCTGAAGAGGACc
TGGGAGAAGCTGTTGCTCGCAGCTCGAGCTATTGTTGCCATCGAGAATCCTGCTGAC
GTCAGCGTCATCTCCTCCAGGAACACTGGCCAGCGAGCTGTGCTGAAGTTTGCTGCT
GCCACAGGAGCCACTCCGATCGCTGGCCGCTTCACACCTGGGACCTTCACTAACCAG
ATCCAAGCAGCCTTCAGGGAGCCACGGCTTCTAGTGGTGACCGATCCCAGGGCTGA
CCATCAGCCACTCACAGAGGCCTCTTATGTCAACCTGCCCACCATTGCTCTGTGTAA
CACAGATTCTCCCCTGCGCTATGTGGACATTGCCATCCCATGCAACAACAAGGGAGC
TCACTCAGTGGGTCTGATGTGGTGGATGCTGGCCAGGGAAGTACTCCGCATGCGAG
GTACTATCTCCCGTGAGCACCCCTGGGAGGTCATGCCTGATCTTTACTTCTACAGAG
ACCCAGAGGAGATTGAGAAGGAGGAGCAGGCTGCTGCTGAGAAGGCTGTGACCAA
GGAGGAATTCCAGGGTGAATGGACCGCACCAGCTCCTGAGTTCACTGCTGCTCAGC
CTGAGGTGGCCGACTGGTCTGAGGGTGTGCAGGTTCCCTCTGTGCCCATCCAGCAGT
TCCCCACGGAAGACTGGAGTGCACAGCCAGCCACTGAGGATTGGTCAGCAGCTCCC
ACAGCGCAGGCCACTGAGTGGGTTGGAGCCACCACTGAGTGGTCCGGATCCGAG
GTGAAAGACGTTCTGCTGCTTGATGTTACCCCGCTGAGCCTGGGTATCGAGACCAAG
GGCGGGGTGATGACCAGGCTCATCGAGCGCAACACCACGATCCCCACCAAGCGGTC
GGAGACTTTCACCACCGCCGACGACAACCAACCGTCGGTGCAGATCCAGGTCTATC
AGGGGGAGCGTGAGATCGCCGCGCACAACAAGTTGCTCGGGTCCTTCGAGCTGACC
GGCATCCCGCCGGCGCCGCGGGGGATTCCGCAGATCGAGGTCACTTTCGACATCGA
CGCCAACGGCATTGTGCACGTCACCGCCAAGGACAAGGGCACCGGCAAGGAGAAC
ACGATCCGAATCCAGGAAGGCTCGGGCCTGTCCAAGGAAGACATTGACCGCATGAT
CAAGGACGCCGAAGCGCACGCCGAGGAGGATCGCAAGCGTCGCGAGGAGGCCGAT
GTTCGTAATCAAGCCGAGACATTGGTCTACCAGACGGAGAAGTTCGTCAAAGAACA
GCGTGAGGCCGAGGGTGGTTCGAAGGTACCTGAAGACACGCTGAACAAGGTTGATG
CCGCGGTGGCGGAAGCGAAGGCGGCACTTGGCGGATCGGATATTTCGGCCATCAAG
TCGGCGATGGAGACGCTGGGCCAGGAGTCGCAGGCTCTGGGGCAAGCGATCTACGA
AGCAGCTCAGGCTGCGTCACAGGCCACTGGCGCTGCCCACCCCGGCGGC
GAGCCGGGCGGTGCCCACCCCGGCTCGGCTGATAGATCTTAA

FIG. 14.5

Protein sequence of IPlead(m)OFA-Hsp70(SEQ ID NO:8)

MNPSAAVIFCLILLGLSGTQGILDGALDVLQMKEEDVLKFLAAGTHLGGTNLDFQMEQY
IYKRKSDGIYIINLKRTWEKLLLAARAIVAIENPADVSVISSRNTGQRAVLKFAAATGATP
IAGRFTPGTFTNQIQAAFREPRLLVVTDPRADHQPLTEASYVNLPTIALCNTDSPLRYVDI
AIPCNNKGAHSVGLMWWMLAREVLRMRGTISREHPWEVMPDLYFYRDPEEIEKEEQA
AAEKAVTKEEFQGEWTAPAPEFTAAQPEVADWSEGVQVPSVPIQQFPTEDWSAQPATE
DWSAAPTAQATEWVGATTEWSGSEVKDVLLLDVTPLSLGIETKGGVMTRLIERNTTIPT
KRSETFTTADDNQPSVQIQVYQGEREIAAHNKLLGSFELTGIPPAPRGIPQIEVTFDIDAN
GIVHVTAKDKGTGKENTIRIQEGSGLSKEDIDRMIKDAEAHAEEDRKRREEADVRNQAE
TLVYQTEKFVKEQREAEGGSKVPEDTLNKVDAAVAEAKAALGGSDISAIKSAMETLGQ
ESQALGQAIYEAAQAASQATGAAHPGGEPGGAHPGSADRS

Construct IPlead-(m)EP2c-(m)OFA, (SEQ ID NO:9)

ATGAACCCAAGTGCTGCCGTCATTTTCTGCCTCATCCTGCTGGGTCTGAGTGGGACC
AAGGGATCTATTACCAAATTGTCAACTGCAAGAAAAGTGAAGGACAATGTCAAGAA
TACTGTAATTTCATGGAAACACAAGTGGGCTACTGTTCAAAAAAGAAAGAACCCTG
CTGCTTACATCCGTTCGAATTCAACGACGCTCAGGCGCCGAAGAGTCTCGACGGAGC
CCTTGACGTCCTGCAGATGAAGGAGGAGGATGTCCTCAAATTCCTTGCTGCGGGAAC
CCACTTAGGTGGCACCAACCTTGACTTTCAGATGGAGCAGTACATCTACAAAAGGA
AAAGTGACGGTATCTACATCATAAACCTGAAGAGGACCTGGGAGAAGCTGTTGCTC
GCAGCTCGAGCTATTGTTGCCATCGAGAATCCTGCTGACGTCAGCGTCATCTCCTCC
AGGAACACTGGCCAGCGAGCTGTGCTGAAGTTTGCTGCTGCCACAGGAGCCACTCC
GATCGCTGGCCGCTTCACACCTGGGACCTTCACTAACCAGATCCAAGCAGCCTTCAG
GGAGCCACGGCTTCTAGTGGTGACCGATCCCAGGGCTGACCATCAGCCACTCACAG
AGGCCTCTTATGTCAACCTGCCCACCATTGCTCTGTGTAACACAGATTCTCCCCTGCG
CTATGTGGACATTGCCATCCCATGCAACAACAAGGGAGCTCACTCAGTGGGTCTGAT
GTGGTGGATGCTGGCCAGGGAAGTACTCCGCATGCGAGGTACTATCTCCCGTGAGC
ACCCCTGGGAGGTCATGCCTGATCTTTACTTCTACAGAGACCCAGAGGAGATTGAGA
AGGAGGAGCAGGCTGCTGCTGAGAAGGCTGTGACCAAGGAGGAATTCCAGGGTGA
ATGGACCGCACCAGCTCCTGAGTTCACTGCTGCTCAGCCTGAGGTGGCCGACTGG
TCTGAGGGTGTGCAGGTTCCCTCTGTGCCCATCCAGCAGTTCCCCACGGAAGACTGG
AGTGCACAGCCAGCCACTGAGGATTGGTCAGCAGCTCCCACAGCGCAGGCCACTGA
GTGGGTTGGAGCCACCACTGAGTGGTCCTAA

FIG. 14.6

Construct hMIP3α-(m)OFA(SEQ ID NO:11)

ATGTGCTGTACCAAGAGTTTGCTCCTGGCTGCTTTGATGTCAGTGCTGCTACTCCACT
CTGCGGCGAATCAGAAGCAGCAAGCAACTTTGACTGCTGTCTTGGATACACAGACC
GTATTCTTCATCCTAAATTTATTGTGGGCTTCACACGGCAGCTGGCCAATGGAGGCT
GTGACATCAATGCTATCATCTTTCACACAAAGAAAAAGTTGTCTGTGTGCGCAAATC
CAAAACAGACTTGGGTGAAATATATTGTGCGTCTCCTCAGTAAAAAAGTCAAGAAC
ATGGAATTCAACGACGCTCAGGCGCCGAAGAGTCTCGACGGAGCCCTTGACGTCCT
GCAGATGAAGGAGGAGGATGTCCTCAAATTCCTTGCTGCGGGAACCCACTTAGGTG
GCACCAACCTTGACTTTCAGATGGAGCAGTACATCTACAAAAGGAAAAGTGACGGT
ATCTACATCATAAACCTGAAGAGGACCTGGGAGAAGCTGTTGCTCGCAGCTCGAGC
TATTGTTGCCATCGAGAATCCTGCTGACGTCAGCGTCATCTCCTCCAGGAACACTGG
CCAGCGAGCTGTGCTGAAGTTTGCTGCTGCCACAGGAGCCACTCCGATcgctggccgCTT
CACACCTGGGACCTTCACTAACCAGATCCAAGCAGCCTTCAGGGAGGCACGGNTTC
TAGTGGTGACCGATCCCAGGGCTGACCATCAGCCACTCACAGAGGCCTCTTATGTCA
ACCTGCCCACCATTGCTCTGTGTAACACAGATTCTCCCCTGCGCTATGTGGACATTG
CCATCCCATGCAACAACAAGGGAGCTCACTCAgTGGGtcTGATGTGGTGGATGCTGGc
CAGGGAAGTAcTCCGCATGCGAGGTACTATCTCCCGTGAGCACCCCTGGGAGGtCAT
GCCTGATCtTTACTTCTACAGAGACCCagAgGAgATTGAGAAGGAgGAGCAGGCTGCTg
cTgAgAAgGcTGTGACCaAgGAGGAATTCCagGGtGAATGGACCGCaCCaGCTCCTgaGTTc
aCTGCTGcTCAgCCTGAGGtGGCCgACTGGTCTgaGGGtGtGCAGGTtCCcTcTGTGCCCAT
CCAGCAGTTCCCCACGGAAGACTGGAGTGCACAGCCAGCCACTGAGGATTGGTCAG
CAGCTCCCACAGCGCAGGCCACTGAGTGGGTTGGAGCCACCACTGAGTGG
TCCTAA

Protein sequence of hMIP3α-(m)OFA(SEQ ID NO:12)

MCCTKSLLLAALMSVLLLHLCGESEAASNFDCCLGYTDRILHPKFIVGFTRQLANGGCDI
NAIIFHTKKKLSVCANPKQTWVKYIVRLLSKKVKNMEFNDAQAPKSLDGALDVLQMKE
EDVLKFLAAGTHLGGTNLDFQMEQYIYKRKSDGIYIINLKRTWEKLLLAARAIVAIENPA
DVSVISSRNTGQRAVLKFAAATGATPIAGRFTPGTFTNQIQAAFREARXLVVTDPRADH
QPLTEASYVNLPTIALCNTDSPLRYVDIAIPCNNKGAHSVGLMWWMLAREVLRMRGTIS
REHPWEVMPDLYFYRDPEEIEKEEQAAAEKAVTKEEFQGEWTAPAPEFTAAQPEVADW
SEGVQVPSVPIQQFPTEDWSAQPATEDWSAAPTAQATEWVGATTEWS

FIG. 14.7

Construct IPlead-(h)DF1β-(m)OFA, (SEQ ID NO:13)

ATGAACCCAAGTGCTGCCGTCATTTTCTGCCTCATCCTGCTGGGTCTGAGTGGGACT
CAAGGGATCCTCGACATGGATCA
TTACAATTGCGTCAGCAGTGGAGGGCAATGTCTCTATTCTGCCTGCCCGATCTTTACC
AAAATTCAAGGCACCTGTTACA
GAGGGAAGGCCAAGTGCTGCAAGGAATTCAACGACGCTCAGGCGCCGAAGAGTCTC
GACGGAGCCCTTGACGTCCTGCAG
ATGAAGGAGGAGGATGTCCTCAAATTCCTTGCTGCGGGAACCCACTTAGGTGGCAC
CAACCTTGACTTTCAGATGGAGCA
GTACATCTACAAAAGGAAAAGTGACGGTATCTACATCATAAACCTGAAGAGGACCT
GGGAGAAGCTGTTGCTCGCAGCTC
GAGCTATTGTTGCCATCGAGAATCCTGCTGACGTCAGCGTCATCTCCTCCAGGAACA
CTGGCCAGCGAGCTGTGCTGAAG
TTTGCTGCTGCCACAGGAGCCACTCCGATcgctggccgCTTCACACCTGGGACCTTCACT
AACCAGATCCAAGCAGCCTT
CAGGGAGGCACGGNTTCTAGTGGTGACCGATCCCAGGGCTGACCATCAGCCACTCA
CAGAGGCCTCTTATGTCAACCTGC
CCACCATTGCTCTGTGTAACACAGATTCTCCCCTGCGCTATGTGGACATTGCCATCCC
ATGCAACAACAAGGGAGCTCAC
TCAgTGGGtcTGATGTGGTGGATGCTGGcCAGGGAAGTAcTCCGCATGCGAGGTACTA
TCTCCCGTGAGCACCCCTGGGA
GGtCATGCCTGATCtTTACTTCTACAGAGACCCagAgGAgATTGAGAAGGAgGAGCAGG
CTGCTgcTgAgAAgGcTGTGA
CCaAgGAGGAATTCCagGGtGAATGGACCGCaCCaGCTCCTgaGTTcaCTGCTGcTCAgCC
TGAGGtGGCCgACTGGTCT
gaGGGtGtGCAGGTtCCcTcTGTGCCCATCCAGCAGTTCCCCACGGAAGACTGGAGTGC
ACAGCCAGCCACTGAGGATTG
GTCAGCAGCTCCCACAGCGCAGGCCACTGAGTGGGTTGGAGCCACCACTGAGTGGT
CCTAA

Protein sequence of IPlead(h)DF1β-(m)OFA(SEQ ID NO:14)

MNPSAAVIFCLILLGLSGTQGILDMDHYNCVSSGGQCLYSACPIFTKIQGTCYRGKAKCC
KEFNDAQAPKSLDGALDVLQ
MKEEDVLKFLAAGTHLGGTNLDFQMEQYIYKRKSDGIYIINLKRTWEKLLLAARAIVAI
ENPADVSVISSRNTGQRAVLK
FAAATGATPIAGRFTPGTFTNQIQAAFREARXLVVTDPRADHQPLTEASYVNLPTIALCN
TDSPLRYVDIAIPCNNKGAH
SVGLMWWMLAREVLRMRGTISREHPWEVMPDLYFYRDPEEIEKEEQAAAEKAVTKEE
FQGEWTAPAPEFTAAQPEVADWS
EGVQVPSVPIQQFPTEDWSAQPATEDWSAAPTAQATEWVGATTEWS

FIG. 14.8

Construct IPlead-(h)DF1β-(h)OFA: (SEQ ID NO:15)

ATGAACCCAAGTGCTGCCGTCATTTTCTGCCTCATCCTGCTGGGTCTGAGTGGGACC
AAGGGATCCTCGACATGGATCATTACAATTGCGTCAGCAGTGGAGGGCAATGTCTC
ATTCTGCCTGCCCGATCTTTACCAAAATTCAAGGCACCTGTTACAGAGGGAAGGCCA
AGTGCTGCAAGGAATTCAACGACGCTCAGGCGCCGAAGAGTCTCGACtccggagcccttgat
gtcctgcaaatgaaggaggaggatgtccttaagttccttgcagcaggaacccacttaggtggcaccaatcttgacttccagatgga
acagtacatctataaaaggaaaagtgatggcatctatatcataaatctcaagaggacctgggagaagcttctgctggcag
ctcgtgcaattgttgccattgaaaaccctgctgatgtcagtgttatatcctccaggaatactggccagagggctgtgctg
aagtttgctgctgccactggagccactccaattgctggccgcttcactcctggaaccttcactaaccagatccaggcagc
cttccgggagccacggcttcttgtggttactgaccccagggctgaccaccagcctctcacggaggcatcttatgttaacc
tacctaccattgcgctgtgtaacacagattctcctctgcgctatgtggacattgccatcccatgcaacaacaagggagct
cactcagtgggtttaatgtggtggatgctggctcgggaagttctgcgcatgcgtggcaccatttcccgtgaacacccatg
ggaggtcatgcctgatctgtacttctacagagatcctgaagagattgaaaaagaagagcaggctgctgctgagaaggcag
tgaccaaggaggaatttcagggtgaatggactgctcccgctcctgagttcactgctactcagcctgaggttgcagactgg
tctgaaggtgtacaggtgccctctgtgcctattcagcaattccctactgaagactggagcgctcagcctgccacggaaga
ctggtctgcagctcccactgctcaggccactgaatgggtaggagcaaccactgactggtctTAA

Translated IPlead-(h)DF1β-(h)OFA (SEQ ID NO:16)
MNPSAAVIFCLILLGLSGTQGILDMDHYNCVSSGGQCLYSACPIFTKIQGTCYRGKAKCC
KEFNDAQAPKSLDSGALDVLQMKEEDVLKFLAAGTHLGGTNLDFQMEQYIYKRKSDGI
YIINLKRTWEKLLLAARAIVAIENPADVSVISSRNTGQRAVLKFAAATGATPIAGRFTPGT
FTNQIQAAFREPRLLVVTDPRADHQPLTEASYVNLPTIALCNTDSPLRYVDIAIPCNNKG
AHSVGLMWWMLAREVLRMRGTISREHPWEVMPDLYFYRDPEEIEKEEQAAAEKAVTK
EEFQGEWTAPAPEFTATQPEVADWSEGVQVPSVPIQQFPTEDWSAQPATEDWSAAPTA
QATEWVGATTDWS.

FIG. 14.9

Construct hMIP3α-(h)OFA(SEQ ID NO:17)
This construct contains human MIP3α/CCL20 with its own signal sequence, followed by a short spacer sequence and human OFA.

ATGTGCTGTACCAAGAGTTTGCTCCTGGCTGCTTTGATGTCAGTGCTGCTACTCCACC
TCTGCGGCGAATCAGAAGCAGCAAGCAACTTTGACTGCTGTCTTGGATACACAGACC
GTATTCTTCATCCTAAATTTATTGTGGGCTTCACACGGCAGCTGGCCAATGGAGGCT
GTGACATCAATGCTATCATCTTTCACACAAAGAAAAAGTTGTCTGTGTGCGCAAATC
CAAAACAGACTTGGGTGAAATATATTGTGCGTCTCCTCAGTAAAAAAGTCAAGAAC
ATGGAATTCAACGACGCTCAGGCGCCGAAGAGTCT
CGACtccggagcccttgatgtcctgcaaatgaaggaggaggatgtccttaagttccttgcagcaggaacccacttaggtg
gcaccaatcttgacttccagatggaacagtacatctataaaaggaaaagtgatggcatctatatcataaatctcaagagg
acctgggagaagcttctgctggcagctcgtgcaattgttgccattgaaaaccctgctgatgtcagtgttatatcctccag
gaatactggccagagggctgtgctgaagtttgctgctgccactggagccactccaattgctggccgcttcactcctggaa
ccttcactaaccagatccaggcagccttccgggagccacggcttcttgtggttactgaccccagggctgaccaccagcct
ctcacggaggcatcttatgttaacctacctaccattgcgctgtgtaacacagattctcctctgcgctatgtggacattgc
catcccatgcaacaacaagggagctcactcagtgggtttaatgtggtggatgctggctcgggaagttctgcgcatgcgtg
gcaccatttcccgtgaacacccatgggaggtcatgcctgatctgtacttctacagagatcctgaagagattgaaaaagaa
gagcaggctgctgctgagaaggcagtgaccaaggaggaatttcagggtgaatggactgctcccgctcctgagttcactgc
tactcagcctgaggttgcagactggtctgaaggtgtacaggtgccctctgtgcctattcagcaattccctactgaagactggagcgctcagcc
tgccacggaagactggtctgcagctcccactgctcaggccactgaatgggtaggagcaaccactgactggtctTAA

Translated hMIP3α-(h)OFA(SEQ ID NO:18)

MCCTKSLLLAALMSVLLLHLCGESEAASNFDCCLGYTDRILHPKFIVGFTRQLANGGCDI
NAIIFHTKKKLSVCANPKQTWVKYIVRLLSKKVKNMEFNDAQAPKSLDSGALDVLQMK
EEDVLKFLAAGTHLGGTNLDFQMEQYIYKRKSDGIYIINLKRTWEKLLLAARAIVAIENP
ADVSVISSRNTGQRAVLKFAAATGATPIAGRFTPGTFTNQIQAAFREPRLLVVTDPRADH
QPLTEASYVNLPTIALCNTDSPLRYVDIAIPCNNKGAHSVGLMWWMLAREVLRMRGTIS
REHPWEVMPDLYFYRDPEEIEKEEQAAAEKAVTKEEFQGEWTAPAPEFTATQPEVADW
SEGVQVPSVPIQQFPTEDWSAQPATEDWSAAPTAQATEWVGATTDWS.

FIG. 14.10

DNA sequence of mDF2β-(m)OFA (SEQ ID NO:19)
ATGGAACTTGACCACTGCCACACCAATGGAGGGTACTGTGTCAGAGCCATTTGTCCT
CCTTCTGCCAGGCGTCCTGGGAGCTGTTTCCCAGAGAACAACCCCTGTTGCAAGTAC
ATGAAAGATCTTGAATTCAACGACGCTCAGGCGCCGAAGAGTCTCGACGGAGCCCT
TGACGTCCTGCAGATGAAGGAGGAGGATGTCCTCAAATTCCTTGCTGCGGGAACCC
ACTTAGGTGGCACCAACCTTGACTTTCAGATGGAGCAGTACATCTACAAAAGGAAA
AGTGACGGTATCTACATCATAAACCTGAAGAGGACCTGGGAGAAGCTGTTGCTCGC
AGCTCGAGCTATTGTTGCCATCGAGAATCCTGCTGACGTCAGCGTCATCTCCTCCAG
GAACACTGGCCAGCGAGCTGTGCTGAAGTTTGCTGCTGCCACAGGAGCCACTCCGA
TCGCTGGCCGCTTCACACCTGGGACCTTCACTAACCAGATCCAAGCAGCCTTCAGGG
AGCCACGGCTTCTAGTGGTGACCGATCCCAGGGCTGACCATCAGCCACTCACAGAG
GCCTCTTATGTCAACCTGCCCACCATTGCTCTGTGTNACACAGATTCTCCCCTGCGCT
ATGTGGACATTGCCATCCCATGCAACAACAAGGGAGCTCACTCAGTGGGTCTGATGT
GGTGGATGCTGGCCAGGGAAGTACTCCGCATGCGAGGTACTATCTCCCGTGAGCAC
CCCTGGGAGGTCATGCCTGATCTTTACTTCTACAGAGACCCAGAGGAGATTGAGAAG
GAGGAGCAGGCTGCTGCTGAGAAGGCTGTGACCAAGGAGGAATTCCAGGGTGAATG
GACCGCACCAGCTCCTGAGTTCACTGCTGCTCAGCCTGAGGTGGCCGACTGGTCTGA
GGGTGTGCAGGTTCCCTCTGTGCCCATCCAGCAGTTCCCCACGGAAGACTGGAGT
GCACAGCCAGCCACTGAGGATTGGTCAGCAGCTCCCACAGCGCAGGCCACTGAGTG
GGTTGGAGCCACCACTGAGTGGTCCTAA mDF2β-(m)OFA encoded protein sequence (SEQ ID NO:20)

MELDHCHTNGGYCVRAICPPSARRPGSCFPENNPCCKYMKDLEFNDAQAPKSLDGALD
VLQMKEEDVLKFLAAGTHLGGTNLDFQMEQYIYKRKSDGIYIINLKRTWEKLLLAARAI
VAIENPADVSVISSRNTGQRAVLKFAAATGATPIAGRFTPGTFTNQIQAAFREPRLLVVT
DPRADHQPLTEASYVNLPTIALCXTDSPLRYVDIAIPCNNKGAHSVGLMWWMLAREVL
RMRGTISREHPWEVMPDLYFYRDPEEIEKEEQAAAEKAVTKEEFQGEWTAPAPEFTAAQ
PEVADWSEGVQVPSVPIQQFPTEDWS

FIG. 14.11

DNA sequence of mMIP3α-(m)OFA (no myc his tags): (SEQ ID NO:21)

ATGGCAAGCAACTACGACTGTTGCCTCTCGTACATACAGACGCCTCTTCCTTCCAGA
GCTATTGTGGGTTTCACAAGACAGATGGCCGATGAAGCTTGTGACATTAATGCTATC
ATCTTTCACACGAAGAAAAGAAAATCTGTGTGCGCTGATCCAAAGCAGAACTGGGT
GAAAAGGGCTGTGAACCTCCTCAGCCTAAGAGTCAAGAAGATGGAATTCAACGACG
CTCAGGCGCCGAAGAGTCTCGACGGAGCCCTTGACGTCCTGCAGATGANGGAGGAG
GATGTCCTCAAATTCCTTGCTGcGGGAaCCCACTTAGGTGGCACCAACCTTGATTTTC
AGATGGAGCAGTACATCTACAAAAGGAAAAGTGACGGTATCTACATCATAAACCTG
AAGAGGACNTGGGAGAAGCTGTTGCTCGCAGCTCGAGCTATTGTTGCCATCGAGAA
TCCTGCTGACGTCAGCGTCATCTCCTCCAGGAACACTGGCCAGCGAGCTGTGCTGAA
GTTTGCTGCTGCCACAGGAGCCACTCCGATCGCTGGCCGCTTCACACCTGGGACCTT
CACTAACCAGATCCAAGCAGCCTTCAGGGAGCCACGGCTTCTAGTGGTGACCGATC
CAGGGCTGACCATCAGCCACTCACAGAGGCCTCTTATGTCAACCTGCCCACCATTGC
TCTGTGTAACACAGATTCTCCCCTGCGCTATGTGGACATTGCCATCCCATGCAACAA
CAAGGGAGCTCACTCAGTGGGTCTGATGTGGTGGATGCTGGCCAGGGAAGTACTCC
GCATGCGAGGTACTATCTCCCGTGAGCACCCCTGGGAGGTCATGCCTGATCTTTACT
TCTACAGAGACCCAGAGGAGATTGAGAAGGAGGAGCAGGCTGCTGCTGAGAAGGCT
GTGACCAAGGAGGAATTCCAGGGTGAATGGACCGCACCAGCTCCTGAGTTCACTGC
TGCTCAGCCTGAGGTGGCCGACTGGTCTGAGGGTGTGCAGGTTCCCTCTGTGCCCAT
CCAGCAGTTCCCCACGGAAGACTGGAGTGCACAGCCAGCCACTGAGGATTGGTCAG
CAGCTCCCACAGCGCAGGCCACTGAGTGGGTTGGAGCCACCACTGAGTGGTCCTAA

FIG. 14.12

Protein sequence of mMIP3α-(m)OFA (SEQ ID NO:22)

MASNYDCCLSYIQTPLPSRAIVGFTRQMADEACDINAIIFHTKKRKSVCADPKQNWVKR
AVNLLSLRVKKMEFNDAQAPKSLDGALDVLQMXEEDVLKFLAAGTHLGGTNLDFQME
QYIYKRKSDGIYIINLKRTWEKLLLAARAIVAIENPADVSVISSRNTGQRAVLKFAAATG
ATPIAGRFTPGTFTNQIQAAFREPRLLVVTDPRADHQPLTEASYVNLPTIALCNTDSPLRY
VDIAIPCNNKGAHSVGLMWWMLAREVLRMRGTISREHPWEVMPDLYFYRDPEEIEKEE
QAAAEKAVTKEEFQGEWTAPAPEFTAAQPEVADWSEGVQVPSVPIQQFPTEDWSAQPA
TEDWSAAPTAQATEWVGATTEWS

DNA sequence of hMIP3α-(m)OFA (SEQ ID NO:23)

ATGGCAAGCAACTTTGACTGCTGTCTTGGATACACAGACCGTATTCTTCATCCTAAA
TTTATTGTGGGCTTCACACGGCAGCTGGCCAATGGAGGCTGTGACATCAATGCTATC
ATCTTTCACACAAAGAAAAAGTTGTCTGTGTGCGCAAATCCAAAACAGACTTGGGTG
AAATATATTGTGCGTCTCCTCAGTAAAAAAGTCAAGAACATGGAATTCAACGACGCT
CAGGCGCCGAAGAGTCTCGACGGAGCCCTTGACGTCCTGCAGATGAAGGAGGAGGA
TGTCCTCAAATTCCTTGCTGCGGGAACCCACTTAGGTGGCACCAACCTTGACTTTCA
GATGGAGCAGTACATCTACAAAAGGAAAAGTGACGGTATCTACATCATAAACCTGA
AGAGGACCTGGGAGAAGCTGTTGCTCGCAGCTCGAGCTATTGTTGCCATCGAGAATC
CTGCTGACGTCAGCGTCATCTCCTCCAGGAACACTGGCCAGCGAGCTGTGCTGAAGT
TTGCTGCTGCCACAGGAGCCACTCCGATcgctggccgCTTCACACCTGGGACCTTCACTA
ACCAGATCCAAGCAGCCTTCAGGGAGGCACGGNTTCTAGTGGTGACCGATCCCAGG
GCTGACCATCAGCCACTCACAGAGGCCTCTTATGTCAACCTGCCCACCATTGCTCTG
TGTAACACAGATTCTCCCCTGCGCTATGTGGACATTGCCATCCCATGCAACAACAAG
GGAGCTCACTCAgTGGGtcTGATGTGGTGGATGCTGGcCAGGGAAGTAcTCCGCATGC
GAGGTACTATCTCCCGTGAGCACCCCTGGGAGGtCATGCCTGATCtTTACTTCTACAG
AGACCCagAgGAgATTGAGAAGGAgGAGCAGGCTGCTgcTgAgAAgGcTGTGACCaAgGA
GGAATTCCagGGtGAATGGACCGCaCCaGCTCCTgaGTTcaCTGCTGcTCAgCCTGAGGtG
GCCgACTGGTCTgaGGGtGtGCAGGTtCCcTcTGTGCCCATCCAGCAGTTCCCCACGGAA
GACTGGAGTGCACAGCCAGCCACTGAGGATTGGTCAGCAGCTCCCACAGCGCAGGC
ACTGAGTGGGTTGGAGCCACCACTGAGTGGTCCTAA

FIG. 14.13

Protein sequence of hMIP3α-(m)OFA (SEQ ID NO:24)

MASNFDCCLGYTDRILHPKFIVGFTRQLANGGCDINAIIFHTKKKLSVCANPKQTWVKYI
VRLLSKKVKNMEFNDAQAPK
SLDGALDVLQMKEEDVLKFLAAGTHLGGTNLDFQMEQYIYKRKSDGIYIINLKRTWEK
LLLAARAIVAIENPADVSVISS
RNTGQRAVLKFAAATGATPIAGRFTPGTFTNQIQAAFREARXLVVTDPRADHQPLTEAS
YVNLPTIALCNTDSPLRYVDI
AIPCNNKGAHSVGLMWWMLAREVLRMRGTISREHPWEVMPDLYFYRDPEEIEKEEQA
AAEKAVTKEEFQGEWTAPAPEFT
AAQPEVADWSEGVQVPSVPIQQFPTEDWSAQPATEDWSAAPTAQATEWVGATTEWS

FIG. 14.14

DNA sequence of mOFA-Hsp70, murine OFA-iLRP fused with mycobacterial Hsp70 COO-fragment that activates DCs (SEQ ID NO:25)

ATGCTCGAcGGAGCCCTTGACGTCCTGCAGATGAaGGAGGAGGATGTCCTCAAATTC
CTTGCTGcGGGAaCCCACTTAGGTGGCACCAACCTTGAcTTTCAGATGGAGCAGTACA
TCTACAAAAGGAAAAGTGACGGTATCTACATCATAAACCTGAAGAGGACcTGGGAG
AAGCTGTTGCTCGCAGCTCGAGCTATTGTTGCCATCGAGAATCCTGCTGACGTCAGC
GTCATCTCCTCCAGGAACACTGGCCAGCGAGCTGTGCTGAAGTTTGCTGCTGCCACA
GGAGCCACTCCGATCGCTGGCCGCTTCACACCTGGGACCTTCACTAACCAGATCCAA
GCAGCCTTCAGGGAGCCACGGCTTCTAGTGGTGACCGATCCCAGGGCTGACCATCA
GCCACTCACAGAGGCCTCTTATGTCAACCTGCCCACCATTGCTCTGTGTAACACAGA
TTCTCCCCTGCGCTATGTGGACATTGCCATCCCATGCAACAACAAGGGAGCTCACTC
AGTGGGTCTGATGTGGTGGATGCTGGCCAGGGAAGTACTCCGCATGCGAGGTACTA
TCTCCCGTGAGCACCCCTGGGAGGTCATGCCTGATCTTTACTTCTACAGAGACCCAG
AGGAGATTGAGAAGGAGGAGCAGGCTGCTGCTGAGAAGGCTGTGACCAAGGAGGA
ATTCCAGGGTGAATGGACCGCACCAGCTCCTGAGTTCACTGCTGCTCAGCCTGAGGT
GGCCGACTGGTCTGAGGGTGTGCAGGTTCCCTCTGTGCCCATCCAGCAGTTCCCCAC
GGAAGACTGGAGTGCACAGCCAGCCACTGAGGATTGGTCAGCAGCTCCCACAGCGC
AGGCCACTGAGTGGGTTGGAGCCACCACTGAGTGGTCCGGATCCGAGGTGAAAGAC
GTTCTGCTGCTTGATGTTACCCCGCTGAGCCTGGGTATCGAGACCAAGGGCGGGGTG
ATGACCAGGCTCATCGAGCGCAACACCACGATCCCCACCAAGCGGTCGGAGACTTT
CACCACCGCCGACGACAACCAACCGTCGGTGCAGATCCAGGTCTATCAGGGGGAGC
GTGAGATCGCCGCGCACAACAAGTTGCTCGGGTCCTTCGAGCTGACCGGCATCCCGC
CGGCGCCGCGGGGGATTCCGCAGATCGAGGTCACTTTCGACATCGACGCCAACGGC
ATTGTGCACGTCACCGCCAAGGACAAGGGCACCGGCAAGGAGAACACGATCCGAAT
CCAGGAAGGCTCGGGCCTGTCCAAGGAAGACATTGACCGCATGATCAAGGACGCCG
AAGCGCACGCCGAGGAGGATCGCAAGCGTCGCGAGGAGGCCGATGTTCGTAATCAA
GCCGAGACATTGGTCTACCAGACGGAGAAGTTCGTCAAAGAACAGCGTGAGGCCGA
GGGTGGTTCGAAGGTACCTGAAGACACGCTGAACAAGGTTGATGCCGCGGTGGCGG
AAGCGAAGGCGGCACTTGGCGGATCGGATATTTCGGCCATCAAGTCGGCGATGGAG
ACGCTGGGCCAGGAGTCGCAGGCTCTGGGGCAAGCGATCTACGAAGCAGCTCAGGC
TGCGTCACAGGCCACTGGCGCTGCCCACCCCGGCGGCGAGCCGGGCGGTGCCCACC
CCGGCTCGGCTGATAGATCTTAA

FIG. 14.15

Protein sequence of mOFA-Hsp70 (SEQ ID NO:26)
MLDGALDVLQMKEEDVLKFLAAGTHLGGTNLDFQMEQYIYKRKSDGIYIINLKRTWEK
LLLAARAIVAIENPADVSVISSRNTGQRAVLKFAAATGATPIAGRFTPGTFTNQIQAAFRE
PRLLVVTDPRADHQPLTEASYVNLPTIALCNTDSPLRYVDIAIPCNNKGAHSVGLMWW
MLAREVLRMRGTISREHPWEVMPDLYFYRDPEEIEKEEQAAAEKAVTKEEFQGEWTAP
APEFTAAQPEVADWSEGVQVPSVPIQQFPTEDWSAQPATEDWSAAPTAQATEWVGATT
EWSGSEVKDVLLLDVTPLSLGIETKGGVMTRLIERNTTIPTKRSETFTTADDNQPSVQIQV
YQGEREIAAHNKLLGSFELTGIPPAPRGIPQIEVTFDIDANGIVHVTAKDKGTGKENTIRIQ
EGSGLSKEDIDRMIKDAEAHAEEDRKRREEADVRNQAETLVYQTEKFVKEQREAEGGS
KVPEDTLNKVDAAVAEAKAALGGSDISAIKSAMETLGQESQALGQAIYEAAQAASQAT
GAAHPGGEPGGAHPGSADRS

FIG. 14.16

DNA sequence of hOFA-Hsp70 (human OFA-iLRP-Hsp70), human OFA-iLRP fused with mycobacterial Hsp70 COO fragment (SEQ ID NO:27)

ATGCTCGACtccggagcccttgatgtcctgcaaatgaaggaggaggatgtccttaagttccttgcagcaggaacccactt
aggtggcaccaatcttgacttccagatggaacagtacatctataaaaggaaaagtgatggcatctatatcataaatctca
agaggacctgggagaagcttctgctggcagctcgtgcaattgttgccattgaaaaccctgctgatgtcagtgttatatcc
tccaggaatactggccagagggctgtgctgaagtttgctgctgccactggagccactccaattgctggccgcttcactcc
tggaaccttcactaaccagatccaggcagccttccgggagccacggcttcttgtggttactgaccccagggctgaccacc
agcctctcacggaggcatcttatgttaacctacctaccattgcgctgtgtaacacagattctcctctgcgctatgtggac
attgccatcccatgcaacaacaagggagctcactcagtgggtttaatgtggtggatgctggctcgggaagttctgcgcat
gcgtggcaccatttcccgtgaacacccatgggaggtcatgcctgatctgtacttctacagagatcctgaagagattgaa
aagaagagcaggctgctgctgagaaggcagtgaccaaggaggaatttcagggtgaatggactgctcccgctcctgagttc
actgctactcagcctgaggttgcagactggtctgaaggtgtacaggtgccctctgtgcctattcagcaattccctactga
agactggagcgctcagcctgccacggaagactggtctgcagctcccactgctcaggccactgaatgggtaggagcaaccactgactggtc
tGGATCCGAGGTGAAAGACGTTCTGCTGCTTGATGTTACCCCGCTGAGCCTGGGTATC
GAGACCAAGGGC
GGGGTGATGACCAGGCTCATCGAGCGCAACACCACGATCCCCACCAAGCGGTCGGA
GACTTTCACCACCGCCGACGACAA
CCAACCGTCGGTGCAGATCCAGGTCTATCAGGGGGAGCGTGAGATCGCCGCGCACA
ACAAGTTGCTCGGGTCCTTCGAGC
TGACCGGCATCCCGCCGGCGCCGCGGGGGATTCCGCAGATCGAGGTCACTTTCGAC
ATCGACGCCAACGGCATTGTGCAC
GTCACCGCCAAGGACAAGGGCACCGGCAAGGAGAACACGATCCGAATCCAGGAAG
GCTCGGGCCTGTCCAAGGAAGACAT
TGACCGCATGATCAAGGACGCCGAAGCGCACGCCGAGGAGGATCGCAAGCGTCGCG
AGGAGGCCGATGTTCGTAATCAAG
CCGAGACATTGGTCTACCAGACGGAGAAGTTCGTCAAAGAACAGCGTGAGGCCGAG
GGTGGTTCGAAGGTACCTGAAGAC
ACGCTGAACAAGGTTGATGCCGCGGTGGCGGAAGCGAAGGCGGCACTTGGCGGATC
GGATATTTCGGCCATCAAGTCGGC
GATGGAGACGCTGGGCCAGGAGTCGCAGGCTCTGGGGCAAGCGATCTACGAAGCAG
CTCAGGCTGCGTCACAGGCCACTG
GCGCTGCCCACCCCGGCGGCGAGCCGGGCGGTGCCCACCCCGGCTCGGCTGATAGA
TCTTAA

FIG. 14.17

Protein sequence of hOFA-Hsp70 (human OFA-iLRP-Hsp70): (SEQ ID NO:28)
MLDSGALDVLQMKEEDVLKFLAAGTHLGGTNLDFQMEQYIYKRKSDGIYIINLKRTWE
KLLLAARAIVAIENPADVSVIS
SRNTGQRAVLKFAAATGATPIAGRFTPGTFTNQIQAAFREPRLLVVTDPRADHQPLTEAS
YVNLPTIALCNTDSPLRYVD
IAIPCNNKGAHSVGLMWWMLAREVLRMRGTISREHPWEVMPDLYFYRDPEEIEKEEQA
AAEKAVTKEEFQGEWTAPAPEF
TATQPEVADWSEGVQVPSVPIQQFPTEDWSAQPATEDWSAAPTAQATEWVGATTDWS
GSEVKDVLLLDVTPLSLGIETKG
GVMTRLIERNTTIPTKRSETFTTADDNQPSVQIQVYQGEREIAAHNKLLGSFELTGIPPAP
RGIPQIEVTFDIDANGIVH
VTAKDKGTGKENTIRIQEGSGLSKEDIDRMIKDAEAHAEEDRKRREEADVRNQAETLVY
QTEKFVKEQREAEGGSKVPED
TLNKVDAAVAEAKAALGGSDISAIKSAMETLGQESQALGQAIYEAAQAASQATGAAHP
GGEPGGAHPGSADRS

DNA sequence of hMIP3α-(h)OFA, human MIP3α/CCL20 fused with human OFA-iLRP:
(SEQ ID NO:29)

ATGGCAAGCAACTTTGACTGCTGTCTTGGATACACAGACCGTATTCTTCATCCTAAA
TTTATTGTGGGCTTCACACGGCA
GCTGGCCAATGGAGGCTGTGACATCAATGCTATCATCTTTCACACAAAGAAAAAGTT
GTCTGTGTGCGCAAATCCAAAAC
AGACTTGGGTGAAATATATTGTGCGTCTCCTCAGTAAAAAAGTCAAGAACATGGAA
TTCAACGACGCTCAGGCGCCGAAG
AGTCTCGACtccggagcccttgatgtcctgcaaatgaaggaggaggatgtccttaagttccttgcagcaggaacccacttaggtgg
caccaatcttgacttccagatggaacagtacatctataaaaggaaaagtgatggcatctatatcataaatctca
agaggacctgggagaagcttctgctggcagctcgtgcaattgttgccattgaaaaccctgctgatgtcagtgttatatcc
tccaggaatactggccagagggctgtgctgaagtttgctgctgccactggagccactccaattgctggccgcttcactcc
tggaaccttcactaaccagatccaggcagccttccgggagccacggcttcttgtggttactgaccccagggctgaccacc
agcctctcacggaggcatcttatgttaacctacctaccattgcgctgtgtaacacagattctcctctgcgctatgtggac
attgccatcccatgcaacaacaagggagctcactcagtgggtttaatgtggtggatgctggctcgggaagttctgcgcat
gcgtggcaccatttcccgtgaacacccatgggaggtcatgcctgatctgtacttctacagagatcctgaagagattgaaa
aagaagagcaggctgctgctgagaaggcagtgaccaaggaggaatttcagggtgaatggactgctcccgctcctgagttc
actgctactcagcctgaggttgcagactggtctgaaggtgtacaggtgccctctgtgcctattcagcaattccctactga
agactggagcgctcagcctgccacggaagactggtctgcagctcccactgctcaggccactgaatgggtaggagcaaccactgactggtc
tTAA

FIG. 14.18

Protein sequence of hMIP3α-(h)OFA, human MIP3α/CCL20 fused with human OFA-iLRP: (SEQ ID NO:30)
MASNFDCCLGYTDRILHPKFIVGFTRQLANGGCDINAIIFHTKKKLSVCANPKQTWVKYI
VRLLSKKVKNMEFNDAQAPK
SLDSGALDVLQMKEEDVLKFLAAGTHLGGTNLDFQMEQYIYKRKSDGIYIINLKRTWEK
LLLAARAIVAIENPADVSVIS
SRNTGQRAVLKFAAATGATPIAGRFTPGTFTNQIQAAFREPRLLVVTDPRADHQPLTEAS
YVNLPTIALCNTDSPLRYVD
IAIPCNNKGAHSVGLMWWMLAREVLRMRGTISREHPWEVMPDLYFYRDPEEIEKEEQA
AAEKAVTKEEFQGEWTAPAPEF
TATQPEVADWSEGVQVPSVPIQQFPTEDWSAQPATEDWSAAPTAQATEWVGATTDWS.

SEQUENCE LISTING

```
<160> NUMBER OF SEQ ID NOS: 31

<210> SEQ ID NO 1
<211> LENGTH: 1116
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (589)
<223> OTHER INFORMATION: a, c, g, t, unknown or other

<400> SEQUENCE: 1

atgaacccaa gtgctgccgt cattttctgc ctcatcctgc tgggtctgag tgggactcaa      60

gggatcctcg acatggaact tgaccactgc cacaccaatg gagggtactg tgtcagagcc     120

atttgtcctc cttctgccag gcgtcctggg agctgtttcc cagagaacaa cccctgttgc     180

aagtacatga aagatcttga attcaacgac gctcaggcgc cgaagagtct cgacggagcc     240

cttgacatcc tgcagatgaa ggaggaggat gtcctcaaat tccttgctgc gggaacccac     300

ttaggtggca ccaaccttga ctttcagatg gagcagtaca tctacaaaag gaaaagtgac     360
```

```
ggtatctaca tcataaacct gaagaggacc tgggagaagc tgttgctcgc agctcgagct    420

attgttgcca tcgagaatcc tgctgacgtc agcgtcatct cctccaggaa cactggccag    480

cgagctgtgc tgaagtttgc tgctgccaca ggagccactc cgatcgctgg ccgcttcaca    540

cctgggacct tcactaacca gatccaagca gccttcaggg aggcacggnt tctagtggtg    600

accgatccca gggctgacca tcagccactc acagaggcct cttatgtcaa cctgccccacc   660

attgctctgt gtaacacaga ttctcccctg cgctatgtgg acattgccat cccatgcaac    720

aacaagggag ctcactcagt gggtctgatg tggtggatgc tggccaggga agtactccgc    780

atgcgaggta ctatctcccg tgagcacccc tgggaggtca tgcctgatct ttacttctac    840

agagacccag aggagattga gaaggaggag caggctgctg ctgagaaggc tgtgaccaag    900

gaggaattcc agggtgaatg gaccgcacca gctcctgagt tcactgctgc tcagcctgag    960

gtggccgact ggtctgaggg tgtgcaggtt ccctctgtgc ccatccagca gttccccacg   1020

gaagactgga gtgcacagcc agccactgag gattggtcag cagctcccac agcgcaggcc   1080

actgagtggg ttggagccac cactgagtgg tcctaa                             1116
```

<210> SEQ ID NO 2
<211> LENGTH: 371
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (197)
<223> OTHER INFORMATION: variable amino acid

<400> SEQUENCE: 2

```
Met Asn Pro Ser Ala Ala Val Ile Phe Cys Leu Ile Leu Leu Gly Leu
  1               5                  10                  15

Ser Gly Thr Gln Gly Ile Leu Asp Met Glu Leu Asp His Cys His Thr
             20                  25                  30

Asn Gly Gly Tyr Cys Val Arg Ala Ile Cys Pro Pro Ser Ala Arg Arg
         35                  40                  45

Pro Gly Ser Cys Phe Pro Glu Asn Asn Pro Cys Cys Lys Tyr Met Lys
     50                  55                  60

Asp Leu Glu Phe Asn Asp Ala Gln Ala Pro Lys Ser Leu Asp Gly Ala
 65                  70                  75                  80

Leu Asp Ile Leu Gln Met Lys Glu Glu Asp Val Leu Lys Phe Leu Ala
                 85                  90                  95

Ala Gly Thr His Leu Gly Gly Thr Asn Leu Asp Phe Gln Met Glu Gln
            100                 105                 110

Tyr Ile Tyr Lys Arg Lys Ser Asp Gly Ile Tyr Ile Ile Asn Leu Lys
        115                 120                 125

Arg Thr Trp Glu Lys Leu Leu Leu Ala Ala Arg Ala Ile Val Ala Ile
    130                 135                 140

Glu Asn Pro Ala Asp Val Ser Val Ile Ser Ser Arg Asn Thr Gly Gln
145                 150                 155                 160

Arg Ala Val Leu Lys Phe Ala Ala Ala Thr Gly Ala Thr Pro Ile Ala
                165                 170                 175

Gly Arg Phe Thr Pro Gly Thr Phe Thr Asn Gln Ile Gln Ala Ala Phe
            180                 185                 190

Arg Glu Ala Arg Xaa Leu Val Val Thr Asp Pro Arg Ala Asp His Gln
        195                 200                 205
```

```
Pro Leu Thr Glu Ala Ser Tyr Val Asn Leu Pro Thr Ile Ala Leu Cys
    210                 215                 220

Asn Thr Asp Ser Pro Leu Arg Tyr Val Asp Ile Ala Ile Pro Cys Asn
225                 230                 235                 240

Asn Lys Gly Ala His Ser Val Gly Leu Met Trp Trp Met Leu Ala Arg
                245                 250                 255

Glu Val Leu Arg Met Arg Gly Thr Ile Ser Arg Glu His Pro Trp Glu
            260                 265                 270

Val Met Pro Asp Leu Tyr Phe Tyr Arg Asp Pro Glu Glu Ile Glu Lys
        275                 280                 285

Glu Glu Gln Ala Ala Ala Glu Lys Ala Val Thr Lys Glu Glu Phe Gln
    290                 295                 300

Gly Glu Trp Thr Ala Pro Ala Pro Glu Phe Thr Ala Ala Gln Pro Glu
305                 310                 315                 320

Val Ala Asp Trp Ser Glu Gly Val Gln Val Pro Ser Val Pro Ile Gln
                325                 330                 335

Gln Phe Pro Thr Glu Asp Trp Ser Ala Gln Pro Ala Thr Glu Asp Trp
            340                 345                 350

Ser Ala Ala Pro Thr Ala Gln Ala Thr Glu Trp Val Gly Ala Thr Thr
        355                 360                 365

Glu Trp Ser
    370


<210> SEQ ID NO 3
<211> LENGTH: 1203
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (676)
<223> OTHER INFORMATION: a, c, g, t, unknown or other

<400> SEQUENCE: 3

atgaacccaa gtgctgccgt cattttctgc ctcatcctgc tgggtctgag tgggactcaa     60

gggatcctcg acatggcaag caactacgac tgttgcctct cgtacataca gacgcctctt    120

ccttccagag ctattgtggg tttcacaaga cagatggccg atgaagcttg tgacattaat    180

gctatcatct ttcacacgaa gaaaagaaaa tctgtgtgcg ctgatccaaa gcagaactgg    240

gtgaaaaggg ctgtgaacct cctcagccta agagtcaaga agatggaatt caacgacgct    300

caggcgccga agagtctcga cggagccctt gacgtcctgc agatgaagga ggaggatgtc    360

ctcaaattcc ttgctgcggg aacccactta ggtggcacca accttgactt tcagatggag    420

cagtacatct acaaaaggaa aagtgacggt atctacatca taaacctgaa gaggacctgg    480

gagaagctgt tgctcgcagc tcgagctatt gttgccatcg agaatcctgc tgacgtcagc    540

gtcatctcct ccaggaacac tggccagcga gctgtgctga agtttgctgc tgccacagga    600

gccactccga tcgctggccg cttcacacct gggaccttca ctaaccagat ccaagcagcc    660

ttcagggagg cacggnttct agtggtgacc gatcccaggg ctgaccatca gccactcaca    720

gaggcctctt atgtcaacct gcccaccatt gctctgtgta acacagattc tcccctgcgc    780

tatgtggaca ttgccatccc atgcaacaac aagggagctc actcagtggg tctgatgtgg    840

tggatgctgg ccagggaagt actccgcatg cgaggtacta tctcccgtga gcacccctgg    900
```

```
gaggtcatgc ctgatcttta cttctacaga gacccagagg agattgagaa ggaggagcag    960

gctgctgctg agaaggctgt gaccaaggag gaattccagg gtgaatggac cgcaccagct   1020

cctgagttca ctgctgctca gcctgaggtg gccgactggt ctgagggtgt gcaggttccc   1080

tctgtgccca tccagcagtt ccccacggaa gactggagtg cacagccagc cactgaggat   1140

tggtcagcag ctcccacagc gcaggccact gagtgggttg gagccaccac tgagtggtcc   1200

taa                                                                 1203


<210> SEQ ID NO 4
<211> LENGTH: 400
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (226)
<223> OTHER INFORMATION: variable amino acid

<400> SEQUENCE: 4

Met Asn Pro Ser Ala Ala Val Ile Phe Cys Leu Ile Leu Leu Gly Leu
  1               5                  10                  15

Ser Gly Thr Gln Gly Ile Leu Asp Met Ala Ser Asn Tyr Asp Cys Cys
             20                  25                  30

Leu Ser Tyr Ile Gln Thr Pro Leu Pro Ser Arg Ala Ile Val Gly Phe
         35                  40                  45

Thr Arg Gln Met Ala Asp Glu Ala Cys Asp Ile Asn Ala Ile Ile Phe
     50                  55                  60

His Thr Lys Lys Arg Lys Ser Val Cys Ala Asp Pro Lys Gln Asn Trp
 65                  70                  75                  80

Val Lys Arg Ala Val Asn Leu Leu Ser Leu Arg Val Lys Lys Met Glu
                 85                  90                  95

Phe Asn Asp Ala Gln Ala Pro Lys Ser Leu Asp Gly Ala Leu Asp Val
            100                 105                 110

Leu Gln Met Lys Glu Glu Asp Val Leu Lys Phe Leu Ala Ala Gly Thr
        115                 120                 125

His Leu Gly Gly Thr Asn Leu Asp Phe Gln Met Glu Gln Tyr Ile Tyr
    130                 135                 140

Lys Arg Lys Ser Asp Gly Ile Tyr Ile Ile Asn Leu Lys Arg Thr Trp
145                 150                 155                 160

Glu Lys Leu Leu Leu Ala Ala Arg Ala Ile Val Ala Ile Glu Asn Pro
                165                 170                 175

Ala Asp Val Ser Val Ile Ser Ser Arg Asn Thr Gly Gln Arg Ala Val
            180                 185                 190

Leu Lys Phe Ala Ala Ala Thr Gly Ala Thr Pro Ile Ala Gly Arg Phe
        195                 200                 205

Thr Pro Gly Thr Phe Thr Asn Gln Ile Gln Ala Ala Phe Arg Glu Ala
    210                 215                 220

Arg Xaa Leu Val Val Thr Asp Pro Arg Ala Asp His Gln Pro Leu Thr
225                 230                 235                 240

Glu Ala Ser Tyr Val Asn Leu Pro Thr Ile Ala Leu Cys Asn Thr Asp
                245                 250                 255

Ser Pro Leu Arg Tyr Val Asp Ile Ala Ile Pro Cys Asn Asn Lys Gly
            260                 265                 270

Ala His Ser Val Gly Leu Met Trp Trp Met Leu Ala Arg Glu Val Leu
```

```
        275                 280                 285

Arg Met Arg Gly Thr Ile Ser Arg Glu His Pro Trp Glu Val Met Pro
    290                 295                 300

Asp Leu Tyr Phe Tyr Arg Asp Pro Glu Glu Ile Glu Lys Glu Glu Gln
305                 310                 315                 320

Ala Ala Ala Glu Lys Ala Val Thr Lys Glu Glu Phe Gln Gly Glu Trp
                325                 330                 335

Thr Ala Pro Ala Pro Glu Phe Thr Ala Ala Gln Pro Glu Val Ala Asp
            340                 345                 350

Trp Ser Glu Gly Val Gln Val Pro Ser Val Pro Ile Gln Gln Phe Pro
        355                 360                 365

Thr Glu Asp Trp Ser Ala Gln Pro Ala Thr Glu Asp Trp Ser Ala Ala
    370                 375                 380

Pro Thr Ala Gln Ala Thr Glu Trp Val Gly Ala Thr Thr Glu Trp Ser
385                 390                 395                 400


<210> SEQ ID NO 5
<211> LENGTH: 1104
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5

atgaacccaa gtgctgccgt cattttctgc ctcatcctgc tgggtctgag tgggactcaa     60

gggatctatt accaaattgt caactgcaag aaaagtgaag gacaatgtca agaatactgt    120

aatttcatgg aaacacaagt gggctactgt tcaaaaaaga aagaaccctg ctgcttacat    180

ccgttcgaat tcaacgacgc tcaggcgccg aagagtctcg acggagccct tgacgtcctg    240

cagatgaagg aggaggatgt cctcaaattc cttgctgcgg gaacccactt aggtggcacc    300

aaccttgact ttcagatgga gcagtacatc tacaaaagga aaagtgacgg tatctacatc    360

ataaacctga agaggacctg ggagaagctg ttgctcgcag ctcgagctat tgttgccatc    420

gagaatcctg ctgacgtcag cgtcatctcc tccaggaaca ctggccagcg agctgtgctg    480

aagtttgctg ctgccacagg agccactccg atcgctggcc gcttcacacc tgggaccttc    540

actaaccaga tccaagcagc cttcagggag ccacggcttc tagtggtgac cgatcccagg    600

gctgaccatc agccactcac agaggcctct tatgtcaacc tgcccaccat tgctctgtgt    660

aacacagatt ctcccctgcg ctatgtggac attgccatcc catgcaacaa caagggagct    720

cactcagtgg gtctgatgtg gtggatgctg gccagggaag tactccgcat gcgaggtact    780

atctcccgtg agcacccctg ggaggtcatg cctgatcttt acttctacag agacccagag    840

gagattgaga aggaggagca ggctgctgct gagaaggctg tgaccaagga ggaattccag    900

ggtgaatgga ccgcaccagc tcctgagttc actgctgctc agcctgaggt ggccgactgg    960

tctgagggtg tgcaggttcc ctctgtgccc atccagcagt tccccacgga agactggagt   1020

gcacagccag ccactgagga ttggtcagca gctcccacag cgcaggccac tgagtgggtt   1080

ggagccacca ctgagtggtc ctaa                                           1104


<210> SEQ ID NO 6
<211> LENGTH: 367
<212> TYPE: PRT
<213> ORGANISM: Artificial Sequence
<220> FEATURE:
<223> OTHER INFORMATION: Description of Artificial Sequence: Synthetic
```

```
      construct

<400> SEQUENCE: 6

Met Asn Pro Ser Ala Ala Val Ile Phe Cys Leu Ile Leu Leu Gly Leu
  1               5                  10                  15

Ser Gly Thr Gln Gly Ile Tyr Tyr Gln Ile Val Asn Cys Lys Lys Ser
             20                  25                  30

Glu Gly Gln Cys Gln Glu Tyr Cys Asn Phe Met Glu Thr Gln Val Gly
         35                  40                  45

Tyr Cys Ser Lys Lys Lys Glu Pro Cys Cys Leu His Pro Phe Glu Phe
     50                  55                  60

Asn Asp Ala Gln Ala Pro Lys Ser Leu Asp Gly Ala Leu Asp Val Leu
 65                  70                  75                  80

Gln Met Lys Glu Glu Asp Val Leu Lys Phe Leu Ala Ala Gly Thr His
                 85                  90                  95

Leu Gly Gly Thr Asn Leu Asp Phe Gln Met Glu Gln Tyr Ile Tyr Lys
            100                 105                 110

Arg Lys Ser Asp Gly Ile Tyr Ile Ile Asn Leu Lys Arg Thr Trp Glu
        115                 120                 125

Lys Leu Leu Leu Ala Ala Arg Ala Ile Val Ala Ile Glu Asn Pro Ala
    130                 135                 140

Asp Val Ser Val Ile Ser Ser Arg Asn Thr Gly Gln Arg Ala Val Leu
145                 150                 155                 160

Lys Phe Ala Ala Ala Thr Gly Ala Thr Pro Ile Ala Gly Arg Phe Thr
                165                 170                 175

Pro Gly Thr Phe Thr Asn Gln Ile Gln Ala Ala Phe Arg Glu Pro Arg
            180                 185                 190

Leu Leu Val Val Thr Asp Pro Arg Ala Asp His Gln Pro Leu Thr Glu
        195                 200                 205

Ala Ser Tyr Val Asn Leu Pro Thr Ile Ala Leu Cys Asn Thr Asp Ser
    210                 215                 220

Pro Leu Arg Tyr Val Asp Ile Ala Ile Pro Cys Asn Asn Lys Gly Ala
225                 230                 235                 240

His Ser Val Gly Leu Met Trp Trp Met Leu Ala Arg Glu Val Leu Arg
                245                 250                 255

Met Arg Gly Thr Ile Ser Arg Glu His Pro Trp Glu Val Met Pro Asp
            260                 265                 270

Leu Tyr Phe Tyr Arg Asp Pro Glu Glu Ile Glu Lys Glu Glu Gln Ala
        275                 280                 285

Ala Ala Glu Lys Ala Val Thr Lys Glu Glu Phe Gln Gly Glu Trp Thr
    290                 295                 300

Ala Pro Ala Pro Glu Phe Thr Ala Ala Gln Pro Glu Val Ala Asp Trp
305                 310                 315                 320

Ser Glu Gly Val Gln Val Pro Ser Val Pro Ile Gln Gln Phe Pro Thr
                325                 330                 335

Glu Asp Trp Ser Ala Gln Pro Ala Thr Glu Asp Trp Ser Ala Ala Pro
            340                 345                 350

Thr Ala Gln Ala Thr Glu Trp Val Gly Ala Thr Thr Glu Trp Ser
        355                 360                 365


<210> SEQ ID NO 7
<211> LENGTH: 1722
<212> TYPE: DNA
<213> ORGANISM: Artificial Sequence
<220> FEATURE:
```

<223> OTHER INFORMATION: Description of Artificial Sequence: Synthetic construct

<400> SEQUENCE: 7

```
atgaacccaa gtgctgccgt cattttctgc ctcatcctgc tgggtctgag tgggactcaa     60
gggatcctcg acggagccct tgacgtcctg cagatgaagg aggaggatgt cctcaaattc    120
cttgctgcgg gaacccactt aggtggcacc aaccttgact ttcagatgga gcagtacatc    180
tacaaaagga aaagtgacgg tatctacatc ataaacctga agaggacctg ggagaagctg    240
ttgctcgcag ctcgagctat tgttgccatc gagaatcctg ctgacgtcag cgtcatctcc    300
tccaggaaca ctggccagcg agctgtgctg aagtttgctg ctgccacagg agccactccg    360
atcgctggcc gcttcacacc tgggaccttc actaaccaga tccaagcagc cttcagggag    420
ccacggcttc tagtggtgac cgatcccagg gctgaccatc agccactcac agaggcctct    480
tatgtcaacc tgcccaccat tgctctgtgt aacacagatt ctcccctgcg ctatgtggac    540
attgccatcc catgcaacaa caagggagct cactcagtgg gtctgatgtg gtggatgctg    600
gccagggaag tactccgcat gcgaggtact atctcccgtg agcacccctg ggaggtcatg    660
cctgatcttt acttctacag agacccagag gagattgaga aggaggagca ggctgctgct    720
gagaaggctg tgaccaagga ggaattccag ggtgaatgga ccgcaccagc tcctgagttc    780
actgctgctc agcctgaggt ggccgactgg tctgagggtg tgcaggttcc ctctgtgccc    840
atccagcagt tccccacgga agactggagt gcacagccag ccactgagga ttggtcagca    900
gctcccacag cgcaggccac tgagtgggtt ggagccacca ctgagtggtc cggatccgag    960
gtgaaagacg ttctgctgct tgatgttacc ccgctgagcc tgggtatcga gaccaagggc   1020
ggggtgatga ccaggctcat cgagcgcaac accacgatcc ccaccaagcg gtcggagact   1080
ttcaccaccg ccgacgacaa ccaaccgtcg gtgcagatcc aggtctatca gggggagcgt   1140
gagatcgccg cgcacaacaa gttgctcggg tccttcgagc tgaccggcat cccgccggcg   1200
ccgcggggga ttccgcagat cgaggtcact ttcgacatcg acgccaacgg cattgtgcac   1260
gtcaccgcca aggacaaggg caccggcaag gagaacacga tccgaatcca ggaaggctcg   1320
ggcctgtcca aggaagacat tgaccgcatg atcaaggacg ccgaagcgca cgccgaggag   1380
gatcgcaagc gtcgcgagga ggccgatgtt cgtaatcaag ccgagacatt ggtctaccag   1440
acggagaagt tcgtcaaaga acagcgtgag gccgagggtg gttcgaaggt acctgaagac   1500
acgctgaaca aggttgatgc cgcggtggcg gaagcgaagg cggcacttgg cggatcggat   1560
atttcggcca tcaagtcggc gatggagacg ctgggccagg agtcgcaggc tctggggcaa   1620
gcgatctacg aagcagctca ggctgcgtca caggccactg gcgctgccca ccccggcggc   1680
gagccgggcg gtgcccaccc cggctcggct gatagatctt aa                      1722
```

<210> SEQ ID NO 8
<211> LENGTH: 573
<212> TYPE: PRT
<213> ORGANISM: Artificial Sequence
<220> FEATURE:
<223> OTHER INFORMATION: Description of Artificial Sequence: Synthetic construct

<400> SEQUENCE: 8

```
Met Asn Pro Ser Ala Ala Val Ile Phe Cys Leu Ile Leu Leu Gly Leu
  1               5                  10                  15

Ser Gly Thr Gln Gly Ile Leu Asp Gly Ala Leu Asp Val Leu Gln Met
             20                  25                  30
```

```
Lys Glu Glu Asp Val Leu Lys Phe Leu Ala Ala Gly Thr His Leu Gly
        35                  40                  45

Gly Thr Asn Leu Asp Phe Gln Met Glu Gln Tyr Ile Tyr Lys Arg Lys
    50                  55                  60

Ser Asp Gly Ile Tyr Ile Ile Asn Leu Lys Arg Thr Trp Glu Lys Leu
65                  70                  75                  80

Leu Leu Ala Ala Arg Ala Ile Val Ala Ile Glu Asn Pro Ala Asp Val
                85                  90                  95

Ser Val Ile Ser Ser Arg Asn Thr Gly Gln Arg Ala Val Leu Lys Phe
            100                 105                 110

Ala Ala Ala Thr Gly Ala Thr Pro Ile Ala Gly Arg Phe Thr Pro Gly
        115                 120                 125

Thr Phe Thr Asn Gln Ile Gln Ala Ala Phe Arg Glu Pro Arg Leu Leu
    130                 135                 140

Val Val Thr Asp Pro Arg Ala Asp His Gln Pro Leu Thr Glu Ala Ser
145                 150                 155                 160

Tyr Val Asn Leu Pro Thr Ile Ala Leu Cys Asn Thr Asp Ser Pro Leu
                165                 170                 175

Arg Tyr Val Asp Ile Ala Ile Pro Cys Asn Asn Lys Gly Ala His Ser
            180                 185                 190

Val Gly Leu Met Trp Trp Met Leu Ala Arg Glu Val Leu Arg Met Arg
        195                 200                 205

Gly Thr Ile Ser Arg Glu His Pro Trp Glu Val Met Pro Asp Leu Tyr
    210                 215                 220

Phe Tyr Arg Asp Pro Glu Glu Ile Glu Lys Glu Glu Gln Ala Ala Ala
225                 230                 235                 240

Glu Lys Ala Val Thr Lys Glu Glu Phe Gln Gly Glu Trp Thr Ala Pro
                245                 250                 255

Ala Pro Glu Phe Thr Ala Ala Gln Pro Glu Val Ala Asp Trp Ser Glu
            260                 265                 270

Gly Val Gln Val Pro Ser Val Pro Ile Gln Gln Phe Pro Thr Glu Asp
        275                 280                 285

Trp Ser Ala Gln Pro Ala Thr Glu Asp Trp Ser Ala Ala Pro Thr Ala
    290                 295                 300

Gln Ala Thr Glu Trp Val Gly Ala Thr Thr Glu Trp Ser Gly Ser Glu
305                 310                 315                 320

Val Lys Asp Val Leu Leu Leu Asp Val Thr Pro Leu Ser Leu Gly Ile
                325                 330                 335

Glu Thr Lys Gly Gly Val Met Thr Arg Leu Ile Glu Arg Asn Thr Thr
            340                 345                 350

Ile Pro Thr Lys Arg Ser Glu Thr Phe Thr Thr Ala Asp Asp Asn Gln
        355                 360                 365

Pro Ser Val Gln Ile Gln Val Tyr Gln Gly Glu Arg Glu Ile Ala Ala
    370                 375                 380

His Asn Lys Leu Leu Gly Ser Phe Glu Leu Thr Gly Ile Pro Pro Ala
385                 390                 395                 400

Pro Arg Gly Ile Pro Gln Ile Glu Val Thr Phe Asp Ile Asp Ala Asn
                405                 410                 415

Gly Ile Val His Val Thr Ala Lys Asp Lys Gly Thr Gly Lys Glu Asn
            420                 425                 430

Thr Ile Arg Ile Gln Glu Gly Ser Gly Leu Ser Lys Glu Asp Ile Asp
        435                 440                 445
```

```
Arg Met Ile Lys Asp Ala Glu Ala His Ala Glu Glu Asp Arg Lys Arg
    450                 455                 460

Arg Glu Glu Ala Asp Val Arg Asn Gln Ala Glu Thr Leu Val Tyr Gln
465                 470                 475                 480

Thr Glu Lys Phe Val Lys Glu Gln Arg Glu Ala Glu Gly Gly Ser Lys
                485                 490                 495

Val Pro Glu Asp Thr Leu Asn Lys Val Asp Ala Ala Val Ala Glu Ala
            500                 505                 510

Lys Ala Ala Leu Gly Gly Ser Asp Ile Ser Ala Ile Lys Ser Ala Met
        515                 520                 525

Glu Thr Leu Gly Gln Glu Ser Gln Ala Leu Gly Gln Ala Ile Tyr Glu
    530                 535                 540

Ala Ala Gln Ala Ala Ser Gln Ala Thr Gly Ala Ala His Pro Gly Gly
545                 550                 555                 560

Glu Pro Gly Gly Ala His Pro Gly Ser Ala Asp Arg Ser
                565                 570
```

<210> SEQ ID NO 9
<211> LENGTH: 1104
<212> TYPE: DNA
<213> ORGANISM: Artificial Sequence
<220> FEATURE:
<223> OTHER INFORMATION: Description of Artificial Sequence: Synthetic construct

<400> SEQUENCE: 9

```
atgaacccaa gtgctgccgt cattttctgc ctcatcctgc tgggtctgag tgggactcaa     60

gggatctatt accaaattgt caactgcaag aaaagtgaag gacaatgtca agaatactgt    120

aatttcatgg aaacacaagt gggctactgt tcaaaaaaga aagaaccctg ctgcttacat    180

ccgttcgaat tcaacgacgc tcaggcgccg aagagtctcg acggagccct tgacgtcctg    240

cagatgaagg aggaggatgt cctcaaattc cttgctgcgg gaacccactt aggtggcacc    300

aaccttgact ttcagatgga gcagtacatc tacaaaagga aaagtgacgg tatctacatc    360

ataaacctga agaggacctg ggagaagctg ttgctcgcag ctcgagctat tgttgccatc    420

gagaatcctg ctgacgtcag cgtcatctcc tccaggaaca ctggccagcg agctgtgctg    480

aagtttgctg ctgccacagg agccactccg atcgctggcc gcttcacacc tgggaccttc    540

actaaccaga tccaagcagc cttcagggag ccacggcttc tagtggtgac cgatcccagg    600

gctgaccatc agccactcac agaggcctct tatgtcaacc tgcccaccat tgctctgtgt    660

aacacagatt ctcccctgcg ctatgtggac attgccatcc catgcaacaa caagggagct    720

cactcagtgg gtctgatgtg gtggatgctg gccagggaag tactccgcat gcgaggtact    780

atctcccgtg agcacccctg ggaggtcatg cctgatcttt acttctacag agacccagag    840

gagattgaga aggaggagca ggctgctgct gagaaggctg tgaccaagga ggaattccag    900

ggtgaatgga ccgcaccagc tcctgagttc actgctgctc agcctgaggt ggccgactgg    960

tctgagggtg tgcaggttcc ctctgtgccc atccagcagt tccccacgga agactggagt   1020

gcacagccag ccactgagga ttggtcagca gctcccacag cgcaggccac tgagtgggtt   1080

ggagccacca ctgagtggtc ctaa                                          1104
```

<210> SEQ ID NO 10
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 10

Leu Leu Leu Ala Ala Arg Ala Ile Val
  1               5


<210> SEQ ID NO 11
<211> LENGTH: 1206
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (679)
<223> OTHER INFORMATION: a, c, g, t, unknown or other

<400> SEQUENCE: 11

atgtgctgta ccaagagttt gctcctggct gctttgatgt cagtgctgct actccacctc     60

tgcggcgaat cagaagcagc aagcaacttt gactgctgtc ttggatacac agaccgtatt    120

cttcatccta aatttattgt gggcttcaca cggcagctgg ccaatggagg ctgtgacatc    180

aatgctatca tctttcacac aaagaaaaag ttgtctgtgt gcgcaaatcc aaaacagact    240

tgggtgaaat atattgtgcg tctcctcagt aaaaaagtca agaacatgga attcaacgac    300

gctcaggcgc cgaagagtct cgacggagcc cttgacgtcc tgcagatgaa ggaggaggat    360

gtcctcaaat tccttgctgc gggaacccac ttaggtggca ccaaccttga ctttcagatg    420

gagcagtaca tctacaaaag gaaaagtgac ggtatctaca tcataaacct gaagaggacc    480

tgggagaagc tgttgctcgc agctcgagct attgttgcca tcgagaatcc tgctgacgtc    540

agcgtcatct cctccaggaa cactggccag cgagctgtgc tgaagtttgc tgctgccaca    600

ggagccactc cgatcgctgg ccgcttcaca cctgggacct tcactaacca gatccaagca    660

gccttcaggg aggcacggnt tctagtggtg accgatccca gggctgacca tcagccactc    720

acagaggcct cttatgtcaa cctgcccacc attgctctgt gtaacacaga ttctcccctg    780

cgctatgtgg acattgccat cccatgcaac aacaagggag ctcactcagt gggtctgatg    840

tggtggatgc tggccaggga agtactccgc atgcgaggta ctatctcccg tgagcacccc    900

tgggaggtca tgcctgatct ttacttctac agagacccag aggagattga gaaggaggag    960

caggctgctg ctgagaaggc tgtgaccaag gaggaattcc agggtgaatg gaccgcacca   1020

gctcctgagt tcactgctgc tcagcctgag gtggccgact ggtctgaggg tgtgcaggtt   1080

ccctctgtgc ccatccagca gttccccacg gaagactgga gtgcacagcc agccactgag   1140

gattggtcag cagctcccac agcgcaggcc actgagtggg ttggagccac cactgagtgg   1200

tcctaa                                                              1206


<210> SEQ ID NO 12
<211> LENGTH: 401
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (227)
<223> OTHER INFORMATION: variable amino acid

<400> SEQUENCE: 12
```

```
Met Cys Cys Thr Lys Ser Leu Leu Leu Ala Ala Leu Met Ser Val Leu
  1               5                  10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Gly Gly Cys Asp Ile Asn Ala Ile Ile
    50                  55                  60

Phe His Thr Lys Lys Lys Leu Ser Val Cys Ala Asn Pro Lys Gln Thr
 65                  70                  75                  80

Trp Val Lys Tyr Ile Val Arg Leu Leu Ser Lys Lys Val Lys Asn Met
                85                  90                  95

Glu Phe Asn Asp Ala Gln Ala Pro Lys Ser Leu Asp Gly Ala Leu Asp
            100                 105                 110

Val Leu Gln Met Lys Glu Glu Asp Val Leu Lys Phe Leu Ala Ala Gly
        115                 120                 125

Thr His Leu Gly Gly Thr Asn Leu Asp Phe Gln Met Glu Gln Tyr Ile
    130                 135                 140

Tyr Lys Arg Lys Ser Asp Gly Ile Tyr Ile Ile Asn Leu Lys Arg Thr
145                 150                 155                 160

Trp Glu Lys Leu Leu Leu Ala Ala Arg Ala Ile Val Ala Ile Glu Asn
                165                 170                 175

Pro Ala Asp Val Ser Val Ile Ser Ser Arg Asn Thr Gly Gln Arg Ala
            180                 185                 190

Val Leu Lys Phe Ala Ala Ala Thr Gly Ala Thr Pro Ile Ala Gly Arg
        195                 200                 205

Phe Thr Pro Gly Thr Phe Thr Asn Gln Ile Gln Ala Ala Phe Arg Glu
    210                 215                 220

Ala Arg Xaa Leu Val Val Thr Asp Pro Arg Ala Asp His Gln Pro Leu
225                 230                 235                 240

Thr Glu Ala Ser Tyr Val Asn Leu Pro Thr Ile Ala Leu Cys Asn Thr
                245                 250                 255

Asp Ser Pro Leu Arg Tyr Val Asp Ile Ala Ile Pro Cys Asn Asn Lys
            260                 265                 270

Gly Ala His Ser Val Gly Leu Met Trp Trp Met Leu Ala Arg Glu Val
        275                 280                 285

Leu Arg Met Arg Gly Thr Ile Ser Arg Glu His Pro Trp Glu Val Met
    290                 295                 300

Pro Asp Leu Tyr Phe Tyr Arg Asp Pro Glu Glu Ile Glu Lys Glu Glu
305                 310                 315                 320

Gln Ala Ala Ala Glu Lys Ala Val Thr Lys Glu Glu Phe Gln Gly Glu
                325                 330                 335

Trp Thr Ala Pro Ala Pro Glu Phe Thr Ala Ala Gln Pro Glu Val Ala
            340                 345                 350

Asp Trp Ser Glu Gly Val Gln Val Pro Ser Val Pro Ile Gln Gln Phe
        355                 360                 365

Pro Thr Glu Asp Trp Ser Ala Gln Pro Ala Thr Glu Asp Trp Ser Ala
    370                 375                 380

Ala Pro Thr Ala Gln Ala Thr Glu Trp Val Gly Ala Thr Thr Glu Trp
385                 390                 395                 400

Ser
```

<210> SEQ ID NO 13
<211> LENGTH: 1101
<212> TYPE: DNA
<213> ORGANISM: Artificial Sequence
<220> FEATURE:
<223> OTHER INFORMATION: Description of Artificial Sequence: Synthetic construct
<220> FEATURE:
<221> NAME/KEY: modified_base
<222> LOCATION: (574)
<223> OTHER INFORMATION: a, c, g, t, unknown or other

<400> SEQUENCE: 13

```
atgaacccaa gtgctgccgt cattttctgc ctcatcctgc tgggtctgag tgggactcaa     60

gggatcctcg acatggatca ttacaattgc gtcagcagtg gagggcaatg tctctattct    120

gcctgcccga tctttaccaa aattcaaggc acctgttaca gagggaaggc caagtgctgc    180

aaggaattca acgacgctca ggcgccgaag agtctcgacg gagcccttga cgtcctgcag    240

atgaaggagg aggatgtcct caaattcctt gctgcgggaa cccacttagg tggcaccaac    300

cttgactttc agatggagca gtacatctac aaaaggaaaa gtgacggtat ctacatcata    360

aacctgaaga ggacctggga gaagctgttg ctcgcagctc gagctattgt tgccatcgag    420

aatcctgctg acgtcagcgt catctcctcc aggaacactg gccagcgagc tgtgctgaag    480

tttgctgctg ccacaggagc cactccgatc gctggccgct tcacacctgg gaccttcact    540

aaccagatcc aagcagcctt cagggaggca cggnttctag tggtgaccga tcccagggct    600

gaccatcagc cactcacaga ggcctcttat gtcaacctgc ccaccattgc tctgtgtaac    660

acagattctc ccctgcgcta tgtggacatt gccatcccat gcaacaacaa gggagctcac    720

tcagtgggtc tgatgtggtg gatgctggcc agggaagtac tccgcatgcg aggtactatc    780

tcccgtgagc acccctggga ggtcatgcct gatctttact tctacagaga cccagaggag    840

attgagaagg aggagcaggc tgctgctgag aaggctgtga ccaaggagga attccagggt    900

gaatggaccg caccagctcc tgagttcact gctgctcagc ctgaggtggc cgactggtct    960

gagggtgtgc aggttccctc tgtgcccatc cagcagttcc ccacggaaga ctggagtgca   1020

cagccagcca ctgaggattg gtcagcagct cccacagcgc aggccactga gtgggttgga   1080

gccaccactg agtggtccta a                                              1101
```

<210> SEQ ID NO 14
<211> LENGTH: 366
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (192)
<223> OTHER INFORMATION: variable amino acid

<400> SEQUENCE: 14

```
Met Asn Pro Ser Ala Ala Val Ile Phe Cys Leu Ile Leu Leu Gly Leu
  1               5                  10                  15

Ser Gly Thr Gln Gly Ile Leu Asp Met Asp His Tyr Asn Cys Val Ser
             20                  25                  30

Ser Gly Gly Gln Cys Leu Tyr Ser Ala Cys Pro Ile Phe Thr Lys Ile
         35                  40                  45

Gln Gly Thr Cys Tyr Arg Gly Lys Ala Lys Cys Cys Lys Glu Phe Asn
     50                  55                  60
```

```
Asp Ala Gln Ala Pro Lys Ser Leu Asp Gly Ala Leu Asp Val Leu Gln
 65                  70                  75                  80

Met Lys Glu Glu Asp Val Leu Lys Phe Leu Ala Ala Gly Thr His Leu
                 85                  90                  95

Gly Gly Thr Asn Leu Asp Phe Gln Met Glu Gln Tyr Ile Tyr Lys Arg
            100                 105                 110

Lys Ser Asp Gly Ile Tyr Ile Ile Asn Leu Lys Arg Thr Trp Glu Lys
        115                 120                 125

Leu Leu Leu Ala Ala Arg Ala Ile Val Ala Ile Glu Asn Pro Ala Asp
    130                 135                 140

Val Ser Val Ile Ser Ser Arg Asn Thr Gly Gln Arg Ala Val Leu Lys
145                 150                 155                 160

Phe Ala Ala Ala Thr Gly Ala Thr Pro Ile Ala Gly Arg Phe Thr Pro
                165                 170                 175

Gly Thr Phe Thr Asn Gln Ile Gln Ala Ala Phe Arg Glu Ala Arg Xaa
            180                 185                 190

Leu Val Val Thr Asp Pro Arg Ala Asp His Gln Pro Leu Thr Glu Ala
        195                 200                 205

Ser Tyr Val Asn Leu Pro Thr Ile Ala Leu Cys Asn Thr Asp Ser Pro
    210                 215                 220

Leu Arg Tyr Val Asp Ile Ala Ile Pro Cys Asn Asn Lys Gly Ala His
225                 230                 235                 240

Ser Val Gly Leu Met Trp Trp Met Leu Ala Arg Glu Val Leu Arg Met
                245                 250                 255

Arg Gly Thr Ile Ser Arg Glu His Pro Trp Glu Val Met Pro Asp Leu
            260                 265                 270

Tyr Phe Tyr Arg Asp Pro Glu Glu Ile Glu Lys Glu Glu Gln Ala Ala
        275                 280                 285

Ala Glu Lys Ala Val Thr Lys Glu Glu Phe Gln Gly Glu Trp Thr Ala
    290                 295                 300

Pro Ala Pro Glu Phe Thr Ala Ala Gln Pro Glu Val Ala Asp Trp Ser
305                 310                 315                 320

Glu Gly Val Gln Val Pro Ser Val Pro Ile Gln Gln Phe Pro Thr Glu
                325                 330                 335

Asp Trp Ser Ala Gln Pro Ala Thr Glu Asp Trp Ser Ala Ala Pro Thr
            340                 345                 350

Ala Gln Ala Thr Glu Trp Val Gly Ala Thr Thr Glu Trp Ser
        355                 360                 365


<210> SEQ ID NO 15
<211> LENGTH: 1104
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 15

atgaacccaa gtgctgccgt cattttctgc ctcatcctgc tgggtctgag tgggactcaa      60

gggatcctcg acatggatca ttacaattgc gtcagcagtg gagggcaatg tctctattct     120

gcctgcccga tctttaccaa aattcaaggc acctgttaca gagggaaggc caagtgctgc     180

aaggaattca acgacgctca ggcgccgaag agtctcgact ccggagccct tgatgtcctg     240

caaatgaagg aggaggatgt ccttaagttc cttgcagcag gaacccactt aggtggcacc     300

aatcttgact tccagatgga acagtacatc tataaaagga aaagtgatgg catctatatc     360
```

```
ataaatctca agaggacctg ggagaagctt ctgctggcag ctcgtgcaat tgttgccatt    420

gaaaaccctg ctgatgtcag tgttatatcc tccaggaata ctggccagag ggctgtgctg    480

aagtttgctg ctgccactgg agccactcca attgctggcc gcttcactcc tggaaccttc    540

actaaccaga tccaggcagc cttccgggag ccacggcttc ttgtggttac tgaccccagg    600

gctgaccacc agcctctcac ggaggcatct tatgttaacc tacctaccat tgcgctgtgt    660

aacacagatt ctcctctgcg ctatgtggac attgccatcc catgcaacaa caagggagct    720

cactcagtgg gtttaatgtg gtggatgctg gctcgggaag ttctgcgcat gcgtggcacc    780

atttcccgtg aacacccatg ggaggtcatg cctgatctgt acttctacag agatcctgaa    840

gagattgaaa aagaagagca ggctgctgct gagaaggcag tgaccaagga ggaatttcag    900

ggtgaatgga ctgctcccgc tcctgagttc actgctactc agcctgaggt tgcagactgg    960

tctgaaggtg tacaggtgcc ctctgtgcct attcagcaat tccctactga agactggagc   1020

gctcagcctg ccacggaaga ctggtctgca gctcccactg ctcaggccac tgaatgggta   1080

ggagcaacca ctgactggtc ttaa                                          1104
```

```
<210> SEQ ID NO 16
<211> LENGTH: 367
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 16

Met Asn Pro Ser Ala Ala Val Ile Phe Cys Leu Ile Leu Leu Gly Leu
  1               5                  10                  15

Ser Gly Thr Gln Gly Ile Leu Asp Met Asp His Tyr Asn Cys Val Ser
             20                  25                  30

Ser Gly Gly Gln Cys Leu Tyr Ser Ala Cys Pro Ile Phe Thr Lys Ile
         35                  40                  45

Gln Gly Thr Cys Tyr Arg Gly Lys Ala Lys Cys Cys Lys Glu Phe Asn
     50                  55                  60

Asp Ala Gln Ala Pro Lys Ser Leu Asp Ser Gly Ala Leu Asp Val Leu
 65                  70                  75                  80

Gln Met Lys Glu Glu Asp Val Leu Lys Phe Leu Ala Ala Gly Thr His
                 85                  90                  95

Leu Gly Gly Thr Asn Leu Asp Phe Gln Met Glu Gln Tyr Ile Tyr Lys
            100                 105                 110

Arg Lys Ser Asp Gly Ile Tyr Ile Ile Asn Leu Lys Arg Thr Trp Glu
        115                 120                 125

Lys Leu Leu Leu Ala Ala Arg Ala Ile Val Ala Ile Glu Asn Pro Ala
    130                 135                 140

Asp Val Ser Val Ile Ser Ser Arg Asn Thr Gly Gln Arg Ala Val Leu
145                 150                 155                 160

Lys Phe Ala Ala Ala Thr Gly Ala Thr Pro Ile Ala Gly Arg Phe Thr
                165                 170                 175

Pro Gly Thr Phe Thr Asn Gln Ile Gln Ala Ala Phe Arg Glu Pro Arg
            180                 185                 190

Leu Leu Val Val Thr Asp Pro Arg Ala Asp His Gln Pro Leu Thr Glu
        195                 200                 205

Ala Ser Tyr Val Asn Leu Pro Thr Ile Ala Leu Cys Asn Thr Asp Ser
    210                 215                 220
```

```
Pro Leu Arg Tyr Val Asp Ile Ala Ile Pro Cys Asn Asn Lys Gly Ala
225                 230                 235                 240

His Ser Val Gly Leu Met Trp Trp Met Leu Ala Arg Glu Val Leu Arg
                245                 250                 255

Met Arg Gly Thr Ile Ser Arg Glu His Pro Trp Glu Val Met Pro Asp
            260                 265                 270

Leu Tyr Phe Tyr Arg Asp Pro Glu Glu Ile Glu Lys Glu Glu Gln Ala
        275                 280                 285

Ala Ala Glu Lys Ala Val Thr Lys Glu Glu Phe Gln Gly Glu Trp Thr
    290                 295                 300

Ala Pro Ala Pro Glu Phe Thr Ala Thr Gln Pro Glu Val Ala Asp Trp
305                 310                 315                 320

Ser Glu Gly Val Gln Val Pro Ser Val Pro Ile Gln Gln Phe Pro Thr
                325                 330                 335

Glu Asp Trp Ser Ala Gln Pro Ala Thr Glu Asp Trp Ser Ala Ala Pro
            340                 345                 350

Thr Ala Gln Ala Thr Glu Trp Val Gly Ala Thr Thr Asp Trp Ser
        355                 360                 365
```

<210> SEQ ID NO 17
<211> LENGTH: 1209
<212> TYPE: DNA
<213> ORGANISM: Artificial Sequence
<220> FEATURE:
<223> OTHER INFORMATION: Description of Artificial Sequence: Synthetic construct

<400> SEQUENCE: 17

```
atgtgctgta ccaagagttt gctcctggct gctttgatgt cagtgctgct actccacctc     60

tgcggcgaat cagaagcagc aagcaacttt gactgctgtc ttggatacac agaccgtatt    120

cttcatccta aatttattgt gggcttcaca cggcagctgg ccaatggagg ctgtgacatc    180

aatgctatca tctttcacac aaagaaaaag ttgtctgtgt gcgcaaatcc aaaacagact    240

tgggtgaaat atattgtgcg tctcctcagt aaaaaagtca agaacatgga attcaacgac    300

gctcaggcgc cgaagagtct cgactccgga gcccttgatg tcctgcaaat gaaggaggag    360

gatgtcctta agttccttgc agcaggaacc cacttaggtg gcaccaatct tgacttccag    420

atggaacagt acatctataa aaggaaaagt gatggcatct atatcataaa tctcaagagg    480

acctgggaga agcttctgct ggcagctcgt gcaattgttg ccattgaaaa ccctgctgat    540

gtcagtgtta tatcctccag gaatactggc cagagggctg tgctgaagtt tgctgctgcc    600

actggagcca ctccaattgc tggccgcttc actcctggaa ccttcactaa ccagatccag    660

gcagccttcc gggagccacg gcttcttgtg gttactgacc ccagggctga ccaccagcct    720

ctcacggagg catcttatgt taacctacct accattgcgc tgtgtaacac agattctcct    780

ctgcgctatg tggacattgc catcccatgc aacaacaagg gagctcactc agtgggttta    840

atgtggtgga tgctggctcg ggaagttctg cgcatgcgtg gcaccatttc ccgtgaacac    900

ccatgggagg tcatgcctga tctgtacttc tacagagatc ctgaagagat tgaaaaagaa    960

gagcaggctg ctgctgagaa ggcagtgacc aaggaggaat ttcagggtga atggactgct   1020

cccgctcctg agttcactgc tactcagcct gaggttgcag actggtctga aggtgtacag   1080

gtgccctctg tgcctattca gcaattccct actgaagact ggagcgctca gcctgccacg   1140

gaagactggt ctgcagctcc cactgctcag gccactgaat gggtaggagc aaccactgac   1200
```

```
tggtcttaa                                                         1209


<210> SEQ ID NO 18
<211> LENGTH: 402
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 18

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Gly Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

Glu Phe Asn Asp Ala Gln Ala Pro Lys Ser Leu Asp Ser Gly Ala Leu
            100                 105                 110

Asp Val Leu Gln Met Lys Glu Glu Asp Val Leu Lys Phe Leu Ala Ala
        115                 120                 125

Gly Thr His Leu Gly Gly Thr Asn Leu Asp Phe Gln Met Glu Gln Tyr
    130                 135                 140

Ile Tyr Lys Arg Lys Ser Asp Gly Ile Tyr Ile Ile Asn Leu Lys Arg
145                 150                 155                 160

Thr Trp Glu Lys Leu Leu Leu Ala Ala Arg Ala Ile Val Ala Ile Glu
                165                 170                 175

Asn Pro Ala Asp Val Ser Val Ile Ser Ser Arg Asn Thr Gly Gln Arg
            180                 185                 190

Ala Val Leu Lys Phe Ala Ala Ala Thr Gly Ala Thr Pro Ile Ala Gly
        195                 200                 205

Arg Phe Thr Pro Gly Thr Phe Thr Asn Gln Ile Gln Ala Ala Phe Arg
    210                 215                 220

Glu Pro Arg Leu Leu Val Val Thr Asp Pro Arg Ala Asp His Gln Pro
225                 230                 235                 240

Leu Thr Glu Ala Ser Tyr Val Asn Leu Pro Thr Ile Ala Leu Cys Asn
                245                 250                 255

Thr Asp Ser Pro Leu Arg Tyr Val Asp Ile Ala Ile Pro Cys Asn Asn
            260                 265                 270

Lys Gly Ala His Ser Val Gly Leu Met Trp Trp Met Leu Ala Arg Glu
        275                 280                 285

Val Leu Arg Met Arg Gly Thr Ile Ser Arg Glu His Pro Trp Glu Val
    290                 295                 300

Met Pro Asp Leu Tyr Phe Tyr Arg Asp Pro Glu Glu Ile Glu Lys Glu
305                 310                 315                 320

Glu Gln Ala Ala Ala Glu Lys Ala Val Thr Lys Glu Glu Phe Gln Gly
                325                 330                 335

Glu Trp Thr Ala Pro Ala Pro Glu Phe Thr Ala Thr Gln Pro Glu Val
            340                 345                 350
```

```
Ala Asp Trp Ser Glu Gly Val Gln Val Pro Ser Val Pro Ile Gln Gln
        355                 360                 365

Phe Pro Thr Glu Asp Trp Ser Ala Gln Pro Ala Thr Glu Asp Trp Ser
    370                 375                 380

Ala Ala Pro Thr Ala Gln Ala Thr Glu Trp Val Gly Ala Thr Thr Asp
385                 390                 395                 400

Trp Ser


<210> SEQ ID NO 19
<211> LENGTH: 1044
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (601)
<223> OTHER INFORMATION: a, c, g, t, unknown or other

<400> SEQUENCE: 19

atggaacttg accactgcca caccaatgga gggtactgtg tcagagccat ttgtcctcct     60

tctgccaggc gtcctgggag ctgtttccca gagaacaacc cctgttgcaa gtacatgaaa    120

gatcttgaat tcaacgacgc tcaggcgccg aagagtctcg acggagccct tgacgtcctg    180

cagatgaagg aggaggatgt cctcaaattc cttgctgcgg gaacccactt aggtggcacc    240

aaccttgact ttcagatgga gcagtacatc tacaaaagga aaagtgacgg tatctacatc    300

ataaacctga agaggacctg ggagaagctg ttgctcgcag ctcgagctat tgttgccatc    360

gagaatcctg ctgacgtcag cgtcatctcc tccaggaaca ctggccagcg agctgtgctg    420

aagtttgctg ctgccacagg agccactccg atcgctggcc gcttcacacc tgggaccttc    480

actaaccaga tccaagcagc cttcagggag ccacggcttc tagtggtgac cgatcccagg    540

gctgaccatc agccactcac agaggcctct tatgtcaacc tgcccaccat tgctctgtgt    600

nacacagatt ctcccctgcg ctatgtggac attgccatcc catgcaacaa caagggagct    660

cactcagtgg gtctgatgtg gtggatgctg gccagggaag tactccgcat gcgaggtact    720

atctcccgtg agcacccctg ggaggtcatg cctgatcttt acttctacag agacccagag    780

gagattgaga aggaggagca ggctgctgct gagaaggctg tgaccaagga ggaattccag    840

ggtgaatgga ccgcaccagc tcctgagttc actgctgctc agcctgaggt ggccgactgg    900

tctgagggtg tgcaggttcc ctctgtgccc atccagcagt tccccacgga agactggagt    960

gcacagccag ccactgagga ttggtcagca gctcccacag cgcaggccac tgagtgggtt   1020

ggagccacca ctgagtggtc ctaa                                           1044


<210> SEQ ID NO 20
<211> LENGTH: 320
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (201)
<223> OTHER INFORMATION: variable amino acid

<400> SEQUENCE: 20

Met Glu Leu Asp His Cys His Thr Asn Gly Gly Tyr Cys Val Arg Ala
  1               5                  10                  15
```

```
Ile Cys Pro Pro Ser Ala Arg Arg Pro Gly Ser Cys Phe Pro Glu Asn
            20                  25                  30

Asn Pro Cys Cys Lys Tyr Met Lys Asp Leu Glu Phe Asn Asp Ala Gln
        35                  40                  45

Ala Pro Lys Ser Leu Asp Gly Ala Leu Asp Val Leu Gln Met Lys Glu
    50                  55                  60

Glu Asp Val Leu Lys Phe Leu Ala Ala Gly Thr His Leu Gly Gly Thr
65                  70                  75                  80

Asn Leu Asp Phe Gln Met Glu Gln Tyr Ile Tyr Lys Arg Lys Ser Asp
                85                  90                  95

Gly Ile Tyr Ile Ile Asn Leu Lys Arg Thr Trp Glu Lys Leu Leu Leu
            100                 105                 110

Ala Ala Arg Ala Ile Val Ala Ile Glu Asn Pro Ala Asp Val Ser Val
        115                 120                 125

Ile Ser Ser Arg Asn Thr Gly Gln Arg Ala Val Leu Lys Phe Ala Ala
    130                 135                 140

Ala Thr Gly Ala Thr Pro Ile Ala Gly Arg Phe Thr Pro Gly Thr Phe
145                 150                 155                 160

Thr Asn Gln Ile Gln Ala Ala Phe Arg Glu Pro Arg Leu Leu Val Val
                165                 170                 175

Thr Asp Pro Arg Ala Asp His Gln Pro Leu Thr Glu Ala Ser Tyr Val
            180                 185                 190

Asn Leu Pro Thr Ile Ala Leu Cys Xaa Thr Asp Ser Pro Leu Arg Tyr
        195                 200                 205

Val Asp Ile Ala Ile Pro Cys Asn Asn Lys Gly Ala His Ser Val Gly
    210                 215                 220

Leu Met Trp Trp Met Leu Ala Arg Glu Val Leu Arg Met Arg Gly Thr
225                 230                 235                 240

Ile Ser Arg Glu His Pro Trp Glu Val Met Pro Asp Leu Tyr Phe Tyr
                245                 250                 255

Arg Asp Pro Glu Glu Ile Glu Lys Glu Glu Gln Ala Ala Ala Glu Lys
            260                 265                 270

Ala Val Thr Lys Glu Glu Phe Gln Gly Glu Trp Thr Ala Pro Ala Pro
        275                 280                 285

Glu Phe Thr Ala Ala Gln Pro Glu Val Ala Asp Trp Ser Glu Gly Val
    290                 295                 300

Gln Val Pro Ser Val Pro Ile Gln Gln Phe Pro Thr Glu Asp Trp Ser
305                 310                 315                 320
```

```
<210> SEQ ID NO 21
<211> LENGTH: 1131
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (275)
<223> OTHER INFORMATION: a, c, g, t, unknown or other
<220> FEATURE:
<221> NAME/KEY: modified_base
<222> LOCATION: (405)
<223> OTHER INFORMATION: a, c, g, t, unknown or other

<400> SEQUENCE: 21

atggcaagca actacgactg ttgcctctcg tacatacaga cgcctcttcc ttccagagct     60
```

```
attgtgggtt tcacaagaca gatggccgat gaagcttgtg acattaatgc tatcatcttt    120

cacacgaaga aaagaaaatc tgtgtgcgct gatccaaagc agaactgggt gaaaagggct    180

gtgaacctcc tcagcctaag agtcaagaag atggaattca acgacgctca ggcgccgaag    240

agtctcgacg gagcccttga cgtcctgcag atganggagg aggatgtcct caaattcctt    300

gctgcgggaa cccacttagg tggcaccaac cttgattttc agatggagca gtacatctac    360

aaaaggaaaa gtgacggtat ctacatcata aacctgaaga ggacntggga gaagctgttg    420

ctcgcagctc gagctattgt tgccatcgag aatcctgctg acgtcagcgt catctcctcc    480

aggaacactg gccagcgagc tgtgctgaag tttgctgctg ccacaggagc cactccgatc    540

gctggccgct tcacacctgg gaccttcact aaccagatcc aagcagcctt cagggagcca    600

cggcttctag tggtgaccga tcccagggct gaccatcagc cactcacaga ggcctcttat    660

gtcaacctgc ccaccattgc tctgtgtaac acagattctc ccctgcgcta tgtggacatt    720

gccatcccat gcaacaacaa gggagctcac tcagtgggtc tgatgtggtg gatgctggcc    780

agggaagtac tccgcatgcg aggtactatc tcccgtgagc acccctggga ggtcatgcct    840

gatctttact tctacagaga cccagaggag attgagaagg aggagcaggc tgctgctgag    900

aaggctgtga ccaaggagga attccagggt gaatggaccg caccagctcc tgagttcact    960

gctgctcagc ctgaggtggc cgactggtct gagggtgtgc aggttccctc tgtgcccatc   1020

cagcagttcc ccacggaaga ctggagtgca cagccagcca ctgaggattg gtcagcagct   1080

cccacagcgc aggccactga gtgggttgga gccaccactg agtggtccta a            1131
```

<210> SEQ ID NO 22
<211> LENGTH: 376
<212> TYPE: PRT
<213> ORGANISM: Artificial Sequence
<220> FEATURE:
<223> OTHER INFORMATION: Description of Artificial Sequence: Synthetic construct
<220> FEATURE:
<221> NAME/KEY: MOD_RES
<222> LOCATION: (92)
<223> OTHER INFORMATION: variable amino acid

<400> SEQUENCE: 22

```
Met Ala Ser Asn Tyr Asp Cys Cys Leu Ser Tyr Ile Gln Thr Pro Leu
  1               5                  10                  15

Pro Ser Arg Ala Ile Val Gly Phe Thr Arg Gln Met Ala Asp Glu Ala
             20                  25                  30

Cys Asp Ile Asn Ala Ile Ile Phe His Thr Lys Lys Arg Lys Ser Val
         35                  40                  45

Cys Ala Asp Pro Lys Gln Asn Trp Val Lys Arg Ala Val Asn Leu Leu
     50                  55                  60

Ser Leu Arg Val Lys Lys Met Glu Phe Asn Asp Ala Gln Ala Pro Lys
 65                  70                  75                  80

Ser Leu Asp Gly Ala Leu Asp Val Leu Gln Met Xaa Glu Glu Asp Val
                 85                  90                  95

Leu Lys Phe Leu Ala Ala Gly Thr His Leu Gly Gly Thr Asn Leu Asp
            100                 105                 110

Phe Gln Met Glu Gln Tyr Ile Tyr Lys Arg Lys Ser Asp Gly Ile Tyr
        115                 120                 125

Ile Ile Asn Leu Lys Arg Thr Trp Glu Lys Leu Leu Leu Ala Ala Arg
    130                 135                 140

Ala Ile Val Ala Ile Glu Asn Pro Ala Asp Val Ser Val Ile Ser Ser
```

```
145                 150                 155                 160

Arg Asn Thr Gly Gln Arg Ala Val Leu Lys Phe Ala Ala Ala Thr Gly
                165                 170                 175

Ala Thr Pro Ile Ala Gly Arg Phe Thr Pro Gly Thr Phe Thr Asn Gln
            180                 185                 190

Ile Gln Ala Ala Phe Arg Glu Pro Arg Leu Leu Val Val Thr Asp Pro
        195                 200                 205

Arg Ala Asp His Gln Pro Leu Thr Glu Ala Ser Tyr Val Asn Leu Pro
    210                 215                 220

Thr Ile Ala Leu Cys Asn Thr Asp Ser Pro Leu Arg Tyr Val Asp Ile
225                 230                 235                 240

Ala Ile Pro Cys Asn Asn Lys Gly Ala His Ser Val Gly Leu Met Trp
                245                 250                 255

Trp Met Leu Ala Arg Glu Val Leu Arg Met Arg Gly Thr Ile Ser Arg
            260                 265                 270

Glu His Pro Trp Glu Val Met Pro Asp Leu Tyr Phe Tyr Arg Asp Pro
        275                 280                 285

Glu Glu Ile Glu Lys Glu Glu Gln Ala Ala Ala Glu Lys Ala Val Thr
    290                 295                 300

Lys Glu Glu Phe Gln Gly Glu Trp Thr Ala Pro Ala Pro Glu Phe Thr
305                 310                 315                 320

Ala Ala Gln Pro Glu Val Ala Asp Trp Ser Glu Gly Val Gln Val Pro
                325                 330                 335

Ser Val Pro Ile Gln Gln Phe Pro Thr Glu Asp Trp Ser Ala Gln Pro
            340                 345                 350

Ala Thr Glu Asp Trp Ser Ala Ala Pro Thr Ala Gln Ala Thr Glu Trp
        355                 360                 365

Val Gly Ala Thr Thr Glu Trp Ser
    370                 375


<210> SEQ ID NO 23
<211> LENGTH: 1131
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (604)
<223> OTHER INFORMATION: a, c, g, t, unknown or other

<400> SEQUENCE: 23

atggcaagca actttgactg ctgtcttgga tacacagacc gtattcttca tcctaaattt      60

attgtgggct tcacacggca gctggccaat ggaggctgtg acatcaatgc tatcatcttt     120

cacacaaaga aaaagttgtc tgtgtgcgca aatccaaaac agacttgggt gaaatatatt     180

gtgcgtctcc tcagtaaaaa agtcaagaac atggaattca acgacgctca ggcgccgaag     240

agtctcgacg gagcccttga cgtcctgcag atgaaggagg aggatgtcct caaattcctt     300

gctgcgggaa cccacttagg tggcaccaac cttgactttc agatggagca gtacatctac     360

aaaaggaaaa gtgacggtat ctacatcata aacctgaaga ggacctggga gaagctgttg     420

ctcgcagctc gagctattgt tgccatcgag aatcctgctg acgtcagcgt catctcctcc     480

aggaacactg gccagcgagc tgtgctgaag tttgctgctg ccacaggagc cactccgatc     540

gctggccgct tcacacctgg gaccttcact aaccagatcc aagcagcctt cagggaggca     600
```

```
cggnttctag tggtgaccga tcccagggct gaccatcagc cactcacaga ggcctcttat    660

gtcaacctgc ccaccattgc tctgtgtaac acagattctc ccctgcgcta tgtggacatt    720

gccatcccat gcaacaacaa gggagctcac tcagtgggtc tgatgtggtg gatgctggcc    780

agggaagtac tccgcatgcg aggtactatc tcccgtgagc accccctggga ggtcatgcct    840

gatctttact tctacagaga cccagaggag attgagaagg aggagcaggc tgctgctgag    900

aaggctgtga ccaaggagga attccagggt gaatggaccg caccagctcc tgagttcact    960

gctgctcagc ctgaggtggc cgactggtct gagggtgtgc aggttccctc tgtgcccatc   1020

cagcagttcc ccacggaaga ctggagtgca cagccagcca ctgaggattg gtcagcagct   1080

cccacagcgc aggccactga gtgggttgga gccaccactg agtggtccta a            1131
```

<210> SEQ ID NO 24
<211> LENGTH: 376
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (202)
<223> OTHER INFORMATION: variable amino acid

<400> SEQUENCE: 24

```
Met Ala Ser Asn Phe Asp Cys Cys Leu Gly Tyr Thr Asp Arg Ile Leu
  1               5                  10                  15

His Pro Lys Phe Ile Val Gly Phe Thr Arg Gln Leu Ala Asn Gly Gly
             20                  25                  30

Cys Asp Ile Asn Ala Ile Ile Phe His Thr Lys Lys Lys Leu Ser Val
         35                  40                  45

Cys Ala Asn Pro Lys Gln Thr Trp Val Lys Tyr Ile Val Arg Leu Leu
     50                  55                  60

Ser Lys Lys Val Lys Asn Met Glu Phe Asn Asp Ala Gln Ala Pro Lys
 65                  70                  75                  80

Ser Leu Asp Gly Ala Leu Asp Val Leu Gln Met Lys Glu Glu Asp Val
                 85                  90                  95

Leu Lys Phe Leu Ala Ala Gly Thr His Leu Gly Gly Thr Asn Leu Asp
            100                 105                 110

Phe Gln Met Glu Gln Tyr Ile Tyr Lys Arg Lys Ser Asp Gly Ile Tyr
        115                 120                 125

Ile Ile Asn Leu Lys Arg Thr Trp Glu Lys Leu Leu Leu Ala Ala Arg
    130                 135                 140

Ala Ile Val Ala Ile Glu Asn Pro Ala Asp Val Ser Val Ile Ser Ser
145                 150                 155                 160

Arg Asn Thr Gly Gln Arg Ala Val Leu Lys Phe Ala Ala Ala Thr Gly
                165                 170                 175

Ala Thr Pro Ile Ala Gly Arg Phe Thr Pro Gly Thr Phe Thr Asn Gln
            180                 185                 190

Ile Gln Ala Ala Phe Arg Glu Ala Arg Xaa Leu Val Val Thr Asp Pro
        195                 200                 205

Arg Ala Asp His Gln Pro Leu Thr Glu Ala Ser Tyr Val Asn Leu Pro
    210                 215                 220

Thr Ile Ala Leu Cys Asn Thr Asp Ser Pro Leu Arg Tyr Val Asp Ile
225                 230                 235                 240

Ala Ile Pro Cys Asn Asn Lys Gly Ala His Ser Val Gly Leu Met Trp
```

```
                245                 250                 255

Trp Met Leu Ala Arg Glu Val Leu Arg Met Arg Gly Thr Ile Ser Arg
            260                 265                 270

Glu His Pro Trp Glu Val Met Pro Asp Leu Tyr Phe Tyr Arg Asp Pro
        275                 280                 285

Glu Glu Ile Glu Lys Glu Glu Gln Ala Ala Ala Glu Lys Ala Val Thr
    290                 295                 300

Lys Glu Glu Phe Gln Gly Glu Trp Thr Ala Pro Ala Pro Glu Phe Thr
305                 310                 315                 320

Ala Ala Gln Pro Glu Val Ala Asp Trp Ser Glu Gly Val Gln Val Pro
                325                 330                 335

Ser Val Pro Ile Gln Gln Phe Pro Thr Glu Asp Trp Ser Ala Gln Pro
            340                 345                 350

Ala Thr Glu Asp Trp Ser Ala Ala Pro Thr Ala Gln Ala Thr Glu Trp
        355                 360                 365

Val Gly Ala Thr Thr Glu Trp Ser
    370                 375


<210> SEQ ID NO 25
<211> LENGTH: 1659
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 25

atgctcgacg gagcccttga cgtcctgcag atgaaggagg aggatgtcct caaattcctt     60

gctgcgggaa cccacttagg tggcaccaac cttgactttc agatggagca gtacatctac    120

aaaaggaaaa gtgacggtat ctacatcata aacctgaaga ggacctggga gaagctgttg    180

ctcgcagctc gagctattgt tgccatcgag aatcctgctg acgtcagcgt catctcctcc    240

aggaacactg gccagcgagc tgtgctgaag tttgctgctg ccacaggagc cactccgatc    300

gctggccgct tcacacctgg gaccttcact aaccagatcc aagcagcctt cagggagcca    360

cggcttctag tggtgaccga tcccagggct gaccatcagc cactcacaga ggcctcttat    420

gtcaacctgc ccaccattgc tctgtgtaac acagattctc ccctgcgcta tgtggacatt    480

gccatcccat gcaacaacaa gggagctcac tcagtgggtc tgatgtggtg gatgctggcc    540

agggaagtac tccgcatgcg aggtactatc tcccgtgagc acccctggga ggtcatgcct    600

gatctttact tctacagaga cccagaggag attgagaagg aggagcaggc tgctgctgag    660

aaggctgtga ccaaggagga attccagggt gaatggaccg caccagctcc tgagttcact    720

gctgctcagc ctgaggtggc cgactggtct gagggtgtgc aggttccctc tgtgcccatc    780

cagcagttcc ccacggaaga ctggagtgca cagccagcca ctgaggattg gtcagcagct    840

cccacagcgc aggccactga gtgggttgga gccaccactg agtggtccgg atccgaggtg    900

aaagacgttc tgctgcttga tgttaccccg ctgagcctgg gtatcgagac caagggcggg    960

gtgatgacca ggctcatcga gcgcaacacc acgatcccca ccaagcggtc ggagactttc   1020

accaccgccg acgacaacca accgtcggtg cagatccagg tctatcaggg ggagcgtgag   1080

atcgccgcgc acaacaagtt gctcgggtcc ttcgagctga ccggcatccc gccggcgccg   1140

cgggggattc cgcagatcga ggtcactttc gacatcgacg ccaacggcat tgtgcacgtc   1200

accgccaagg acaagggcac cggcaaggag aacacgatcc gaatccagga aggctcgggc   1260
```

```
ctgtccaagg aagacattga ccgcatgatc aaggacgccg aagcgcacgc cgaggaggat   1320

cgcaagcgtc gcgaggaggc cgatgttcgt aatcaagccg agacattggt ctaccagacg   1380

gagaagttcg tcaaagaaca gcgtgaggcc gagggtggtt cgaaggtacc tgaagacacg   1440

ctgaacaagg ttgatgccgc ggtggcggaa gcgaaggcgg cacttggcgg atcggatatt   1500

tcggccatca agtcggcgat ggagacgctg ggccaggagt cgcaggctct ggggcaagcg   1560

atctacgaag cagctcaggc tgcgtcacag gccactggcg ctgcccaccc cggcggcgag   1620

ccgggcggtg cccaccccgg ctcggctgat agatcttaa                          1659
```

```
<210> SEQ ID NO 26
<211> LENGTH: 552
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 26

Met Leu Asp Gly Ala Leu Asp Val Leu Gln Met Lys Glu Glu Asp Val
  1               5                  10                  15

Leu Lys Phe Leu Ala Ala Gly Thr His Leu Gly Gly Thr Asn Leu Asp
             20                  25                  30

Phe Gln Met Glu Gln Tyr Ile Tyr Lys Arg Lys Ser Asp Gly Ile Tyr
         35                  40                  45

Ile Ile Asn Leu Lys Arg Thr Trp Glu Lys Leu Leu Leu Ala Ala Arg
     50                  55                  60

Ala Ile Val Ala Ile Glu Asn Pro Ala Asp Val Ser Val Ile Ser Ser
 65                  70                  75                  80

Arg Asn Thr Gly Gln Arg Ala Val Leu Lys Phe Ala Ala Ala Thr Gly
                 85                  90                  95

Ala Thr Pro Ile Ala Gly Arg Phe Thr Pro Gly Thr Phe Thr Asn Gln
            100                 105                 110

Ile Gln Ala Ala Phe Arg Glu Pro Arg Leu Leu Val Val Thr Asp Pro
        115                 120                 125

Arg Ala Asp His Gln Pro Leu Thr Glu Ala Ser Tyr Val Asn Leu Pro
    130                 135                 140

Thr Ile Ala Leu Cys Asn Thr Asp Ser Pro Leu Arg Tyr Val Asp Ile
145                 150                 155                 160

Ala Ile Pro Cys Asn Asn Lys Gly Ala His Ser Val Gly Leu Met Trp
                165                 170                 175

Trp Met Leu Ala Arg Glu Val Leu Arg Met Arg Gly Thr Ile Ser Arg
            180                 185                 190

Glu His Pro Trp Glu Val Met Pro Asp Leu Tyr Phe Tyr Arg Asp Pro
        195                 200                 205

Glu Glu Ile Glu Lys Glu Glu Gln Ala Ala Ala Glu Lys Ala Val Thr
    210                 215                 220

Lys Glu Glu Phe Gln Gly Glu Trp Thr Ala Pro Ala Pro Glu Phe Thr
225                 230                 235                 240

Ala Ala Gln Pro Glu Val Ala Asp Trp Ser Glu Gly Val Gln Val Pro
                245                 250                 255

Ser Val Pro Ile Gln Gln Phe Pro Thr Glu Asp Trp Ser Ala Gln Pro
            260                 265                 270

Ala Thr Glu Asp Trp Ser Ala Ala Pro Thr Ala Gln Ala Thr Glu Trp
        275                 280                 285
```

```
Val Gly Ala Thr Thr Glu Trp Ser Gly Ser Glu Val Lys Asp Val Leu
    290                 295                 300

Leu Leu Asp Val Thr Pro Leu Ser Leu Gly Ile Glu Thr Lys Gly Gly
305                 310                 315                 320

Val Met Thr Arg Leu Ile Glu Arg Asn Thr Thr Ile Pro Thr Lys Arg
                325                 330                 335

Ser Glu Thr Phe Thr Thr Ala Asp Asp Asn Gln Pro Ser Val Gln Ile
            340                 345                 350

Gln Val Tyr Gln Gly Glu Arg Glu Ile Ala Ala His Asn Lys Leu Leu
        355                 360                 365

Gly Ser Phe Glu Leu Thr Gly Ile Pro Pro Ala Pro Arg Gly Ile Pro
    370                 375                 380

Gln Ile Glu Val Thr Phe Asp Ile Asp Ala Asn Gly Ile Val His Val
385                 390                 395                 400

Thr Ala Lys Asp Lys Gly Thr Gly Lys Glu Asn Thr Ile Arg Ile Gln
                405                 410                 415

Glu Gly Ser Gly Leu Ser Lys Glu Asp Ile Asp Arg Met Ile Lys Asp
            420                 425                 430

Ala Glu Ala His Ala Glu Glu Asp Arg Lys Arg Arg Glu Glu Ala Asp
        435                 440                 445

Val Arg Asn Gln Ala Glu Thr Leu Val Tyr Gln Thr Glu Lys Phe Val
    450                 455                 460

Lys Glu Gln Arg Glu Ala Glu Gly Gly Ser Lys Val Pro Glu Asp Thr
465                 470                 475                 480

Leu Asn Lys Val Asp Ala Ala Val Ala Glu Ala Lys Ala Ala Leu Gly
                485                 490                 495

Gly Ser Asp Ile Ser Ala Ile Lys Ser Ala Met Glu Thr Leu Gly Gln
            500                 505                 510

Glu Ser Gln Ala Leu Gly Gln Ala Ile Tyr Glu Ala Ala Gln Ala Ala
        515                 520                 525

Ser Gln Ala Thr Gly Ala Ala His Pro Gly Gly Glu Pro Gly Gly Ala
    530                 535                 540

His Pro Gly Ser Ala Asp Arg Ser
545                 550
```

```
<210> SEQ ID NO 27
<211> LENGTH: 1662
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 27

atgctcgact ccggagccct tgatgtcctg caaatgaagg aggaggatgt ccttaagttc      60

cttgcagcag gaacccactt aggtggcacc aatcttgact tccagatgga acagtacatc     120

tataaaagga aaagtgatgg catctatatc ataaatctca agaggacctg ggagaagctt     180

ctgctggcag ctcgtgcaat tgttgccatt gaaaaccctg ctgatgtcag tgttatatcc     240

tccaggaata ctggccagag ggctgtgctg aagtttgctg ctgccactgg agccactcca     300

attgctggcc gcttcactcc tggaaccttc actaaccaga tccaggcagc cttccgggag     360

ccacggcttc ttgtggttac tgaccccagg gctgaccacc agcctctcac ggaggcatct     420

tatgttaacc tacctaccat tgcgctgtgt aacacagatt ctcctctgcg ctatgtggac     480

attgccatcc catgcaacaa caagggagct cactcagtgg gtttaatgtg gtggatgctg     540
```

```
gctcgggaag ttctgcgcat gcgtggcacc atttcccgtg aacacccatg ggaggtcatg    600

cctgatctgt acttctacag agatcctgaa gagattgaaa aagaagagca ggctgctgct    660

gagaaggcag tgaccaagga ggaatttcag ggtgaatgga ctgctcccgc tcctgagttc    720

actgctactc agcctgaggt tgcagactgg tctgaaggtg tacaggtgcc ctctgtgcct    780

attcagcaat tccctactga agactggagc gctcagcctg ccacggaaga ctggtctgca    840

gctcccactg ctcaggccac tgaatgggta ggagcaacca ctgactggtc tggatccgag    900

gtgaaagacg ttctgctgct tgatgttacc ccgctgagcc tgggtatcga gaccaagggc    960

ggggtgatga ccaggctcat cgagcgcaac accacgatcc ccaccaagcg gtcggagact   1020

ttcaccaccg ccgacgacaa ccaaccgtcg gtgcagatcc aggtctatca gggggagcgt   1080

gagatcgccg cgcacaacaa gttgctcggg tccttcgagc tgaccggcat cccgccggcg   1140

ccgcggggga ttccgcagat cgaggtcact ttcgacatcg acgccaacgg cattgtgcac   1200

gtcaccgcca aggacaaggg caccggcaag gagaacacga tccgaatcca ggaaggctcg   1260

ggcctgtcca aggaagacat tgaccgcatg atcaaggacg ccgaagcgca cgccgaggag   1320

gatcgcaagc gtcgcgagga ggccgatgtt cgtaatcaag ccgagacatt ggtctaccag   1380

acggagaagt tcgtcaaaga acagcgtgag gccgagggtg gttcgaaggt acctgaagac   1440

acgctgaaca aggttgatgc cgcggtggcg gaagcgaagg cggcacttgg cggatcggat   1500

atttcggcca tcaagtcggc gatggagacg ctgggccagg agtcgcaggc tctggggcaa   1560

gcgatctacg aagcagctca ggctgcgtca caggccactg gcgctgccca ccccggcggc   1620

gagccgggcg gtgcccaccc cggctcggct gatagatctt aa                      1662
```

```
<210> SEQ ID NO 28
<211> LENGTH: 553
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 28

Met Leu Asp Ser Gly Ala Leu Asp Val Leu Gln Met Lys Glu Glu Asp
  1               5                  10                  15

Val Leu Lys Phe Leu Ala Ala Gly Thr His Leu Gly Gly Thr Asn Leu
             20                  25                  30

Asp Phe Gln Met Glu Gln Tyr Ile Tyr Lys Arg Lys Ser Asp Gly Ile
         35                  40                  45

Tyr Ile Ile Asn Leu Lys Arg Thr Trp Glu Lys Leu Leu Leu Ala Ala
     50                  55                  60

Arg Ala Ile Val Ala Ile Glu Asn Pro Ala Asp Val Ser Val Ile Ser
 65                  70                  75                  80

Ser Arg Asn Thr Gly Gln Arg Ala Val Leu Lys Phe Ala Ala Ala Thr
                 85                  90                  95

Gly Ala Thr Pro Ile Ala Gly Arg Phe Thr Pro Gly Thr Phe Thr Asn
            100                 105                 110

Gln Ile Gln Ala Ala Phe Arg Glu Pro Arg Leu Leu Val Val Thr Asp
        115                 120                 125

Pro Arg Ala Asp His Gln Pro Leu Thr Glu Ala Ser Tyr Val Asn Leu
    130                 135                 140

Pro Thr Ile Ala Leu Cys Asn Thr Asp Ser Pro Leu Arg Tyr Val Asp
145                 150                 155                 160
```

```
Ile Ala Ile Pro Cys Asn Asn Lys Gly Ala His Ser Val Gly Leu Met
                165                 170                 175

Trp Trp Met Leu Ala Arg Glu Val Leu Arg Met Arg Gly Thr Ile Ser
            180                 185                 190

Arg Glu His Pro Trp Glu Val Met Pro Asp Leu Tyr Phe Tyr Arg Asp
        195                 200                 205

Pro Glu Glu Ile Glu Lys Glu Glu Gln Ala Ala Ala Glu Lys Ala Val
    210                 215                 220

Thr Lys Glu Glu Phe Gln Gly Glu Trp Thr Ala Pro Ala Pro Glu Phe
225                 230                 235                 240

Thr Ala Thr Gln Pro Glu Val Ala Asp Trp Ser Glu Gly Val Gln Val
                245                 250                 255

Pro Ser Val Pro Ile Gln Gln Phe Pro Thr Glu Asp Trp Ser Ala Gln
            260                 265                 270

Pro Ala Thr Glu Asp Trp Ser Ala Ala Pro Thr Ala Gln Ala Thr Glu
        275                 280                 285

Trp Val Gly Ala Thr Thr Asp Trp Ser Gly Ser Glu Val Lys Asp Val
    290                 295                 300

Leu Leu Leu Asp Val Thr Pro Leu Ser Leu Gly Ile Glu Thr Lys Gly
305                 310                 315                 320

Gly Val Met Thr Arg Leu Ile Glu Arg Asn Thr Thr Ile Pro Thr Lys
                325                 330                 335

Arg Ser Glu Thr Phe Thr Thr Ala Asp Asp Asn Gln Pro Ser Val Gln
            340                 345                 350

Ile Gln Val Tyr Gln Gly Glu Arg Glu Ile Ala Ala His Asn Lys Leu
        355                 360                 365

Leu Gly Ser Phe Glu Leu Thr Gly Ile Pro Pro Ala Pro Arg Gly Ile
    370                 375                 380

Pro Gln Ile Glu Val Thr Phe Asp Ile Asp Ala Asn Gly Ile Val His
385                 390                 395                 400

Val Thr Ala Lys Asp Lys Gly Thr Gly Lys Glu Asn Thr Ile Arg Ile
                405                 410                 415

Gln Glu Gly Ser Gly Leu Ser Lys Glu Asp Ile Asp Arg Met Ile Lys
            420                 425                 430

Asp Ala Glu Ala His Ala Glu Glu Asp Arg Lys Arg Arg Glu Glu Ala
        435                 440                 445

Asp Val Arg Asn Gln Ala Glu Thr Leu Val Tyr Gln Thr Glu Lys Phe
    450                 455                 460

Val Lys Glu Gln Arg Glu Ala Glu Gly Gly Ser Lys Val Pro Glu Asp
465                 470                 475                 480

Thr Leu Asn Lys Val Asp Ala Ala Val Ala Glu Ala Lys Ala Ala Leu
                485                 490                 495

Gly Gly Ser Asp Ile Ser Ala Ile Lys Ser Ala Met Glu Thr Leu Gly
            500                 505                 510

Gln Glu Ser Gln Ala Leu Gly Gln Ala Ile Tyr Glu Ala Ala Gln Ala
        515                 520                 525

Ala Ser Gln Ala Thr Gly Ala Ala His Pro Gly Gly Glu Pro Gly Gly
    530                 535                 540

Ala His Pro Gly Ser Ala Asp Arg Ser
545                 550
```

<210> SEQ ID NO 29
<211> LENGTH: 1134

<212> TYPE: DNA
<213> ORGANISM: Artificial Sequence
<220> FEATURE:
<223> OTHER INFORMATION: Description of Artificial Sequence: Synthetic construct

<400> SEQUENCE: 29

```
atggcaagca actttgactg ctgtcttgga tacacagacc gtattcttca tcctaaattt     60
attgtgggct tcacacggca gctggccaat ggaggctgtg acatcaatgc tatcatcttt    120
cacacaaaga aaaagttgtc tgtgtgcgca aatccaaaac agacttgggt gaaatatatt    180
gtgcgtctcc tcagtaaaaa agtcaagaac atggaattca acgacgctca ggcgccgaag    240
agtctcgact ccggagccct tgatgtcctg caaatgaagg aggaggatgt ccttaagttc    300
cttgcagcag gaacccactt aggtggcacc aatcttgact tccagatgga acagtacatc    360
tataaaagga aaagtgatgg catctatatc ataaatctca agaggacctg ggagaagctt    420
ctgctggcag ctcgtgcaat tgttgccatt gaaaaccctg ctgatgtcag tgttatatcc    480
tccaggaata ctggccagag ggctgtgctg aagtttgctg ctgccactgg agccactcca    540
attgctggcc gcttcactcc tggaaccttc actaaccaga tccaggcagc cttccgggag    600
ccacggcttc ttgtggttac tgaccccagg gctgaccacc agcctctcac ggaggcatct    660
tatgttaacc tacctaccat tgcgctgtgt aacacagatt ctcctctgcg ctatgtggac    720
attgccatcc catgcaacaa caagggagct cactcagtgg gtttaatgtg gtggatgctg    780
gctcgggaag ttctgcgcat gcgtggcacc atttcccgtg aacacccatg ggaggtcatg    840
cctgatctgt acttctacag agatcctgaa gagattgaaa aagaagagca ggctgctgct    900
gagaaggcag tgaccaagga ggaatttcag ggtgaatgga ctgctcccgc tcctgagttc    960
actgctactc agcctgaggt tgcagactgg tctgaaggtg tacaggtgcc ctctgtgcct   1020
attcagcaat tccctactga agactggagc gctcagcctg ccacggaaga ctggtctgca   1080
gctcccactg ctcaggccac tgaatgggta ggagcaacca ctgactggtc ttaa         1134
```

<210> SEQ ID NO 30
<211> LENGTH: 377
<212> TYPE: PRT
<213> ORGANISM: Artificial Sequence
<220> FEATURE:
<223> OTHER INFORMATION: Description of Artificial Sequence: Synthetic construct

<400> SEQUENCE: 30

```
Met Ala Ser Asn Phe Asp Cys Cys Leu Gly Tyr Thr Asp Arg Ile Leu
  1               5                  10                  15

His Pro Lys Phe Ile Val Gly Phe Thr Arg Gln Leu Ala Asn Gly Gly
             20                  25                  30

Cys Asp Ile Asn Ala Ile Ile Phe His Thr Lys Lys Lys Leu Ser Val
         35                  40                  45

Cys Ala Asn Pro Lys Gln Thr Trp Val Lys Tyr Ile Val Arg Leu Leu
     50                  55                  60

Ser Lys Lys Val Lys Asn Met Glu Phe Asn Asp Ala Gln Ala Pro Lys
 65                  70                  75                  80

Ser Leu Asp Ser Gly Ala Leu Asp Val Leu Gln Met Lys Glu Glu Asp
                 85                  90                  95

Val Leu Lys Phe Leu Ala Ala Gly Thr His Leu Gly Gly Thr Asn Leu
            100                 105                 110

Asp Phe Gln Met Glu Gln Tyr Ile Tyr Lys Arg Lys Ser Asp Gly Ile
```

-continued

```
        115                 120                 125

Tyr Ile Ile Asn Leu Lys Arg Thr Trp Glu Lys Leu Leu Leu Ala Ala
    130                 135                 140

Arg Ala Ile Val Ala Ile Glu Asn Pro Ala Asp Val Ser Val Ile Ser
145                 150                 155                 160

Ser Arg Asn Thr Gly Gln Arg Ala Val Leu Lys Phe Ala Ala Ala Thr
                165                 170                 175

Gly Ala Thr Pro Ile Ala Gly Arg Phe Thr Pro Gly Thr Phe Thr Asn
            180                 185                 190

Gln Ile Gln Ala Ala Phe Arg Glu Pro Arg Leu Leu Val Val Thr Asp
        195                 200                 205

Pro Arg Ala Asp His Gln Pro Leu Thr Glu Ala Ser Tyr Val Asn Leu
    210                 215                 220

Pro Thr Ile Ala Leu Cys Asn Thr Asp Ser Pro Leu Arg Tyr Val Asp
225                 230                 235                 240

Ile Ala Ile Pro Cys Asn Asn Lys Gly Ala His Ser Val Gly Leu Met
                245                 250                 255

Trp Trp Met Leu Ala Arg Glu Val Leu Arg Met Arg Gly Thr Ile Ser
            260                 265                 270

Arg Glu His Pro Trp Glu Val Met Pro Asp Leu Tyr Phe Tyr Arg Asp
        275                 280                 285

Pro Glu Glu Ile Glu Lys Glu Glu Gln Ala Ala Ala Glu Lys Ala Val
    290                 295                 300

Thr Lys Glu Glu Phe Gln Gly Glu Trp Thr Ala Pro Ala Pro Glu Phe
305                 310                 315                 320

Thr Ala Thr Gln Pro Glu Val Ala Asp Trp Ser Glu Gly Val Gln Val
                325                 330                 335

Pro Ser Val Pro Ile Gln Gln Phe Pro Thr Glu Asp Trp Ser Ala Gln
            340                 345                 350

Pro Ala Thr Glu Asp Trp Ser Ala Ala Pro Thr Ala Gln Ala Thr Glu
        355                 360                 365

Trp Val Gly Ala Thr Thr Asp Trp Ser
    370                 375


<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Leu Trp Phe Arg Asn His Phe Val Phe Gly Gly Gly Thr Lys
  1               5                  10                  15
```

METHODS AND COMPOSITIONS FOR THE TREATMENT AND PREVENTION OF CANCER

RELATED APPLICATIONS

This application is a divisional of U.S. patent application Ser. No. 11/899,165, filed Sep. 3, 2007, now U.S. Pat. No. 8,258,278, which claims the benefit of U.S. Provisional Application No. 60/841,927, filed Sep. 1, 2006. The aforementioned patent applications are hereby incorporated by reference in their entirety.

BACKGROUND OF THE INVENTION

The basis for the high expectations of cancer immunotherapy is in its ability to eliminate the residual malignant cells and prevent relapse of the disease. The simplest method is to induce tumor-specific immunity by immunizing patients with the antigenic components of their tumors, so called tumor-associated antigens (TAAs). However, TAAs are often poorly immunogenic and their repertoire for immunotherapeutic use is quite limited. Unlike solid tumors, immunotherapy for B cell malignancies is further hampered by lack of well defined TAAs, except for the patient's unique idiotypic antibody (Id). Although efficacy of the Id vaccines both in preclinical studies and phase I-II clinical tests is demonstrably potent[2], a broader application of the vaccines may not be feasible due to the unpredictability of their T cell epitopes[3], needed for T cell responses, and the suppressive nature of tumor derived Id in the absence of continuing T cell help[4]. In addition, Id vaccines have to be custom tailored and individually produced for each patient. Idiotypic vaccines for some B cell malignancies have been shown to be effective both in animal models[9;32-34] and in phase I-III clinical trials[35]. However, a major limitation of this method is not only that the vaccine is individually produced for each patient (see review[36;37]), but also that the T cell epitopes essential for the protection may not always be expressed on Id.

Recently, the oncofetal Ag-immature laminin receptor 37-kDa protein, OFA-iLRP, was reported to be specifically expressed in different human tumors, such as breast, renal, lung and ovarian cancers, and in hematological malignancies[1]. OFA exists in two forms, as the dimerized high-affinity mature 67-kDa mLRP that may act as a cofactor to stabilize the binding of laminin to cell surface integrins, and the 37-kDa OFA-iLRP, which is not expressed by adult differentiated tissues[5]. The immunotherapeutic potential of OFA-iLRP has been recently proposed, as HLA-A2 specific $CD8^+$ cells, generated from the peripheral blood of healthy donors or cancer patients, lysed OFA-$iLRP^+$ acute myeloid leukemia (AML) and chronic lymphocytic leukemia (CLL) cells[6;7].

Unlike Id, OFA-iLRP is highly evolutionary conserved antigen that contains number of $CD8^+$ T cell epitopes expressed by human cancer cells[7]. Accordingly, a need exists for the development of anti-cancer vaccines that are not individually tailored and have broad ability to treat and prevent cancer, and OFA-iLRP may be useful if it can be made antigenic.

SUMMARY OF THE INVENTION

The inventors of the instant application have developed a novel strategy for rendering weakly or non-immunogenic self tumor antigens immunogenic. The strategy is based on use of proinflammatory chemokines to deliver antigens to immature DCs through targeting chemokine receptors differentially expressed on APCs[1;2]. Using the technology described herein, protein or DNA immunizations elicit therapeutic antitumor immunity against wide variety of tumors, which express non-immunogenic or weakly immunogenic tumor antigens, such as, for example, the embryonic antigen OFA.

Accordingly, the instant invention is based, at least in part, on the discovery that tumor-associated embryonic antigens, e.g., OFA-iLRP, though non-antigenic alone, are effective for the treatment and/or prevention of cancer when linked to a chemoattractant ligand, e.g., a proinflammatory chemokine such as MIP3α/CCL20 or β-defensin mDF2β. Accordingly, the instant invention provides methods and compositions for the treatment and prevention of cell proliferative disorders, e.g., cancer, using the discovered molecules.

In one aspect, the invention provides nucleic acid molecules encoding a tumor-associated embryonic antigen and a chemoattractant ligand. In one embodiment, the tumor-associated embryonic antigen is human or mouse OFA-iLRP. In another embodiment, the chemoattractant ligand is specific for CCR6, e.g., MIP3α/CCL20 or β-defensin DF2β. In particular embodiments, the chemoattractant ligand is human or murine. In another embodiment, the chemoattractant ligand is murine or human EP2C, murine or human β-defensin 1 (MBD1), or a C-terminal fragment of mycobacterial HSP 70.

In a specific embodiment, the invention provides nucleic acid molecules encoding β-defensin DF2β and OFA-iLRP, or functional fragments thereof. In another specific embodiment, the β-defensin DF2β is human β-defensin DF2β. In yet another specific embodiment, the β-defensin DF2β is murine β-defensin DF2β. The sequence of one exemplary nucleic acid molecule encoding β-defensin DF2β and OFA-iLRP is set forth as SEQ ID NO: 1.

In another specific embodiment, the invention provides nucleic acid molecules encoding MIP3α/CCL20 and OFA-iLRP, or functional fragments thereof. In one specific embodiment, the MIP3α/CCL20 is human MIP3α/CCL20. In yet another specific embodiment, the MIP3α/CCL20 is murine MIP3α/CCL20. The sequence of one exemplary nucleic acid molecule encoding MIP3α/CCL20 and OFA-iLRP is set forth as SEQ ID NO:3.

In another specific embodiment, the invention provides nucleic acid molecules encoding EP2C and OFA-iLRP, or functional fragments thereof. In one specific embodiment, the EP2C is human EP2C. In yet another specific embodiment, the EP2C is murine EP2C. The sequence of one exemplary nucleic acid molecule encoding EP2C and OFA-iLRP is set forth as SEQ ID NO: 5.

In another specific embodiment, the invention provides nucleic acid molecules encoding the C-terminal fragment of mycobacterial HSP 70 and OFA-iLRP, or functional fragments thereof. The sequence of one exemplary nucleic acid molecule encoding C-terminal fragment of mycobacterial HSP 70 and OFA-iLRP is set forth as SEQ ID NO: 7.

In specific embodiments, the OFA-iLRP is murine OFA-iLRP. In other specific embodiments, the OFA-iLRP is human OFA-iLRP.

In another embodiment, the invention provides nucleic acid molecules encoding a linker polypeptide between the tumor-associated embryonic antigen and the chemoattractant ligand. In another aspect, the embodiment, the invention provides nucleic acid molecules encoding a purification tag, e.g., a myc or his tag. In yet another embodiment, the invention provides nucleic acid molecules described herein further encoding a signal sequence, e.g., the IP 10 signal sequence.

In another aspect, the invention provides vectors comprising the nucleic acid molecules described herein.

In another aspect, the invention provides the nucleic acid molecules described herein for the treatment or prevention of cancer, e.g., hematological, breast, renal, lung or ovarian cancer.

In another aspect, the invention provides polypeptides comprising a tumor-associated embryonic antigen and a chemoattractant ligand. In one embodiment, the tumor-associated embryonic antigen is OFA-iLRP. In another embodiment, the chemoattractant ligand is specific for CCR6, e.g., MIP3α/CCL20 or β-defensin mDF2β. In one embodiment, the MIP3α/CCL20 or β-defensin DF2β is human or murine MIP3α/CCL20 or β-defensin DF2β.

In one embodiment, the chemoattractant ligand is murine or human EP2C, human β-defensin 1 (hBD1), or a C-terminal fragment of mycobacterial HSP 70.

In another embodiment, the invention provides polypeptides comprising β-defensin DF2β and OFA-iLRP, or functional fragments thereof. In a related embodiment, the β-defensin DF2β is human β-defensin DF2β. In another related embodiment, the β-defensin DF2β is murine β-defensin DF2β. The sequence of one exemplary polypeptide comprising β-defensin DF2β and OFA-iLRP is set forth as SEQ ID NO: 2.

In another embodiment, the invention provides polypeptides comprising MIP3α/CCL20 and OFA-iLRP, or functional fragments thereof. In a related embodiment, the MIP3α/CCL20 is human MIP3α/CCL20. In another related embodiment, the MIP3α/CCL20β is murine MIP3α/CCL20β. The sequence of one exemplary polypeptide comprising MIP3α/CCL20 and OFA-iLRP is set forth as SEQ ID NO:4.

In another embodiment, the invention provides polypeptides comprising EP2C and OFA-iLRP, or functional fragments thereof. In a related embodiment, the EP2C is human EP2C. In another related embodiment, the EP2C is murine EP2C. The sequence of one exemplary polypeptide comprising EP2C and OFA-iLRP is set forth as SEQ ID NO: 6.

In another embodiment, the invention provides polypeptides comprising a C-terminal fragment of mycobacterial HSP 70 and OFA-iLRP, or functional fragments thereof. The sequence of one exemplary polypeptide comprising a C-terminal fragment of mycobacterial HSP 70 and OFA-iLRP is set forth as SEQ ID NO: 8.

In certain embodiments, the OFA-iLRP is human OFA-iLRP. In other embodiments, the OFA-iLRP is murine OFA-iLRP.

In another embodiment, the invention provides polypeptides comprising a tumor-associated embryonic antigen and a chemoattractant ligand and further comprising a polypeptide linker between the tumor-associated embryonic antigen and the chemoattractant ligand.

In another embodiment, the invention provides polypeptides comprising a tumor-associated embryonic antigen and a chemoattractant ligand and further comprising a purification tag, e.g., a myc or his tag.

In another aspect, the instant invention provides a cancer vaccine comprising the nucleic acid molecules described herein and an adjuvant. In another aspect, the instant invention provides a cancer vaccine comprising one or more of the polypeptides described herein.

In another aspect, the instant invention also provides methods of treating a subject having cancer by administering to the subject a nucleic acid molecule or polypeptide as described herein, thereby treating the subject. In exemplary embodiments, the cancer is breast, renal, lung, ovarian or a hematological cancer.

In another aspect, the invention provides methods of immunizing a subject against cancer by administering to the subject a nucleic acid molecule, polypeptide or vaccine as described herein, thereby immunizing the subject.

The invention also provides a kit comprising a vaccine as described herein and instructions for use.

The invention also provides a kit comprising a nucleic acid as described herein and instructions for use.

The invention also provides a kit comprising a polypeptide as described herein and instructions for use.

BRIEF DESCRIPTION OF THE DRAWINGS

FIGS. 14.1-14.18 depict SEQ ID NOs: 1-30.

DETAILED DESCRIPTION OF THE INVENTION

Figure 1A:
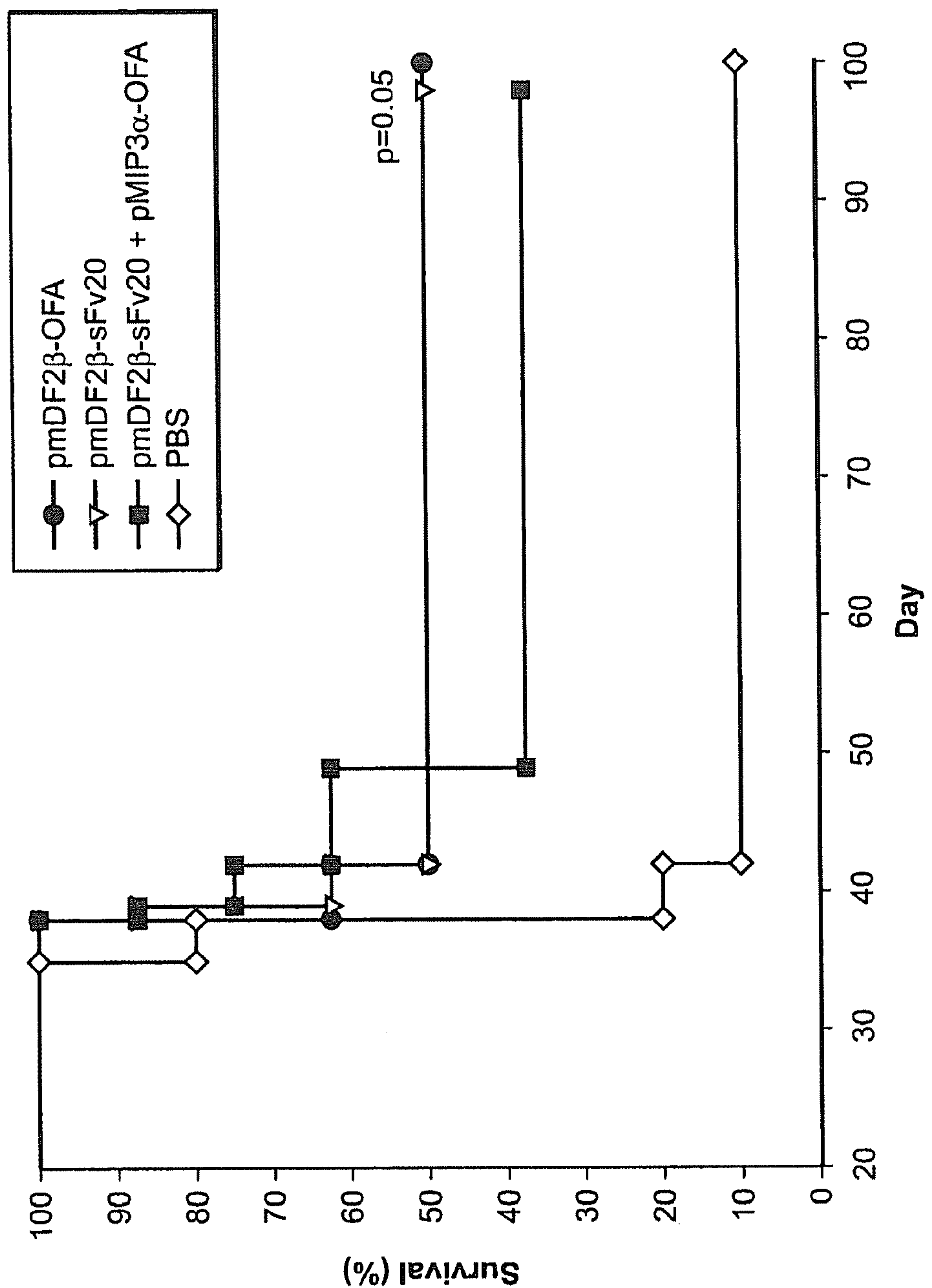
FIGS. 1A-B depict genetic immunizations with constructs expressing mDF2β fusions with non-immunogenic TAAs induce protective anti-lymphoma (A). BALB/c mice (ten per group), immunized with pmDF2β-OFA (closed circle) or pmDF2β-sFv20 (open triangle), were challenged i.p. with $2.5\times10^5$ A20 lymphoma cells. A separate group of mice were injected with a mixture of pmDF2β-sFv20 and pMIP3α-OFA (closed square) or mock with PBS (open diamond). Logrank P-value is for comparison between pmDF2β-OFA or pmDF2β-sFv20 and PBS. A representative experiment of at least three independent experiments is shown, all yielding similar results. (B) Mice immunized with pmDF2β-OFA generate significant OFA-specific IgG1 (open triangle) and IgG2a (closed triangle). Shown is representative plot of experiments of sera mixed five 5 mice per group. No OFA specific antibody was detected in sera of mock immunized mice (open circle, IgG1, and closed circle, IgG2a). Titrated amounts of immune or naïve mouse sera were incubated for 1 hour on the same plate coated with 3 μg/ml of recombinant TARC-OFA, and the Ig isotypes were determined using goat anti-mouse IgG1- or IgG2a-HRP antibodies (Caltag).

The instant invention is based, at least in part, on the discovery that non-immunogenic tumor antigens, e.g., OFA-iLRP, can be rendered immunogenic by using a chemoattractant ligand, e.g., a proinflammatory chemokine. In a preferred embodiment, the tumor antigen and chemoattractant ligand are expressed as a fusion polypeptide or are encoded by a single nucleic acid molecule. These molecules are useful in the prevention and treatment of cell proliferative disorders, e.g., cancer. Accordingly, the instant invention provides polypeptides, nucleic acid molecules, vectors, host cells, vaccines, kits and methods of treating or preventing cancer.

Molecules of the Invention

The present invention provides fusion molecules, e.g., molecules comprising a tumor antigen and chemoattractant ligand. The tumor antigen and chemoattractant ligand are optionally attached by a linker, e.g., a peptide or non-peptide linker. The invention provides polypeptides comprising a tumor antigen and chemoattractant ligand and nucleic acid molecules encoding a tumor antigen and chemoattractant ligand. In certain embodiments, the molecules comprise fragments of the tumor antigen and/or the chemoattractant ligand, wherein the fragments are effective to achieve the desired biological effect.

Exemplary tumor antigen are those that are expressed in embryonic tissue but not in mature tissue. An exemplary tumor antigen useful in the methods and compositions of the invention is the 37 kD oncofetal Ag-immature laminin receptor (OFA-iLRP) (SEQ ID NO:31).

Exemplary chemoattractant ligands include proinflammitory chemokines. Specific exemplary chemoattractant ligands include chemoattractant ligands specific for CCR6, e.g., MIP3α/CCL20 or β-defensin DF2β. Further chemoattractant ligands include EP2C, β-defensin 1 (MBD1), or a C-terminal fragment of mycobacterial HSP 70. For all chemoattractant ligands other than mycobacterial HSP 70, the chemoattractant can be human or murine. The sequence of all the exemplary chemoattractant ligands set forth herein are set forth in the sequence of the exemplary polypeptides and nucleic acid molecules set forth herein.

One of skill in the art can identify chemoattractant ligands and understands that homologues and orthologues of these molecules will be useful in the methods and compositions of the instant invention. Moreover, variants and biologically active fragments of these ligands are useful in the methods of the invention.

The polypeptides of the invention may be assembled post-translationally, i.e., the tumor antigen and chemoattractant ligand can be covalently linked after being synthesized, or expressed, separately. Alternatively, the tumor antigen and chemoattractant ligand can be expressed recombinantly as one polypeptide.

The polypeptides of the invention may further comprise a polypeptide linker located between the tumor antigen and chemoattractant ligand. The polypeptides of the invention may further comprise one or more purification tags, e.g., a myc or histidine tag. Finally, the polypeptides of the invention may comprise a signal sequence to direct the location of the polypeptide.

The invention also provides nucleic acid molecules encoding a tumor antigen and chemoattractant ligand such as those described herein. Moreover, the nucleic acid molecules may further encode a polypeptide linker located between the tumor antigen and chemoattractant ligand. The nucleic acid molecules of the invention may further encode a signal sequence to direct the location of the polypeptide. The nucleic acid molecules of the invention may further encode a purification tag, e.g., a myc or histidine tag.

The invention also provides vectors, e.g., expression vectors, containing a nucleic acid molecule of the invention. As used herein, the term "vector" refers to a nucleic acid molecule capable of transporting another nucleic acid molecule to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid molecule of the invention in a form suitable for expression of the nucleic acid molecule in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., fusion molecules comprising a chemokine receptor ligand and a toxin moiety).

The recombinant expression vectors of the invention can be designed for expression of the polypeptides of the invention in prokaryotic or eukaryotic cells. For example, the polypeptides can be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) Gene 69:301-315) and pET 11d (Studier et a, Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of the invention can be carried out by standard DNA synthesis techniques.

In another embodiment, the expression vector is a yeast expression vector. Examples of vectors for expression in yeast S. cerivisae include pYepSec1 (Baldari, et al., (1987) EMBO J 6:229-234), pMFa (Kudjan and Herskowitz, (1982) Cell 30:933-943), pJRY88 (Schultz et al., (1987) Gene 54:113-123), pYES2 (Invitrogen Corporation, San Diego, Calif.), and picZ (InVitrogen Corp, San Diego, Calif.).

Alternatively, the nucleic acid molecules of the invention may be used to express polypeptides in insect cells using baculovirus expression vectors. Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J 8:729-733) and immunoglobulins (Banedji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

Another aspect of the invention pertains to host cells into which a nucleic acid molecule encoding a polypeptide of the invention is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the invention can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAF-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the polypeptide of the invention or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the polypeptides of the invention. Accordingly, the invention further provides methods for producing polypeptides using the host cells of the invention. In one embodiment, the method comprises culturing the host cell of the invention (into which a recombinant expression vector encoding a polypeptide of the invention has been introduced) in a suitable medium such that a polypeptides of the invention is produced. In another embodiment, the method further comprises isolating the polypeptide from the medium or the host cell.

The host cells of the invention can also be used to produce non-human transgenic animals. For example, in one embodiment, a host cell of the invention is a fertilized oocyte or an embryonic stem cell into which coding sequences have been introduced. Such host cells can then be used to create non-human transgenic animals in which exogenous sequences have been introduced into their genome or homologous recombinant animals in which endogenous sequences have been altered. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like.

Methods of Making the Molecules of the Invention

As described above, molecules of the invention may be made recombinantly using the nucleic acid molecules, vectors, and host cells described above.

Alternatively, the tumor antigen and chemoattractant ligand can be made synthetically, or isolated from a natural source and linked together using methods and techniques well known to one of skill in the art.

Further, to increase the stability or half life of the fusion molecules of the invention, the peptides may be made, e.g., synthetically or recombinantly, to include one or more peptide analogs or mimmetics. Exemplary peptides can be synthesized to include D-isomers of the naturally occurring amino acid residues to increase the half life of the molecule when administered to a subject.

Pharmaceutical Compositions

The nucleic acid and polypeptide fusion molecules (also referred to herein as "active compounds") of the invention can be incorporated into pharmaceutical compositions. Such compositions typically include the nucleic acid molecule or protein, and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

Pharmaceutical compositions of the instant invention may also include one or more other active compounds. Alternatively, the pharmaceutical compositions of the invention may be administered with one or more other active compounds. Other active compounds that can be administered with the pharmaceutical compounds of the invention, or formulated into the pharmaceutical compositions of the invention, include, for example, anticancer compounds.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Preferred pharmaceutical compositions of the invention are those that allow for local delivery of the active ingredient, e.g., delivery directly to the location of a tumor.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a polypeptide or nucleic acid molecule can include a single treatment or, preferably, can include a series of treatments.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, kit or dispenser together with instructions, e.g., written instructions, for administration, particularly such instructions for use of the active agent to treat against a disorder or disease as disclosed herein, including an autoimmune disease or disorder, treatment in connection with an organ or tissue transplant, as well as other diseases or disorders with an autoimmune component such as AIDS. The container, pack, kit or dispenser may also contain, for example, a fusion molecule, a nucleic acid sequence encoding a fusion molecule, or a fusion molecule expressing cell.

Methods of Treatment

The compositions disclosed herein may be useful in the treatment or prevention of cancer.

The term "cancer" includes malignancies characterized by deregulated or uncontrolled cell growth, for instance carcinomas, sarcomas, leukemias, and lymphomas. The term "cancer" includes primary malignant tumors, e.g., those whose cells have not migrated to sites in the subject's body other than the site of the original tumor, and secondary malignant tumors, e.g., those arising from metastasis, the migration of tumor cells to secondary sites that are different from the site of the original tumor.

The term "leukemia" includes malignancies of the hematopoietic cells of the bone marrow. Leukemias tend to proliferate as single cells. Examples of leukemias include acute myeloid leukemia (AML), acute promyelocytic leukemia, chronic myelogenous leukemia, mixed-lineage leukemia, acute monoblastic leukemia, acute lymphoblastic leukemia, acute non-lymphoblastic leukemia, blastic mantle cell leukemia, myelodyplastic syndrome, T cell leukemia, B cell leukemia, and chronic lymphocytic leukemia. Preferred leukemias include T cell malignancies, e.g., T cell leukemia and myeloma.

The invention provides therapeutic methods and compositions for the prevention and treatment of cancer and for the administration of a vaccine to a subject.

In one embodiment, the present invention contemplates a method of treatment, comprising: a) providing, i.e., administering: i) a mammalian patient particularly human who has, or is at risk of developing, cancer, ii) one or more molecules of the invention.

The term "at risk for developing" is herein defined as individuals with familial incidence of, for example, cancer.

The present invention is also not limited by the degree of benefit achieved by the administration of the fusion molecule. For example, the present invention is not limited to circumstances where all symptoms are eliminated. In one embodiment, administering a fusion molecule reduces the number or severity of symptoms of cancer. In another embodiment, administering of a fusion molecule may delay the onset of symptoms.

Typical subjects for treatment in accordance with the individuals include mammals, such as primates, preferably humans. Cells treated in accordance with the invention also preferably are mammalian, particularly primate, especially human. As discussed above, a subject or cells are suitably identified as in needed of treatment, and the identified cells or subject are then selected for treatment and administered one or more of fusion molecules of the invention.

The treatment methods and compositions of the invention also will be useful for treatment of mammals other than humans, including for veterinary applications such as to treat horses and livestock e.g. cattle, sheep, cows, goats, swine and the like, and pets such as dogs and cats.

For diagnostic or research applications, a wide variety of mammals will be suitable subjects including rodents (e.g. mice, rats, hamsters), rabbits, primates and swine such as inbred pigs and the like. Additionally, for in vitro applications, such as in vitro diagnostic and research applications, body fluids (e.g., blood, plasma, serum, cellular interstitial fluid, saliva, feces and urine) and cell and tissue samples of the above subjects will be suitable for use.

Vaccines

The preparation of vaccine compositions that contain the nucleic acid molecules or polypeptides of the invention as an effective ingredient is known to one skilled in the art. Typically, such vaccines are prepared as injectables, either as liquid solutions or suspensions; solid forms suitable for solution in, or suspension in, liquid prior to infection can also be prepared. The preparation can also be emulsified, or the protein encapsulated in liposomes. The active immunogenic ingredients are often mixed with carriers which are pharmaceutically acceptable and compatible with the active ingredient. The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the vaccine can contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosporyl lipid A, trehalose dimycolate and cell wall skeleton (MPL+TDM+CWS) in a 2% squalene/Tween 80 emulsion. Other examples of adjuvants include DDA (dimethyldioctadecylammonium bromide), Freund's complete and incomplete adjuvants and QuilA. In addition, immune modulating substances such as lymphokines (e.g., IFN-g, IL-2 and IL-12) or synthetic IFN-g inducers such as poly I:C can be used in combination with adjuvants described herein.

Vaccine compositions of the present invention may be administered parenterally, by injection, for example, either subcutaneously or intramuscularly. The vaccine compositions can further be delivered by a gene gun. Additional formulations which are suitable for other modes of administration include suppositories, and in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5 to 10%, preferably I to 2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10% to 95% of effective ingredient, preferably 25 to 70%.

The nucleic acid molecules and proteins of the present invention can be formulated into the vaccine compositions as neutral or salt forms. Pharmaceutically acceptable salts include the acid addition salts (formed with free amino groups of the peptide) and which are formed with inorganic acids such as, for example, hydrochloric or phosphoric acids, or with organic acids such as acetic, oxalic, tartaric, maleic, and the like. Salts formed with the free carboxyl groups can also be derived from inorganic bases such as, for example, sodium, potassium, ammonium, calcium, or ferric hydroides, and such organic bases as isopropylamine, trimethylamine, 2-ethylamino ethanol, histidine, procaine, and the like.

Vaccine compositions are administered in a manner compatible with the dosage formulation, and in such amount as will be prophylactically and/or therapeutically effective. The quantity to be administered depends on the subject to be treated, including, e.g., capacity of the subject's immune system to synthesize antibodies, and the degree of protection or treatment desired. Suitable dosage ranges are of the order of several hundred micrograms effective ingredient per vaccination with a range from about 0.01 to 10 mg/kg/day, preferably in the range from about 0.1 to 1 mg/kg/day. Suitable regiments for initial administration and booster shots are also variable but are typified by an initial administration followed by subsequent inoculations or other administrations. Precise amounts of effective ingredient required to be administered depend on the judgment of the practitioner and may be peculiar to each subject. It will be apparent to those of skill in the art that the therapeutically effective amount the vaccine of this invention will depend, inter alia, upon the administration schedule, the unit dose of antigen administered, whether the vaccine is administered in combination with other therapeutic agents, the immune status and health of the recipient, and the therapeutic activity of the particular vaccine.

The vaccine can be given in a single dose schedule, or preferably in a multiple dose schedule. A multiple dose schedule is one in which a primary course of vaccination can include 1 to 10 separate doses, followed by other doses given at subsequent time intervals required to maintain and or reinforce the immune response, for example, at 1 to 4 months for a second dose, and if needed, a subsequent dose(s) after several months. Periodic boosters at intervals of 1 to 5 years, usually 3 years, are desirable to maintain the desired levels of protective immunity.

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

In one aspect, an adjuvant effect is achieved by use of an agent such as alum used in about 0.05 to about 0.1% solution in phosphate buffered saline. Alternatively, the antigen is made as an admixture with synthetic polymers of sugars used as an about 0.25% solution. Adjuvant effect may also be made by aggregation of the antigen in the vaccine by heat treatment. Aggregation by reactivating with pepsin treated (Fab) antibodies to albumin, mixture with bacterial cell(s) such as C. parvum or an endotoxin or a lipopolysaccharide components of Gram-negative bacteria, emulsion in physiologically acceptable oil vehicles such as mannide monooleate (Aracel A) or emulsion with a 20% solution of a perfluorocarbon used as a block substitute also may be employed.

Various polysaccharide adjuvants may also be used. For example, the use of various pneumococcal polysaccharide adjuvants on the antibody responses of mice has been described. The doses that produce optimal responses, or that otherwise do not produce suppression, should be employed as indicated. Polyamine varieties of polysaccharides are particularly preferred, such as chitin and chitosan, including deacetylated chitin.

EXAMPLES

It should be appreciated that the invention should not be construed to be limited to the examples that are now described; rather, the invention should be construed to include any and all applications provided herein and all equivalent variations within the skill of the ordinary artisan.

Materials and Methods

Fusion Gene Cloning and Protein Production

Generation of DNA vaccine constructs expressing murine MIP3α/CCL20, murine β-defensin 2 (mDF2β) and Hsp70 fused with tumor antigens (OFA-iLRP or sFv20) was previously described[8, 9]. Hsp70 cDNA was a generous gift from Dr. Thomas Lehner (Guy's Hospital, London, UK). Murine OFA-iLRP, (OFA, GeneBank # AF140348) was cloned from murine B cell A20 lymphoma (American Type Culture Collection, (ATCC) Manassas, Va.). All constructs were verified by the DNA sequencing (Fidelity Systems, Inc., Gaithersburg, Md.). To generate the DNA vaccine, the chemokine-OFA was cloned in pVAX1 plasmid (Invitrogen). Chemoattractant-OFA proteins were produced from IPTG-induced BL21(DE3) cells (Stratagene) using bacterial expression vector pET11d (Stratagene) and purified (>90% purity) from inclusion bodies as described previously[8,15]. The peptides $iLR_{58-66}$ (LLLAARAIV)[6], MOPC-315 $Ig_{91-101}$ (ALWFRNHFVFGGGTK)[16] were all synthesized by Peptide Technologies (Washington, D.C.) to a purity >99% by HPLC and amino acid analysis.

Cell Lines

The A20 B cell lymphoma (H-$2^d$, OFA-iLRP positive), MOPC315 plasmacytoma (H-$2^d$, OFA-iLRP negative) and EL-4 thymoma (H-$2^b$, OFA-iLRP positive) cell lines were purchased from ATCC. The B6/129 macrophage cell line (H-$2^d$, CCR6 positive by FACS analysis) was a generous gift from Dr. Howard Young (NCI, MD). Murine bone marrow (BM)-derived DC preparation was previously described[17]. Cells used on day 4-5 of cultivation, that usually yields iDCs[11].

Immunizations of Mice

All animals were bred or housed at the National Institute of Aging animal facility, Baltimore, Md. Animal care was provided in accordance with the procedures outlined in a Guide for the Care and Use of Laboratory Animals (NIH Publication No. 86-23, 1985). For tumor protection study, six- to eight-week old female BALB/C mice (ten per group) were immunized three times every two weeks by electroporating 25 μg DNA in 50 μl endo-free water intradermally (i.d.) into the base of tail using 4 mm-gapped electrodes and PA4000 electric pulse generator (Cyto Pulse Sciences, Inc., Linthicum, Md.) at the following settings: 2 pulses at 450V, 0.125 S and 0.05 mS. Two weeks after the last immunization, mice were challenged i.p. with $2\times10^5$ A20 lymphoma cells and mice were followed for tumor survival. For therapy studies, six- to eight-week old female BALB/C mice (ten per group) were challenged i.p. with $2\times10^5$ A20 lymphoma cells at day 0, and then immunized with DNA constructs at days 3, 8 and 18. Differences in survival between groups were determined by non-parametric logrank test (BMDP statistical software, Los Angeles).

Preparation of Immune Effector Cells, In Vitro Activation of T Cells

Mice were vaccinated s.c. twice at 3-wk intervals with 10 μg human $iLR_{58-66}$ peptide emulsified in 100 μl incomplete Freund's adjuvant (IFA). Three weeks after the second vaccination, splenocytes were cultured with 20 IU/ml rhIL-2 and 1 μg/ml corresponding peptide (irrelevant MOPC-315 $Ig_{91-101}$ or $iLR_{58-66}$, respectively) and used on days 5-7 after the initiation of the culture.

In Vivo T Cell Subset Depletions.

In vivo antibody depletions started 2 weeks after vaccination by treatment with three i.p. doses of 400 μg anti-CD8 mAb GK 2.43 or anti-CD4 mAb GK1.5 (NCI-FCRDC, Frederick, Md.), or normal rat IgG (Sigma) every other day two weeks after the last immunization, prior to tumor challenge. Depletion of lymphocyte subsets was assessed 1 week after final treatment by flow cytometry analysis of splenocytes from normal mice treated with these mAb in parallel[8].

Chemokine Receptor Binding

The ligand binding-internalization assays were performed with iDC or splenocytes ($1\times10^5$) blocked with mouse serum in PBS containing 2% BSA. Fusion proteins (10-50 μg/ml) were incubated in complete medium for 1 h at 37° C. or at 4° C. To detect bound proteins, the cells were incubated with anti-c-myc mAb or isotype-matched, purified mouse IgG1, followed with a-mouse Ig-FITC mAb incubation (Jackson ImmunoResearch Laboratory, Bar Harbor, Me.) for 20 min each, and then fixed with 1% paraformaldehyde. The binding-internalization was assessed via flow cytometry on a FACScan (Becton Dickinson, Franklin Lakes, N.J.) using CellQuest software.

Intracellular Antigen Processing

Antigen presenting cells, splenocytes or iDC, from naïve BALB/c mice were incubated overnight with various concentrations of fusion protein (0.01-1 μg/ml). The treated APCs were subsequently irradiated (2000 Rad), washed twice with PBS to remove unbound proteins, and then cocultured for 24-48 h with specific effector cells from the $iLR_{58-66}$ (or irrelevant MOPC-315 $Ig_{91-101}$) peptide immunized mice. Some APCs were treated overnight with chemokine fused with various inhibitors: pertussis toxin (PTX, 2.5 ng/ml), sucrose (0.4M), brefeldin A (500 μM), chloroquine (50, 10 and 1 μM) and lactacystin (50, 10 and 1 μM). All reagents were purchased from Sigma.

Cytolytic Assay for Immune Splenocytes

Three per group female BALB/C mice were electroporated with plasmid constructs as described above or s.c. immunized with 10 μg $iLR_{58-66}$ peptide/IFA twice with two weeks intervals. Splenocytes were in vitro stimulated with 1 μg $iLR_{58-66}$ peptide or irrelevant MOPC315 peptide in complete RPMI 1640 with IL-2 for one week, then were mixed with target cells ($1\times10^4$), A20 lymphoma, MOPC315 and EL4. The cytotoxicity as lactate dehydrogenase release (LDH) in the cell supernatants was measured using the Cytotoxicity Detection Kit (Roche) following manufacturer's instructions at the sorbance measured at 570 nm with a 630 nm reference filter on a plate reader 680XR (Bio-Rad). The average values for wells performed in triplicate were used for calculations after the medium controls were subtracted. The percent-specific cytotoxicity was calculated as: percent cytotoxicity=(experimental−effector alone)−target spontaneous/target maximum−target spontaneous.

Confocal Microscopy

B6/129 cells ($10^5$) were cultured overnight in covered glass bottom dishes (MatTek Corporation, Ashland, Mass., USA) as described elsewhere[18]. The slides were incubated on ice with 25 μg/ml MIP3α-fusion proteins in 10% FBS/RPMI. After two washes in ice-cold PBS, 10% FBS/RPMI warmed at 37° C. was added and slides were incubated at 37° C. for 0, 10, 30, and 60 minutes before fixation with 3.7% formaldehyde for 10 min and permeabilization with 0.2% Triton X-100 for 5 min at RT. Following primary Abs were used: anti myc mAb (clone 9E10, Sigma), and rabbit anti-LAMP-1 antibody (H-228) or rabbit anti-Clathrin HC (H-300, both from Santa Cruz Inc., Calif., USA), or rabbit anti-proteasome 20S subunit alpha-5 (Affinity BioReagents, Golden, Colo.). The secondary Abs, goat anti-mouse or goat anti-rabbit IgG, were conjugated to Alexa Fluor 488 or Alexa Fluor 568 (Molecular Probes Inc, Oreg., USA). After washing, a drop of Prolong anti-fade reagent (Molecular Probes) was added to each slide well, and images were acquired with a 63× objective on a Zeiss LSM 410 confocal system and processed using Adobe Photoshop.

Mice vaccinated with MIP3α/CCL20 fused with OFA-iLRP display long lasting CD8 T cell-dependent protective responses. Specifically, immune mice rejected challenge with synergetic tumor cells even after 9 months (see FIG. 15A-D).

Results and Discussion

Figure 4:
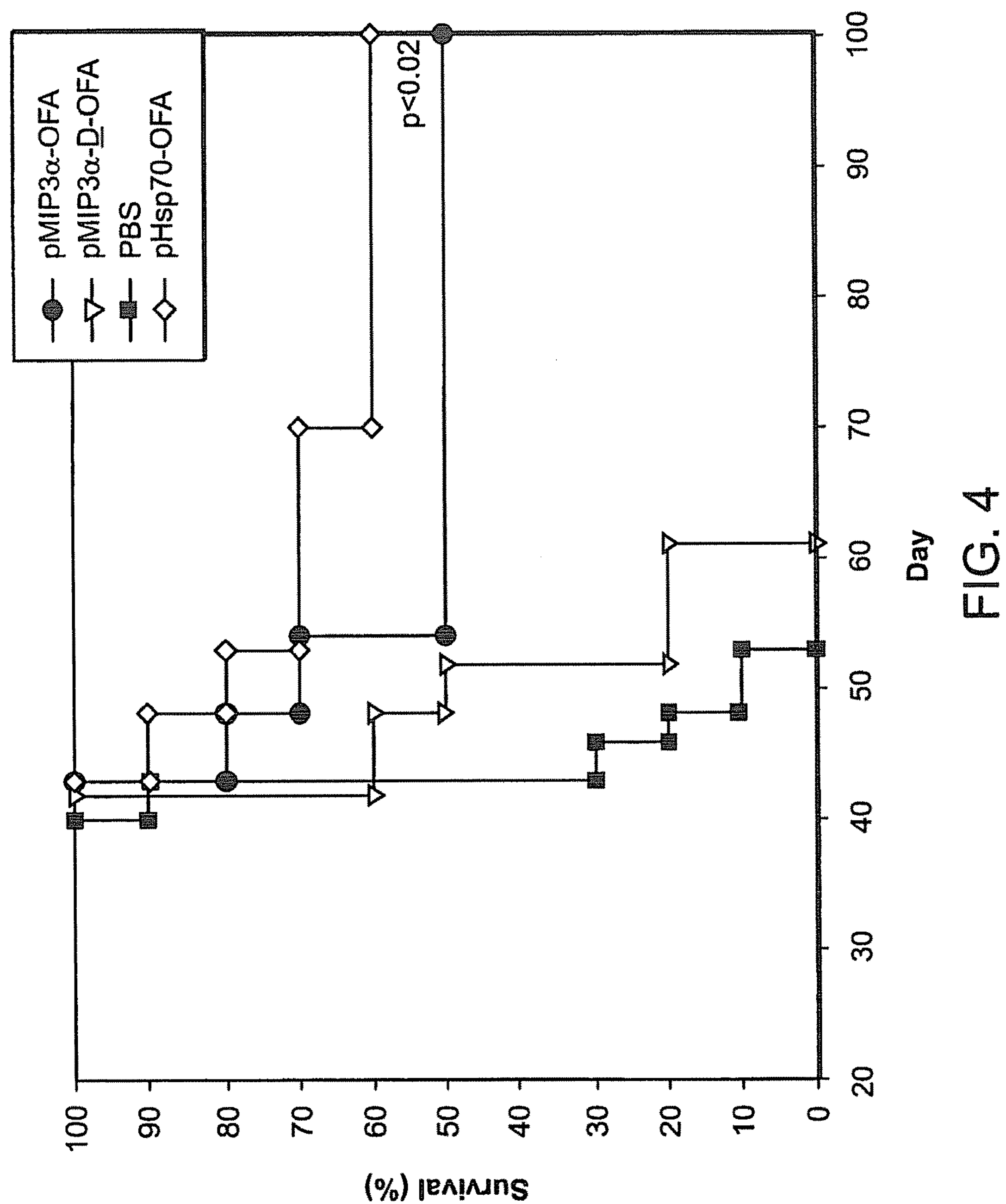
FIG. 4 depicts treatment with pMIP3α-OFA eradicates established A20 lymphoma. BALB/c mice (ten mice per group) bearing A20 lymphoma were treated immunizing with pMIP3α-OFA or pHsp70-OFA. Control mice were mock treated with PBS or electroporated with pMIP3α-D-OFA. Tumor free survival was followed for 100 days post tumor challenge. The data shown is representative of four independent experiments which yielded similar results. P-value refers to comparison with pMIP3α-D-OFA.
Figure 5:
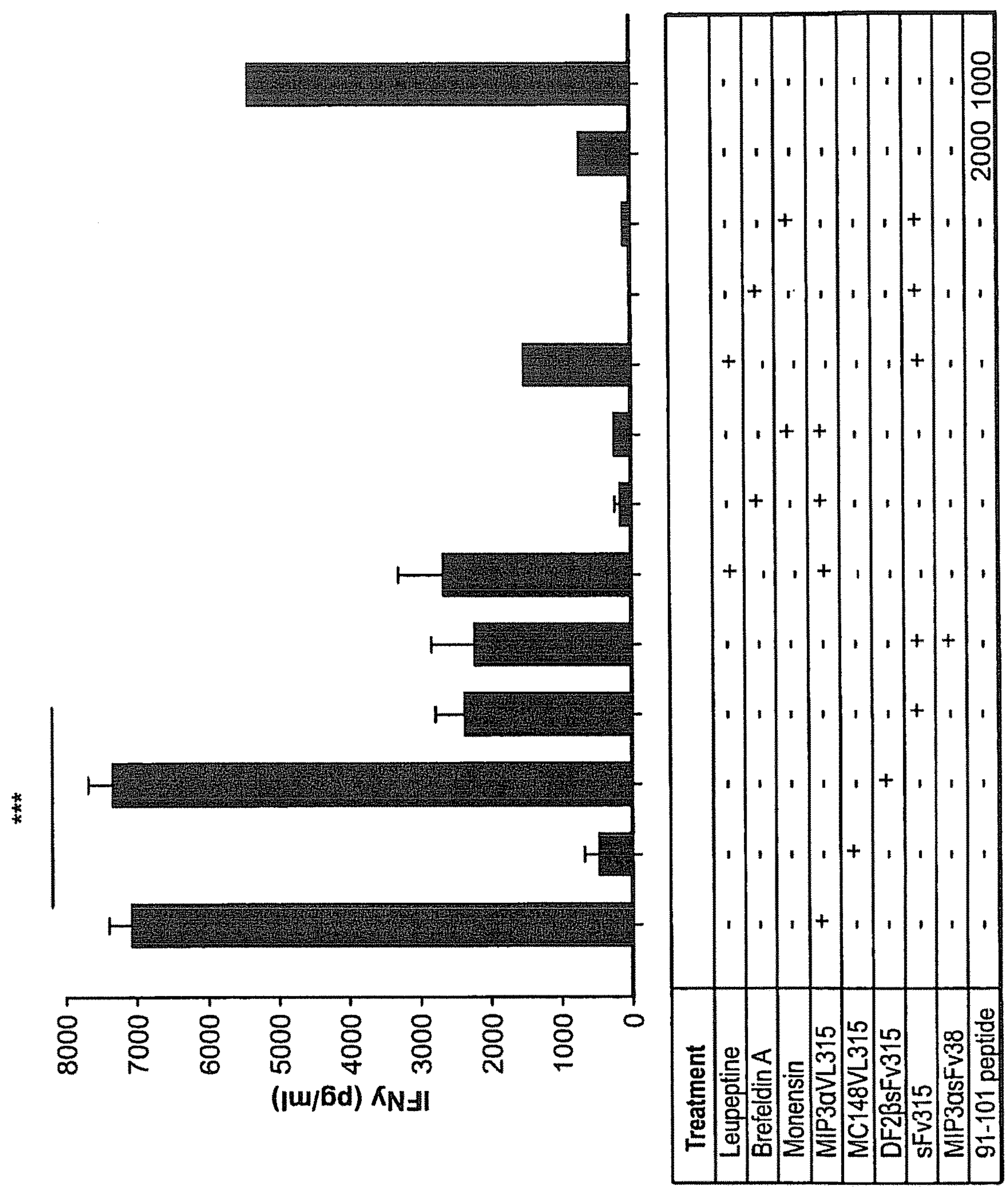
FIG. 5 demonstrates that chemokine or defense fusion proteins are taken up, processed and presented by APCs in vitro via chemokine receptor utilizing MHC class II pathway. Titrated amounts of protein (shown in ng/ml), 91-101 peptide or an irrelevant peptide derived from A20 lymphoma VL chain were incubated with BALB/c mice immature DCs. APCs were then washed, irradiated and placed in culture with epitope-specific 7A10B2 T cell line for 48 hrs, and IFNγ was assayed in culture supernatants. Control treatment groups were immature DCs or matured by overnight treatment with LPS (10 ng/ml) DCs were pulsed with 0.2 μg/ml 91-101 peptide, or with 10 μg/ml irrelevant peptide.
Figure 6A:
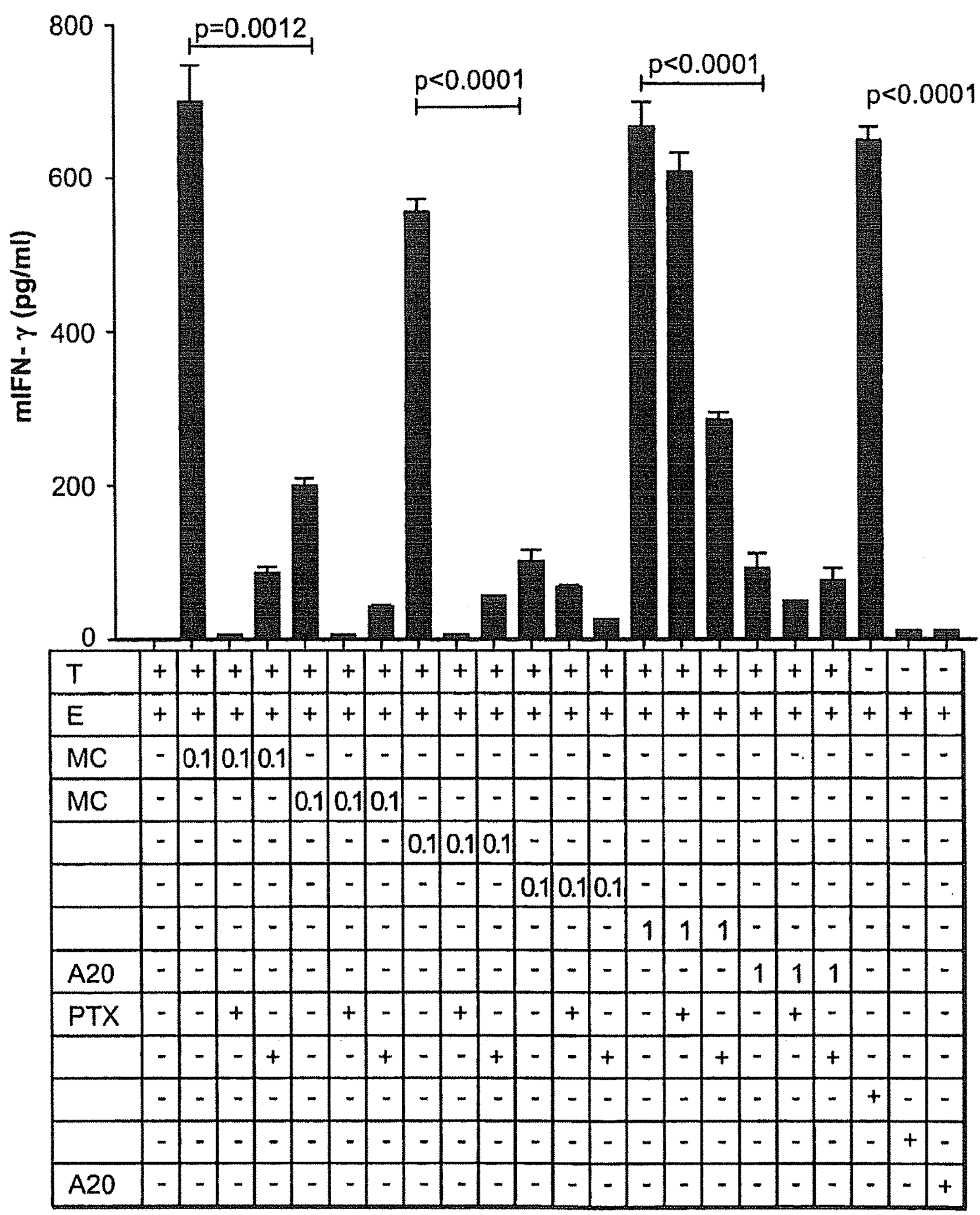
FIGS. 6A-B demonstrate that chemokine fusion enables tumor antigens to be efficiently cross-presented, i.e. processed and presented to MHC class I. The intracellular trafficking of Chemokine receptors is dependent on clathrin-associated vesicles (since inhibited with sucrose) and G-protein signaling (inhibited with peruses toxin, PTX) (A). Specificity of effector cells was tested on iDC pulsed with $hgp100_{25-33}$ peptide, or control A20 peptide, or mixing with cells such as B16 melanoma ($H-2^{b}$), EL4 ($H-2^{b}$), and A20 ($H-2^{d}$). iDC were treated with 0.1 μg/ml chemokine proteins fused with gp100 in the presence or absence of various pharmacological inhibitors (μM) of intracellular organelle trafficking, such as leupeptin and chloroquine (for endosomal-lysosomal), or brefeldin A (vesicle transport between the ER and Golgi). Titrated doses of lactacystin (a specific proteasomal inhibitor, shown in μM), a used to test for cytosolic processing (B).
Figure 6B:
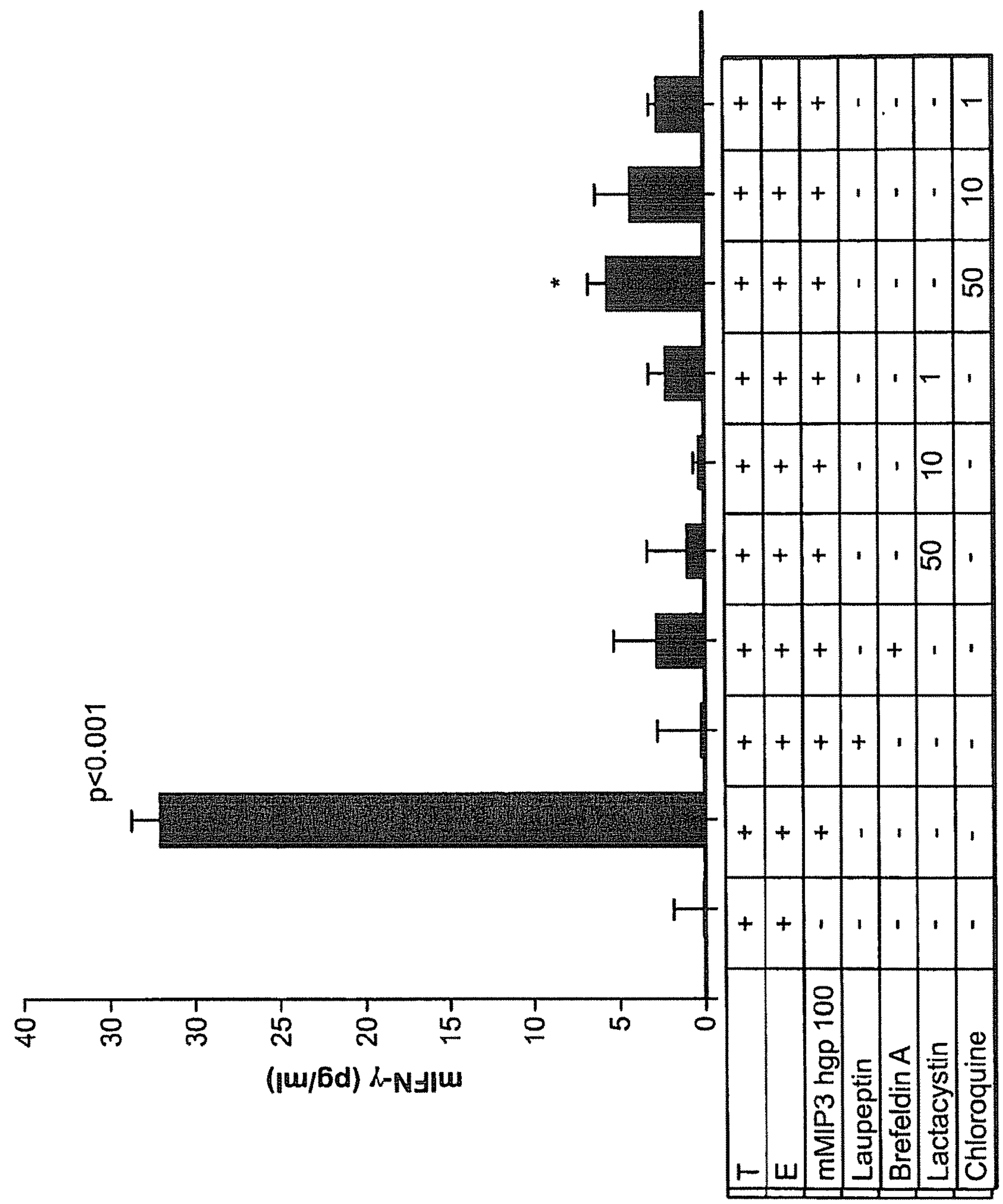
Figure 7:
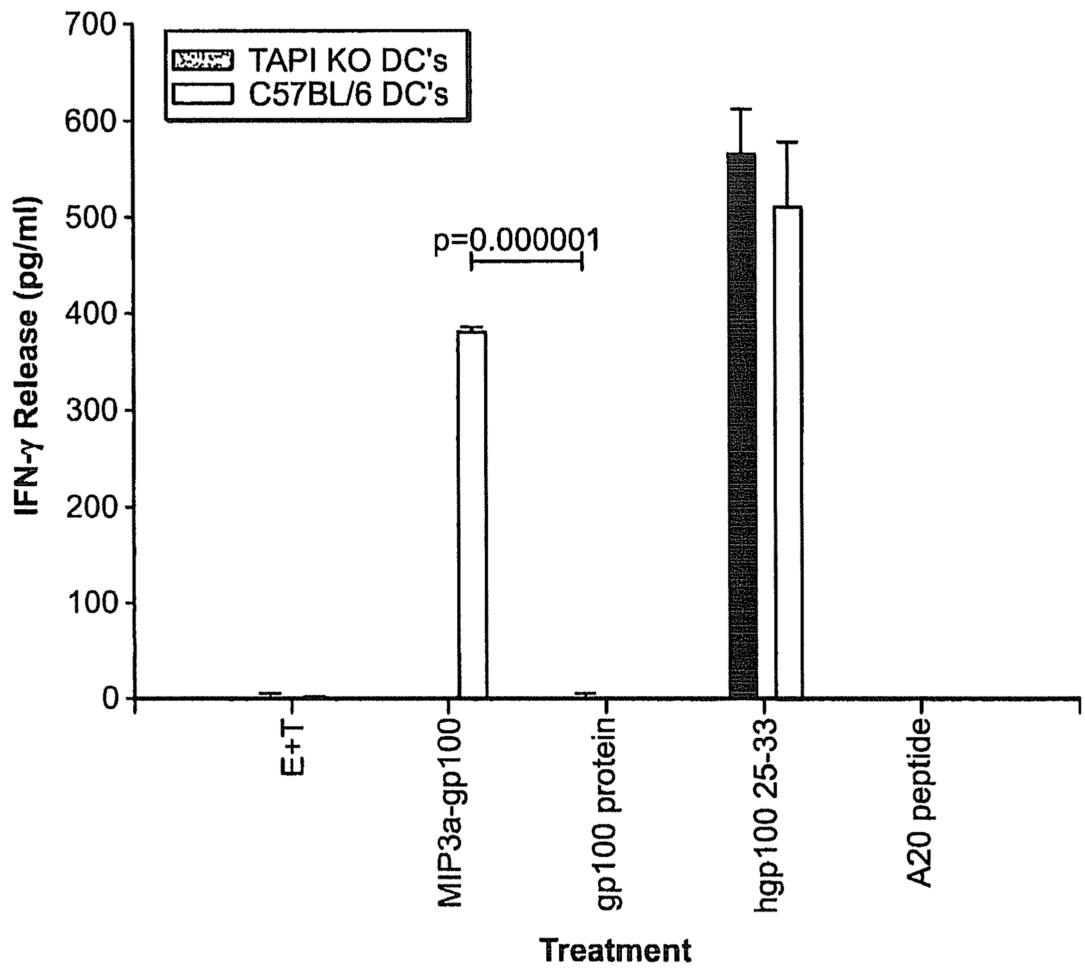
FIG. 7 demonstrates that cross-presentation of chemokine fusion vaccines requires TAP-1 machinery. Immature DC derived from TAP-1 knockout (TAP KO) or wild type C57BL/6 mice were incubated with 0.1 μg/ml either MIP3α-gp100 or the gp100 protein alone and tested for their ability to stimulate gp 100-specific T cells derived from pmel-1 mice, as described. Control APC were treated with the active gp 100 peptide, $hgp100_{25-33}$, or irrelevant A20 peptides. IFN-γ release was measured in the supernatants of cells cultured for 24 hours by ELISA.
Figure 8:
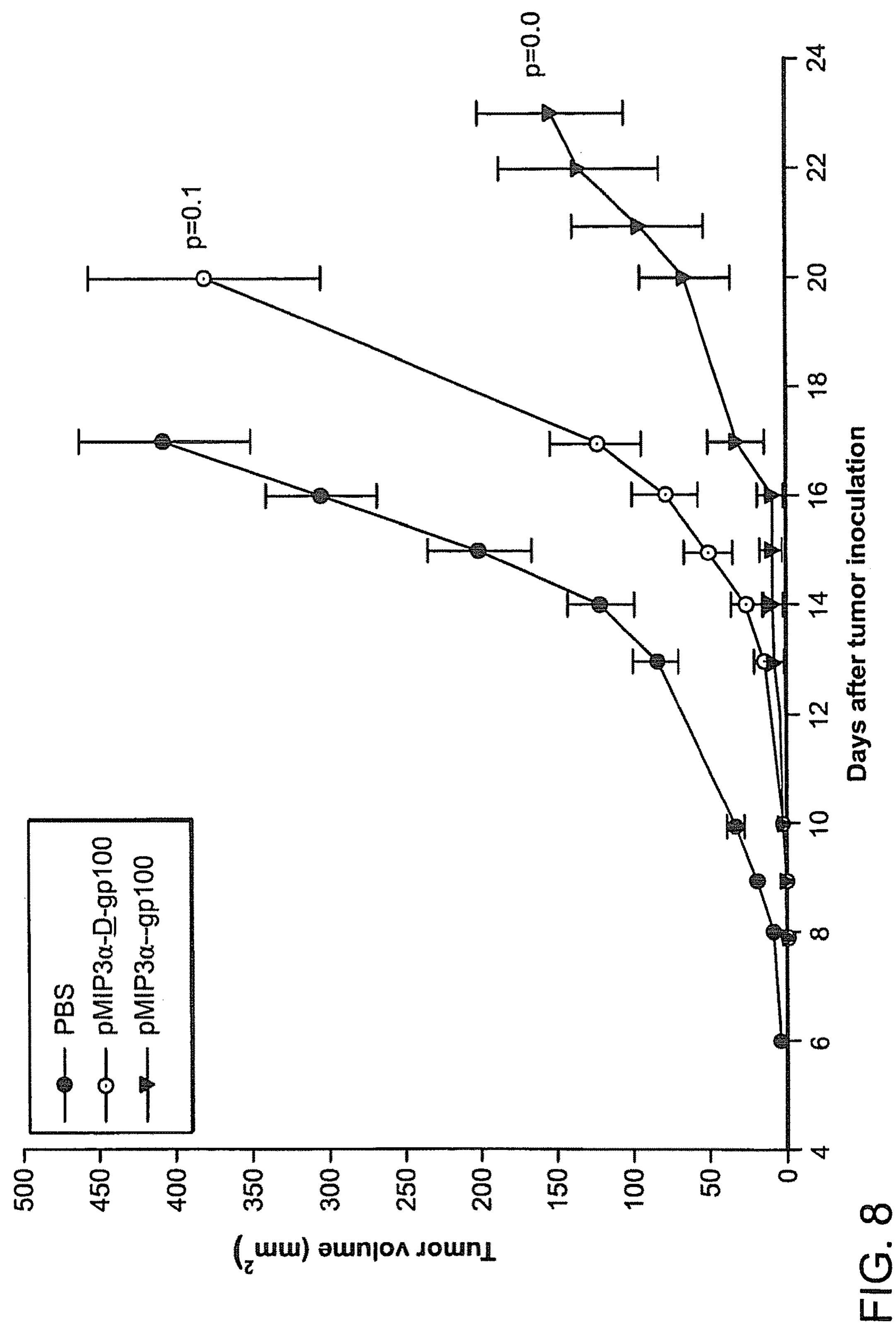
FIG. 8 demonstrates that chemokine fusion vaccination elicits protective anti-tumor responses in C57BL/6 mice. Ten mice per group were gene-gun immunized three times with pMIP3α-gp100, pMIP3α-D-gp100 (a fusion with a mutated MIP3α which can not bind to CCR6) or PBS. Two weeks after the last immunization, mice were challenged s.c. with a lethal dose of B16 tumor cells. Tumor growth suppression was subsequently assessed and mice with tumor greater than 400 $mm^2$ were euthanized. The data shown is representative of two independent experiments which yielded similar results. P-value is 0.02.
Figure 9:
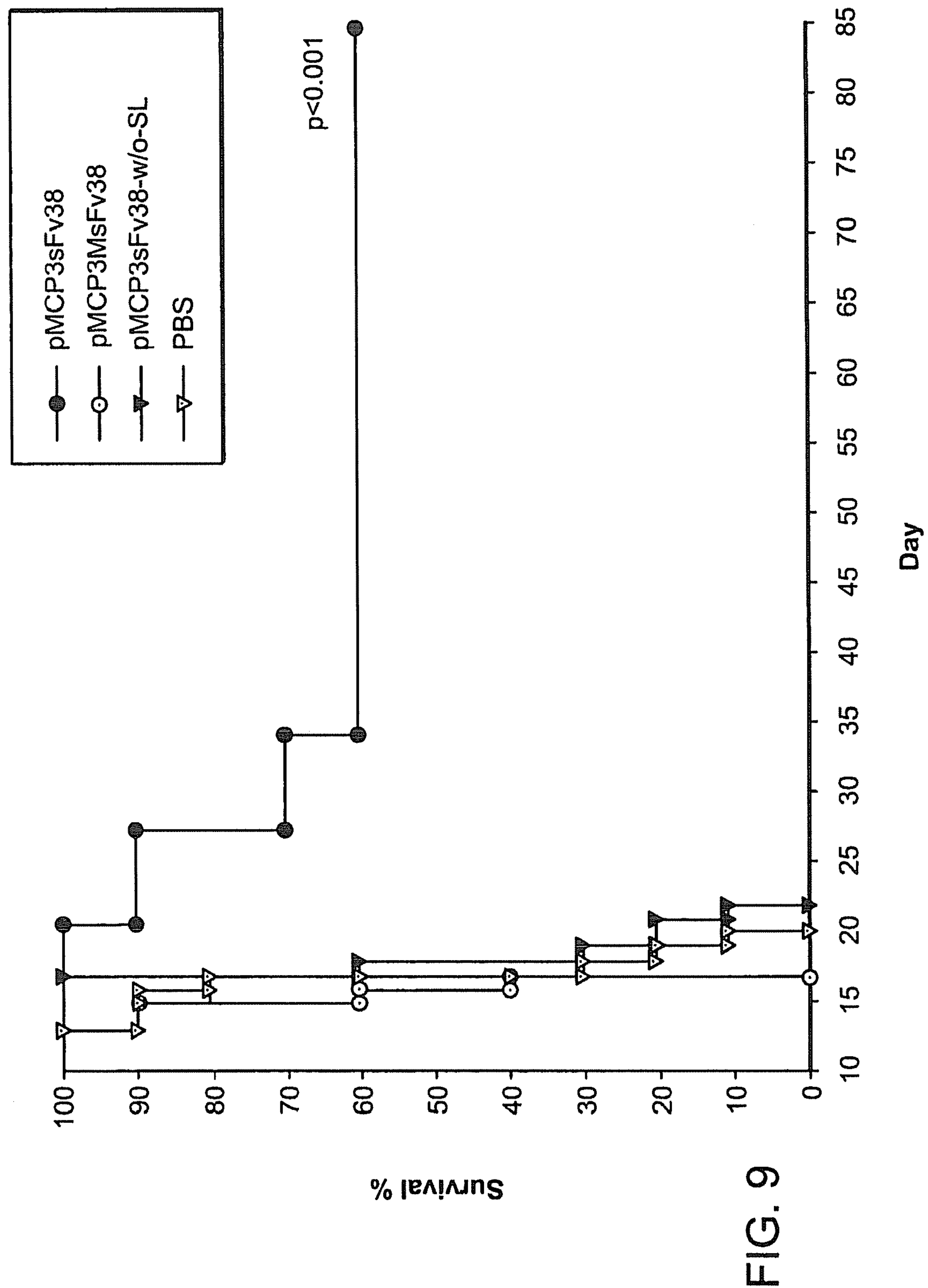
FIG. 9 demonstrates that tumor protection requires secretion of chemotactic fusion protein FIGS. 10A-10B demonstrate that antibody responses to the same antigen depend on a type of chemokine used. Mice were gene gun immunized with DNA constructs expressing non-immunogenic tumor antigen (sFv38) fused with various chemokines.
Figure 10A:
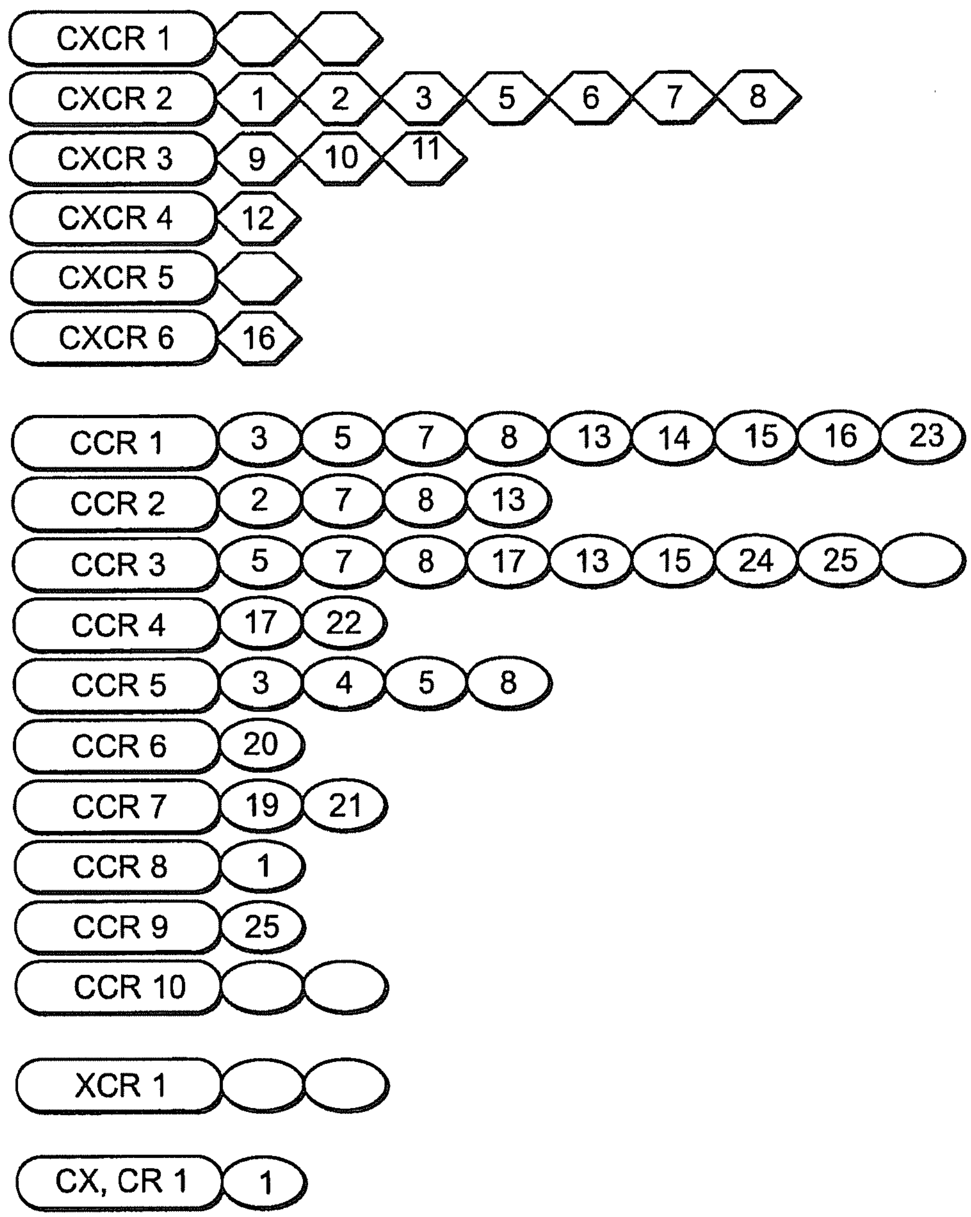
Figure 10B:
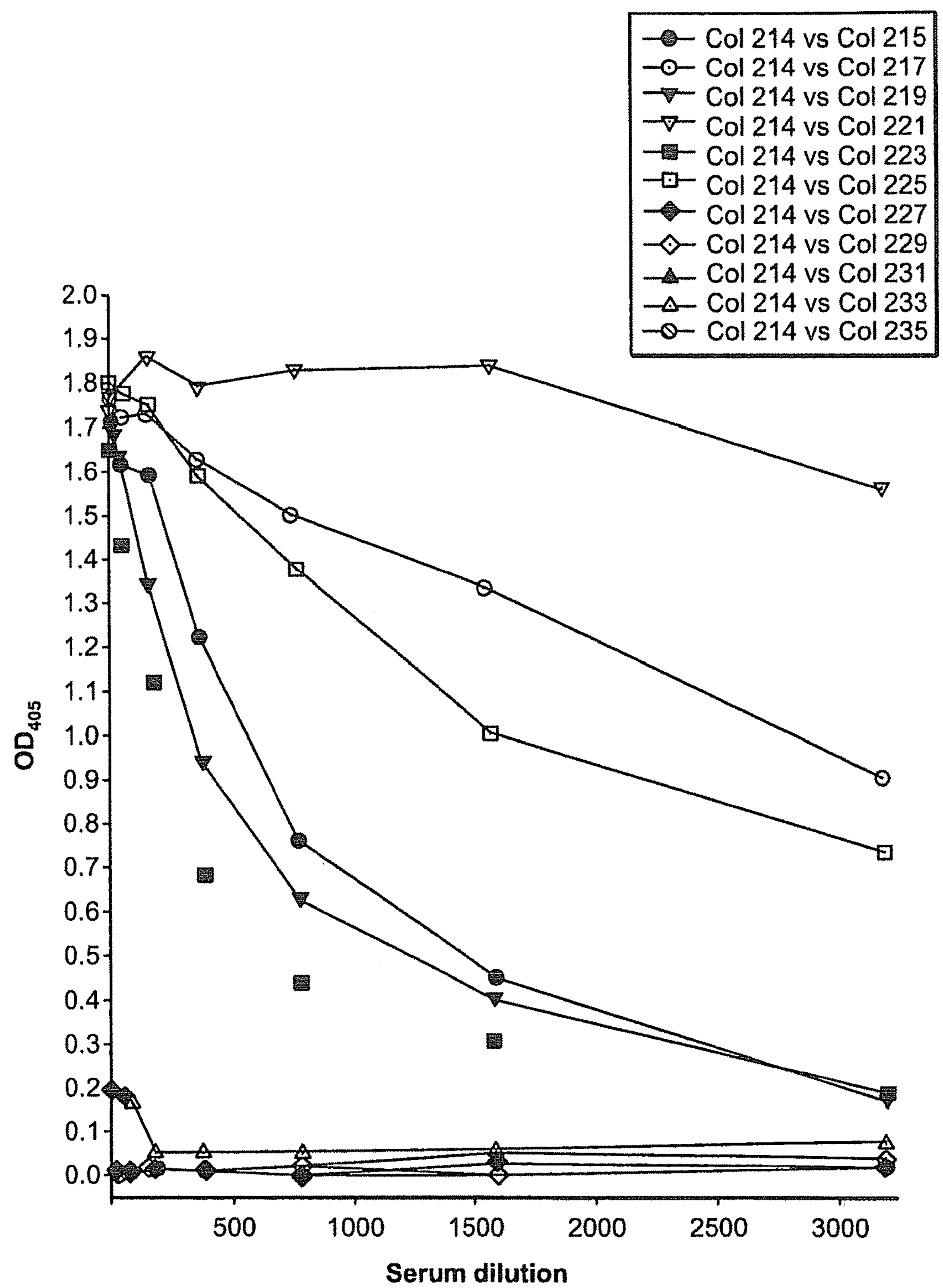
Figure 11A:
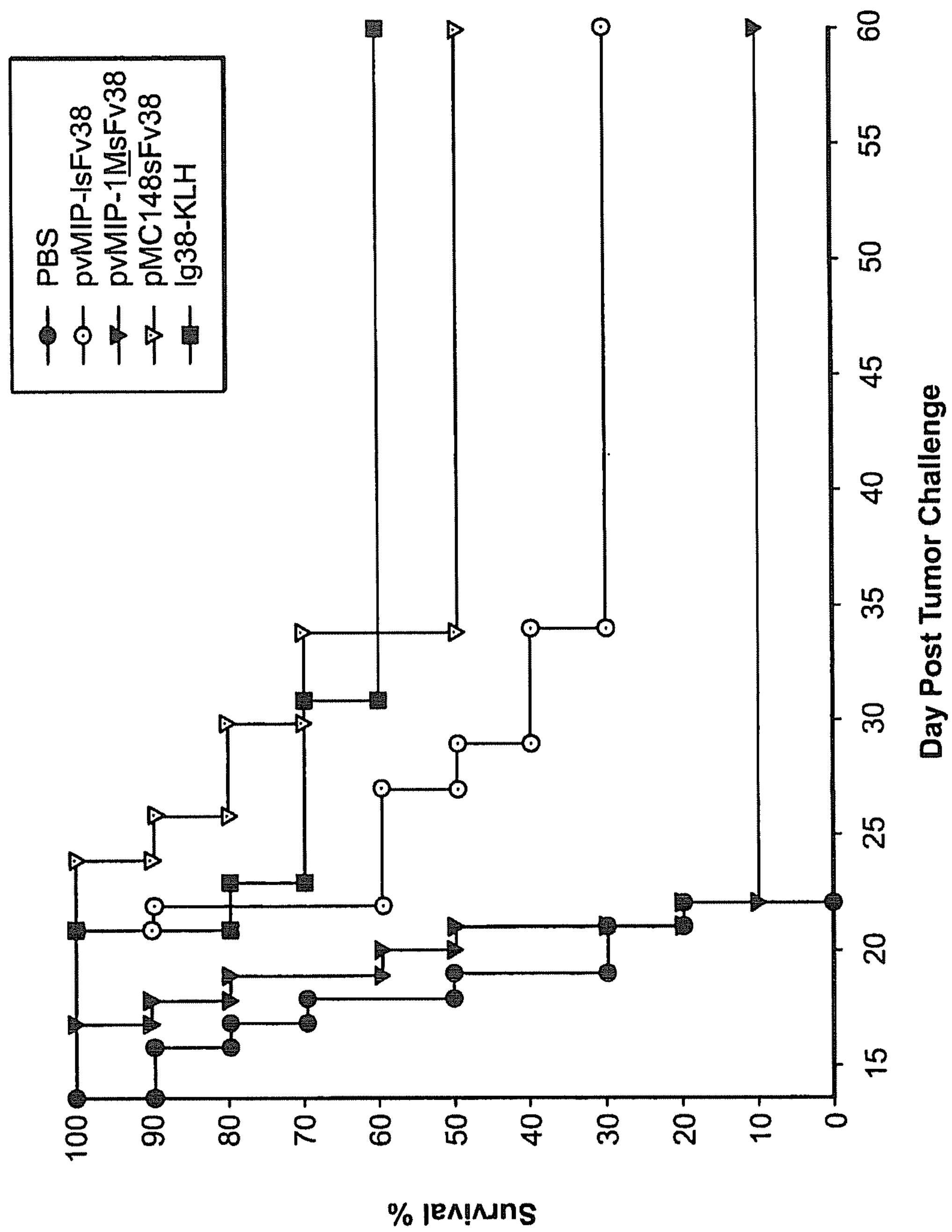
FIGS. 11A-B demonstrate that immunizations with viral chemokine carriers induce antitumor protection. Ten per group C3H mice were gene gun with plasmids indicated immunized three times in every two weeks, and two after, mice were i.p. challenged with 10× lethal dose (3000 cells) of 38C13.
Figure 11B:
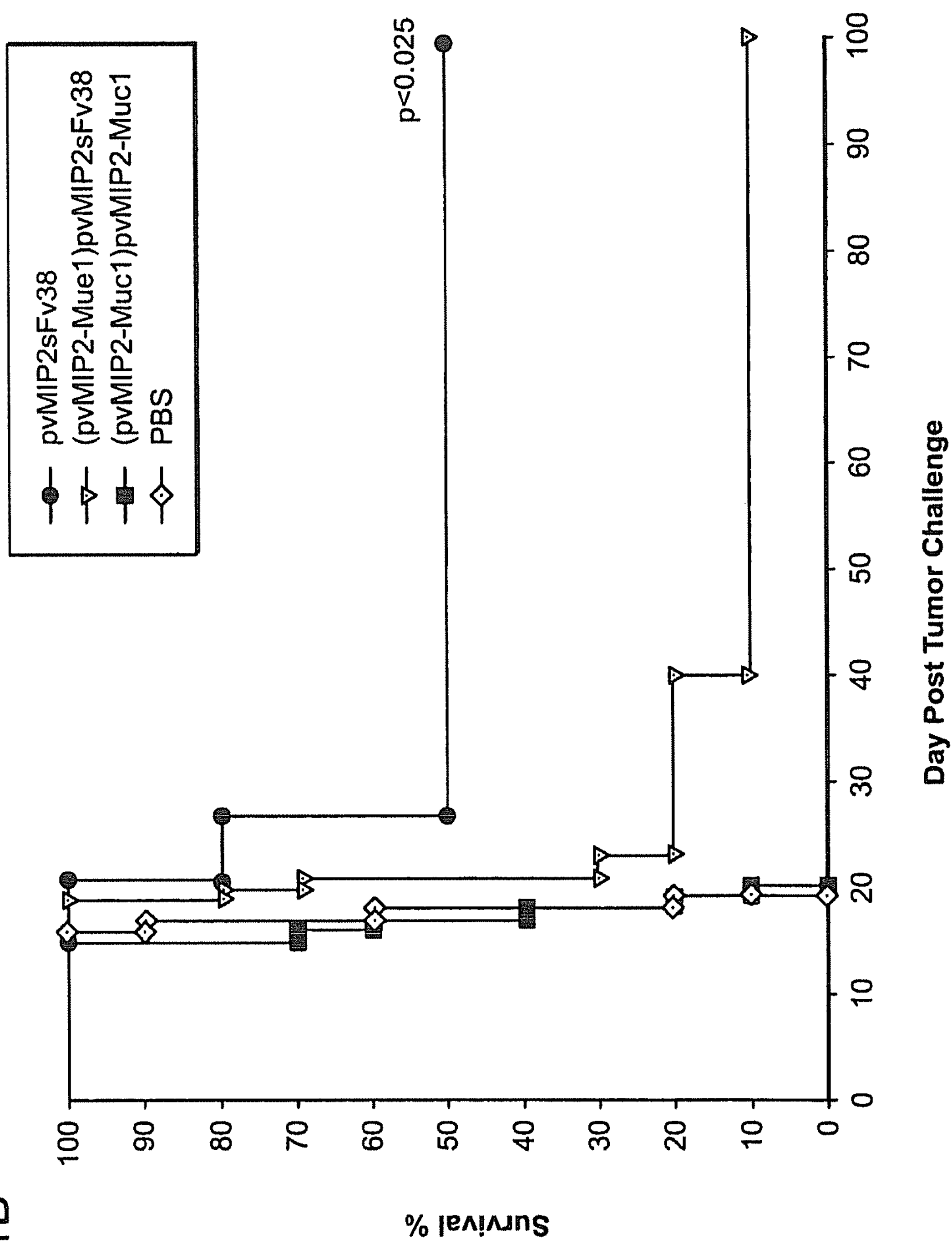
Figure 12A:
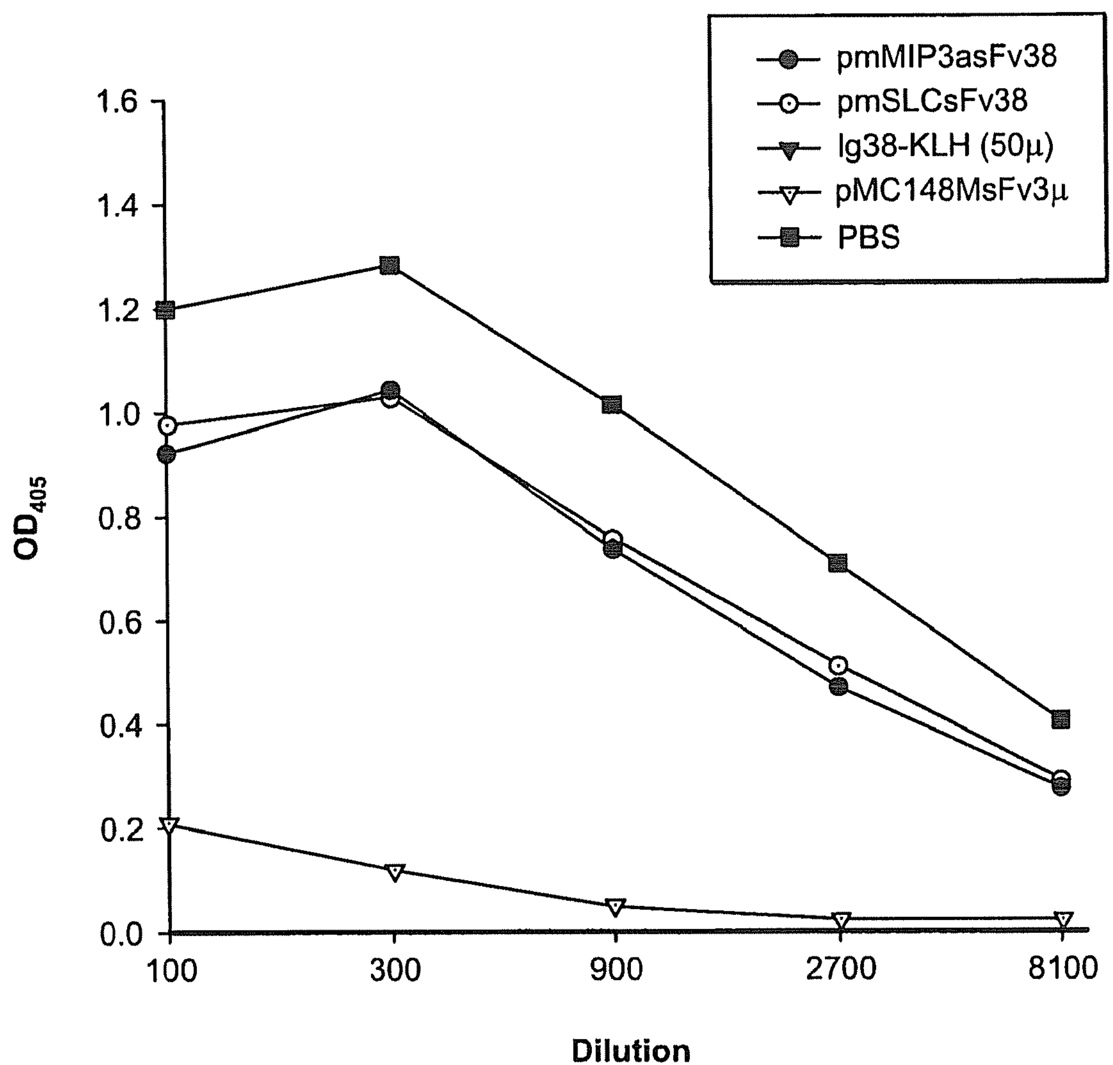
FIGS. 12A-B depict the results of experiments demonstrating CCR6 vs. CCR7: MIP3α fusion constructs elicit antitumor protection, although both SLC and MIP3α fusions generate anti-Id Abs.
Figure 12B:
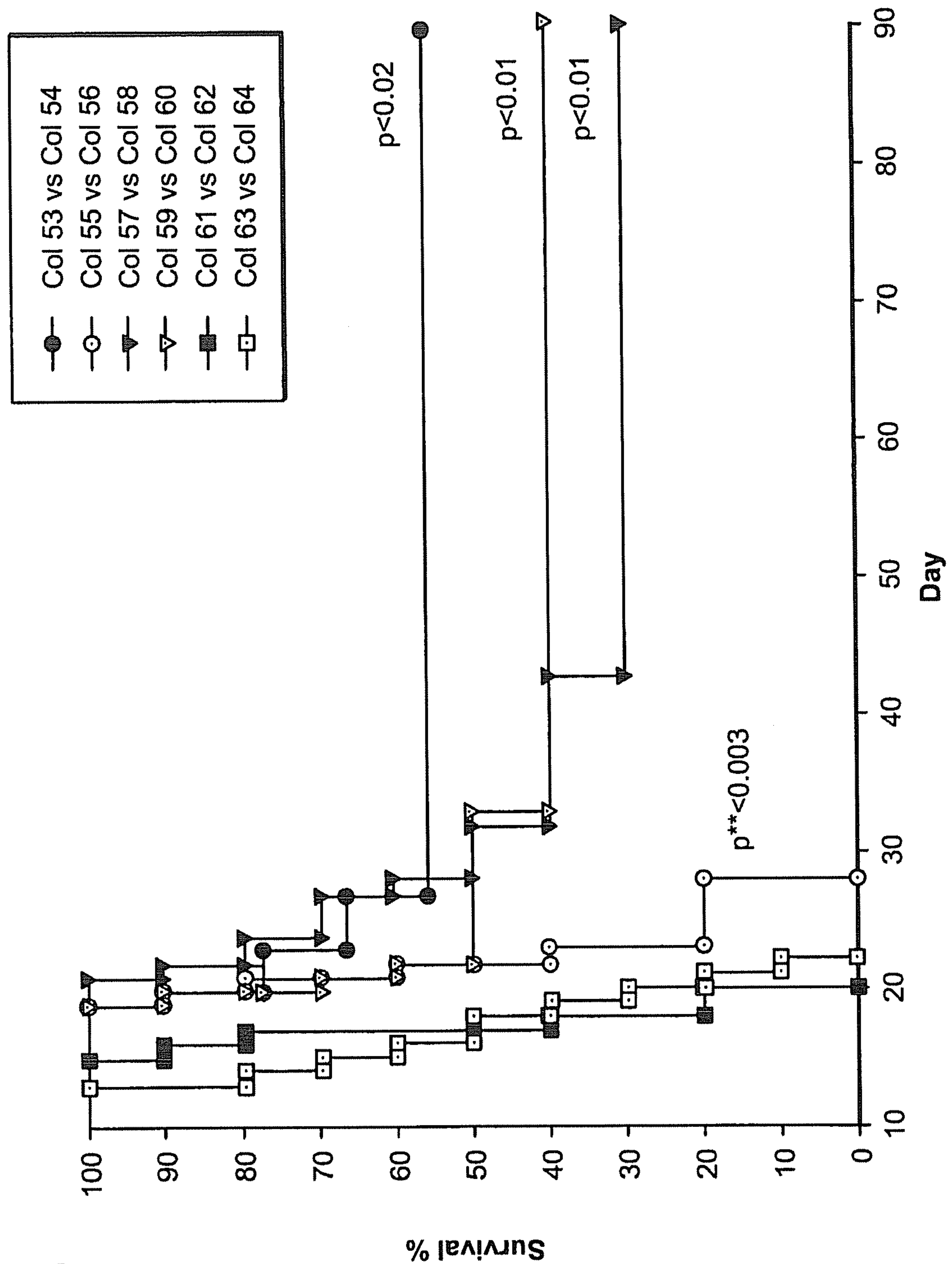
Figure 13:
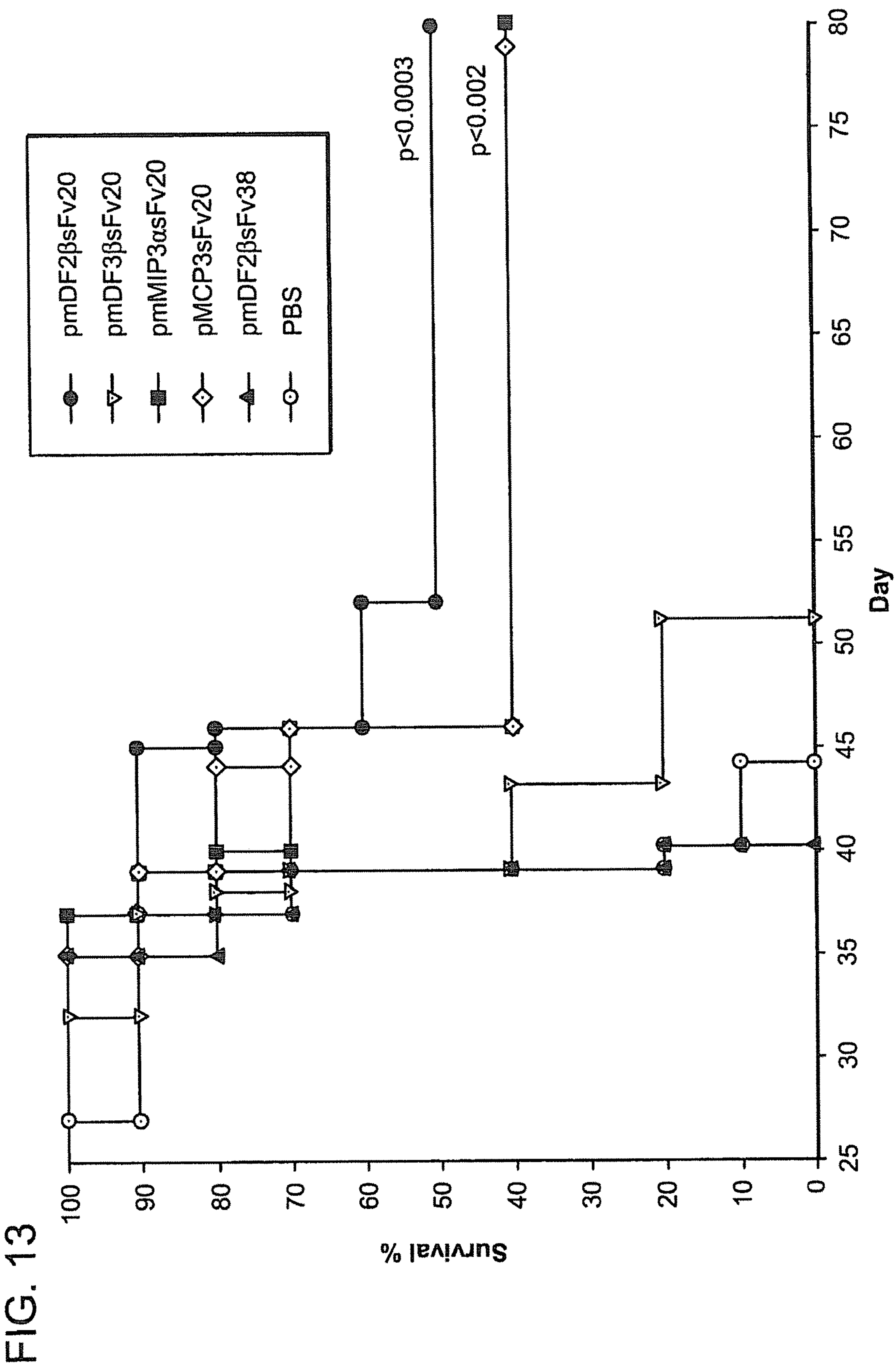
FIG. 13 demonstrates that injection of plasmid DNA encoding iDC chemo-attractant fusions elicit therapeutic antitumor immunity.
Figure 15A:
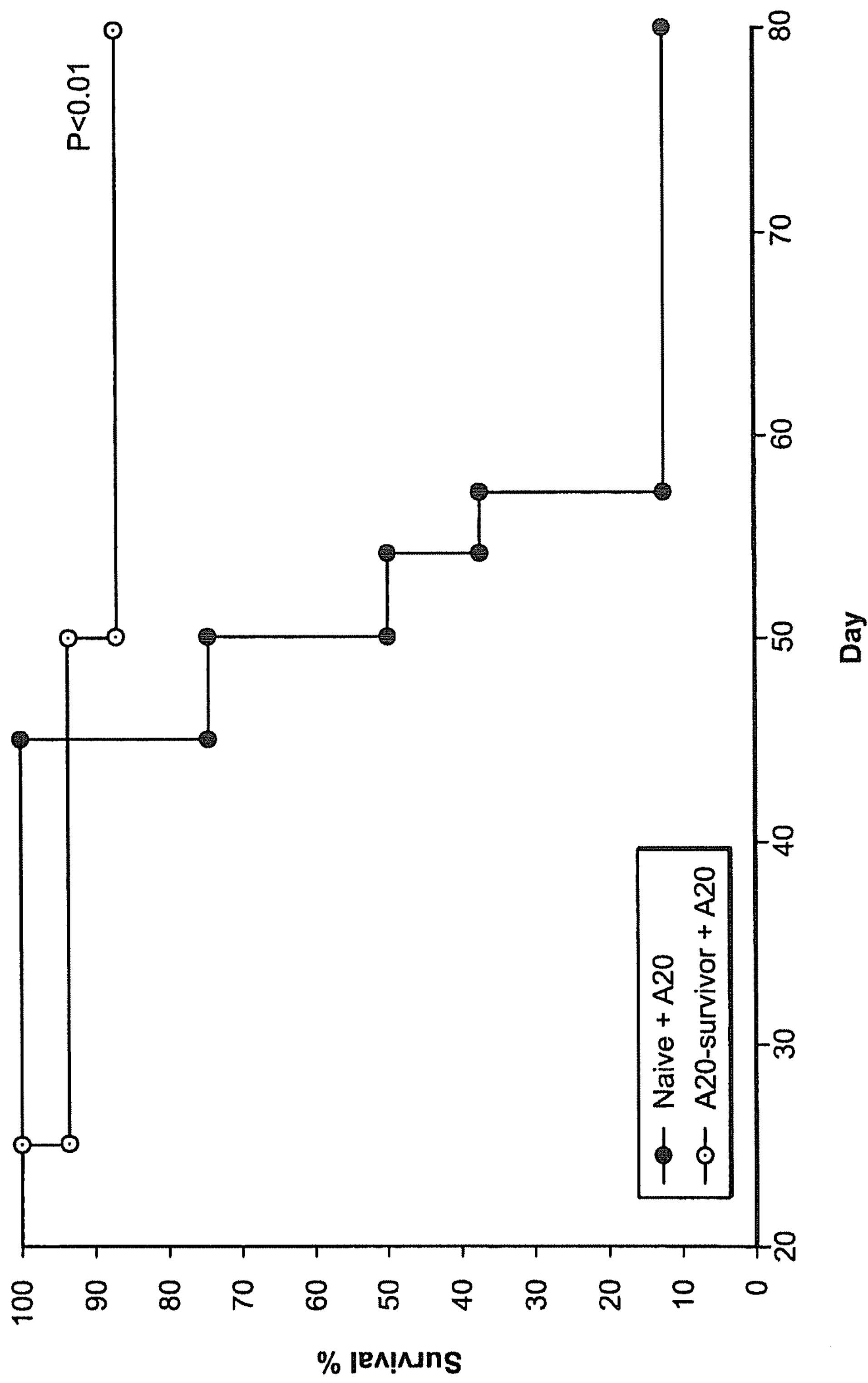
FIGS. 15A-D depict eradication of A20 lymphoma promote long-term T cell-mediated memory that protects mice from re-challenge with A20 lymphoma. (A) sixteen mice that were free of tumors for about 9 months (open circles) and control ten age-matched naïve BALB/C mice (closed circles) were challenged with A20 lymphoma cells. P-value refers to comparison with control mice. (B) In parallel, splenocytes of long-term survivor mice (E, effector cells) were in vitro stimulated for one week on DCs pused with OFA-peptide and tested against target cells (T), such as A20, 4T 1, and B 16 tumors, at indicated ration (T:E). Shown, percentage of cytotoxicity (Y-axis) of a representative experiment performed in triplicate. (C) OFA-iLRP is expressed on the surface of A20 lymphoma and B16 melanoma cells, but not 4T1 tumor cells. OFA expression was determined with Alexa-488-conjugated anti-OFA mAB (bold lines) vs. control Alexa-488-conjugated isotype-matched AB. (D) Mice that survived A20 tumor challenge (A20-survivor+4T1, see also A) or control BALB/c mice (HBs+4T1) immunized with control constructs expressing HbsAg were re-challenged with 4T1 tumor cells.
Figure 15B:
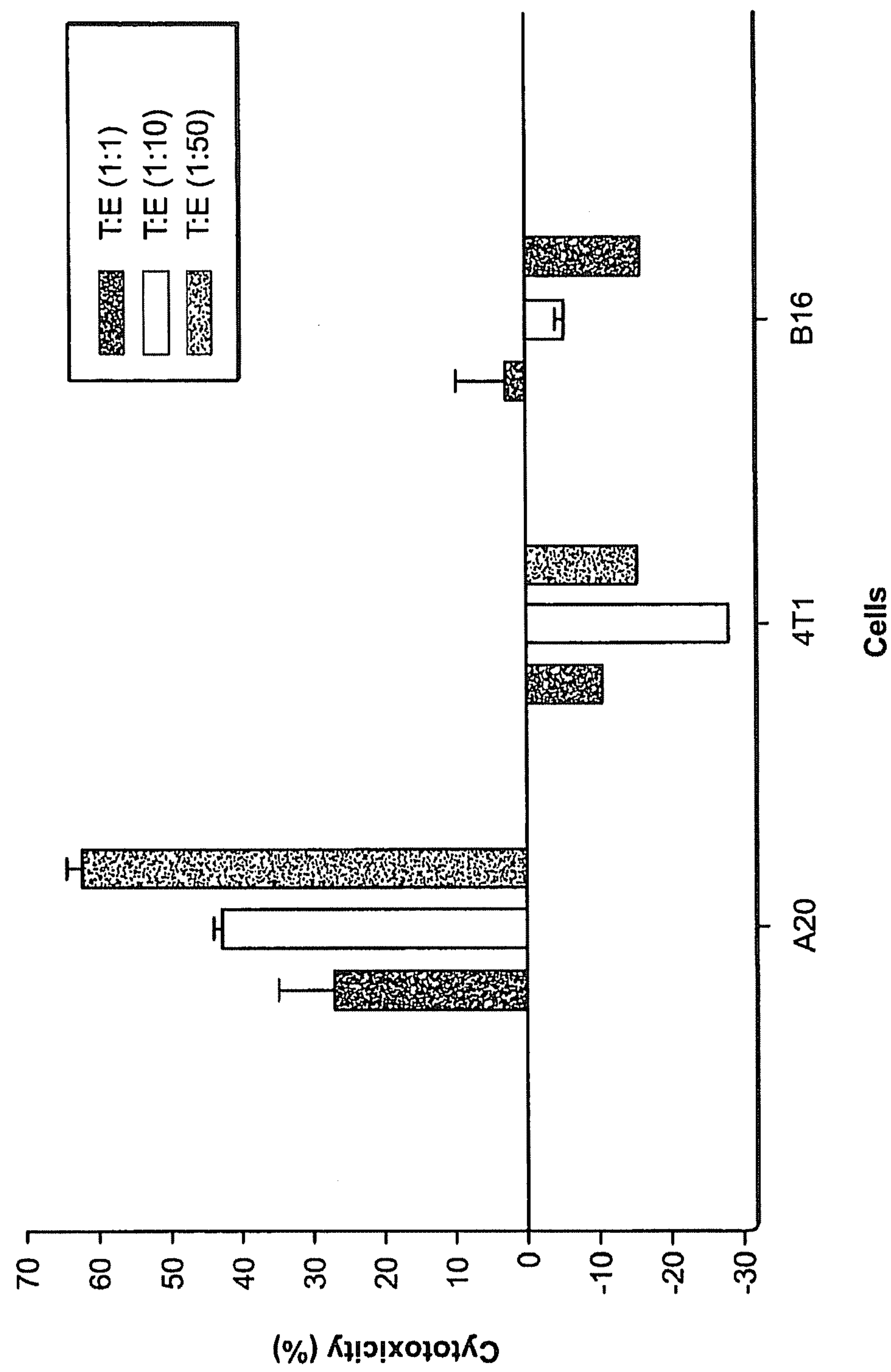
Figure 15C:
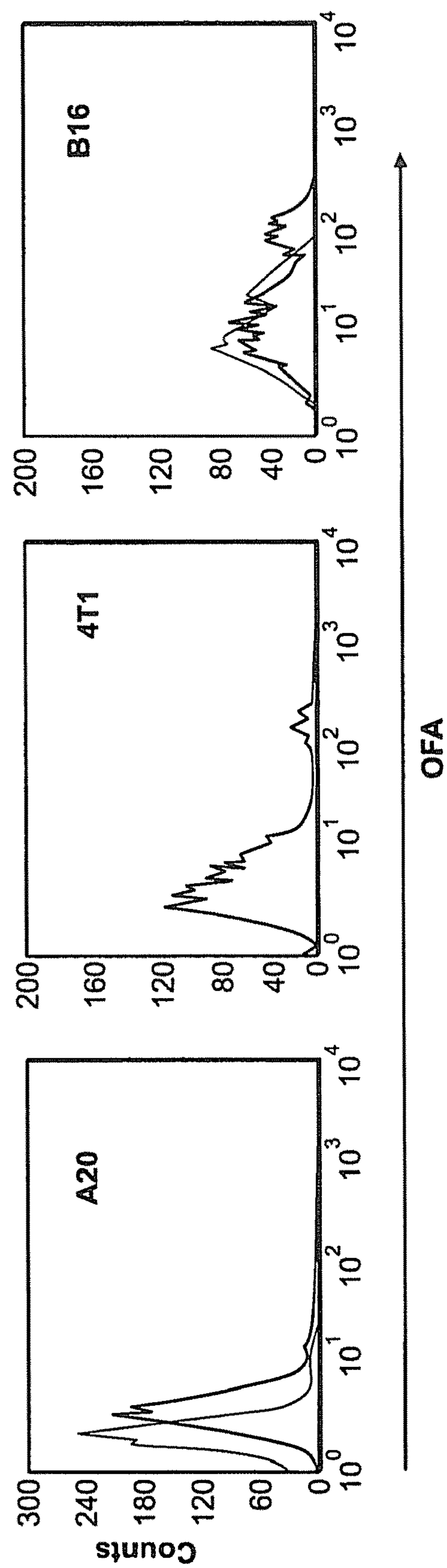
Figure 15D:
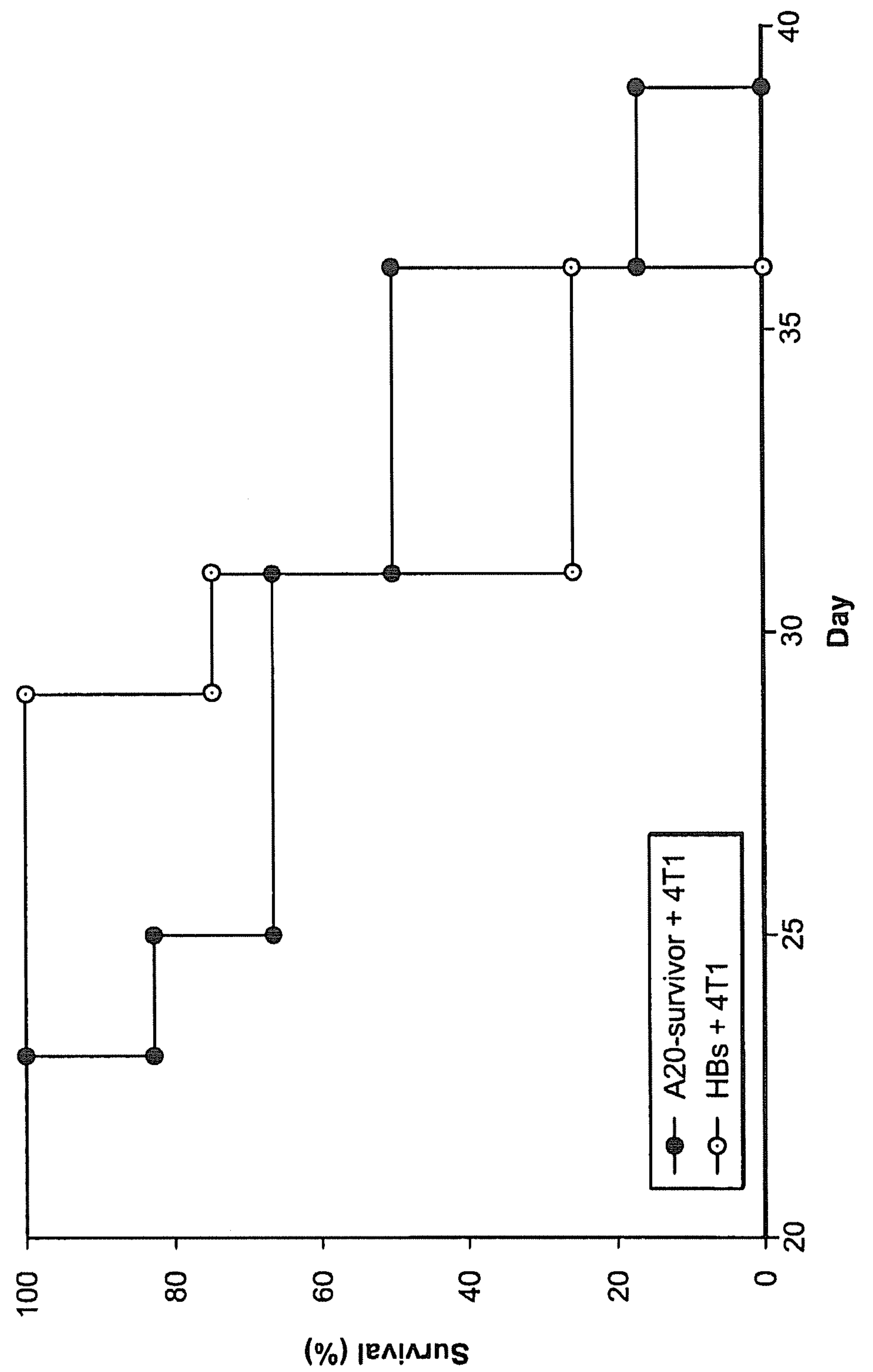

DNA vaccines expressing OFA fused to chemo-attractants elicit potent anti-A20 lymphoma protection. Embryonic antigen OFA-iLRP (OFA) is an attractive target for cancer immunotherapy, as it is abundantly expressed in various malignancies, including murine A20 lymphoma, and not found in normal adult tissues[1]. Initial attempts to induce anti-A20 lymphoma responses in nave BALB/C mice immunized with plasmid DNA expressing OFA failed, due to poor immunogenicity of the antigen. Therefore, to render OFA immunogenic through the CCR6-mediated targeting of iDCs, constructs which expressed OFA fusions with mDF2β (pmDF2β-OFA) or MIP3α/CCL20 (pMIP3α-OFA) were generated. Ten per group naïve BALB/C mice were immunized with either pmDF2β-OFA or with pmDF2β-sFv20, a positive control construct that encoded mDF2β fusion to A20-specific Ig fragment (single chain Fv) shown to be immunogenic[9]. Then, two weeks after the last immunization, mice were challenged with a lethal dose of A20 lymphoma cells. Almost all mice mock immunized with PBS succumbed to cancer (PBS, FIG. 1*a*). In contrast, mice immunized with pmDF2β-OFA or pmDF2β-sFv20 acquired significant protection against A20 lymphoma ($p<0.05$, as compared with PBS treated mice, FIG. 1*a*). The response required targeting of CCR6, as control vaccines that expressed OFA fused to mutant MIP3α, which did not bind CCR6 due to a single point mutation[11], failed to protect (pMIP3α-D-OFA, see FIG. 4). Thus, pmDF2β-OFA is as potent as the Id vaccine (pmDF2β-sFv20) and induces comparable protective anti-B cell lymphoma responses. However, unlike Id, OFA-based vaccines would not require individual formulations for each patient; instead, they might be used for the treatment of any OFA-expressing cancers.

Tumor protection is not improved by use of multiple TAA-encoding vaccines. Since either of the vaccines that expressed different tumor antigens, pmDF2β-sFv20 or pMIP3α-OFA, elicited comparable responses, we tested whether they would also act additively when used together (pmDF2P-sFv20+pMIP3α-OFA). As shown in FIG. 1*a*, mice were protected against A20 lymphoma at almost the same level regardless of whether they were immunized with the vaccine mixture or with a single antigen-expressing vaccine (see pmDF2β-sFv20+pMIP3α-OFA vs. pmDF2β-OFA or pmDF2β-sFv20, FIG. 1*a*). Thus, immune responses elicited against a single TAA can be sufficiently high to protect against tumors, and use of additional antigens may not be necessary or beneficial.

Figure 1B:
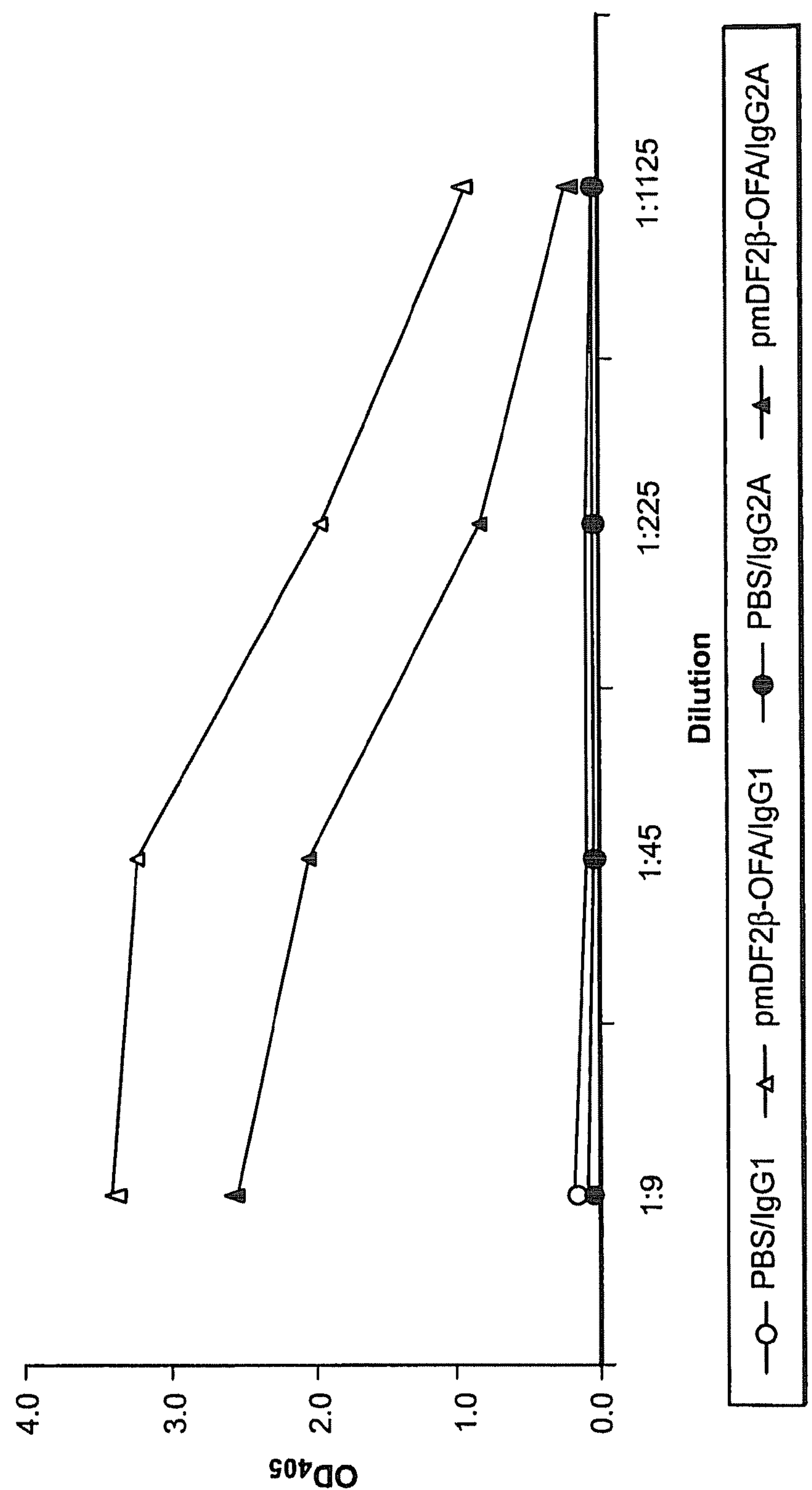
Figure 2A:
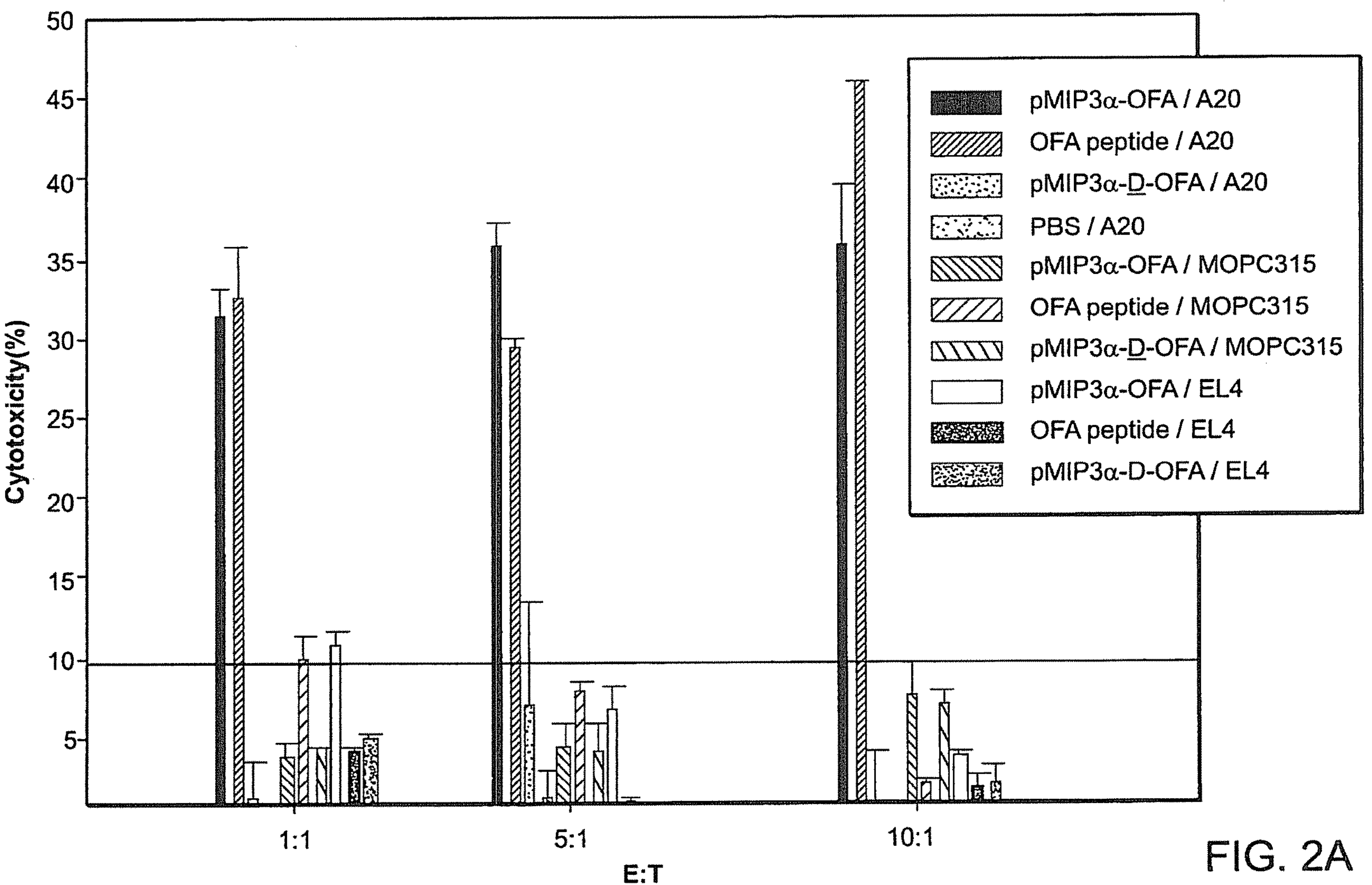
FIGS. 2A-B demonstrate that vaccine induces a T cell response. (A) Splenocytes from mice immunized with pMIP3α-OFA or with the $iLR_{58-66}$ peptide/IFA specifically lyse A20 lymphoma cells (pMIP3α-OFA/A20 and OFA peptide/A20), but not HLA-matched ($H\text{-}2K^d$) but $OFA^-$ MOPC315 (pMIP3α-OFA/MOPC315 and OFA peptide/MOPC315, or mismatched ($H\text{-}2^b$) EL-4 (pMIP3α-OFA and OFA peptide/EL4) tumor cells. Control splenocytes from mice injected with PBS or immunized with OFA fusions with a mutant MIP3α (pMIP3α-D-OFA), which could not bind CCR6, failed to lyse either of cells. Shown here is percentage of cytotoxicity (Y-axis) of two representative and independent experiments with similar results, performed in triplicates. X-axis is effector:target ratio (E:T) of cells used. (B) Tumor protection requires presence of the OFA-specific effector $CD8^+$ T cells. Mice were immunized with pMIP3α-OFA plasmid as above and randomly allocated (ten per group) to treatment with anti-CD8 mAb GK2.43, anti-CD4 mAb GK1.5, or normal rat IgG. P-values refer to comparison between anti-CD8 mAb and IgG injected groups. Flow cytometry analysis of splenocytes from normal mice treated with these mAb in parallel one and two weeks after treatment confirmed a >90% depletion of the appropriate subset with normal levels of the other subset (data not shown).
Figure 2B:
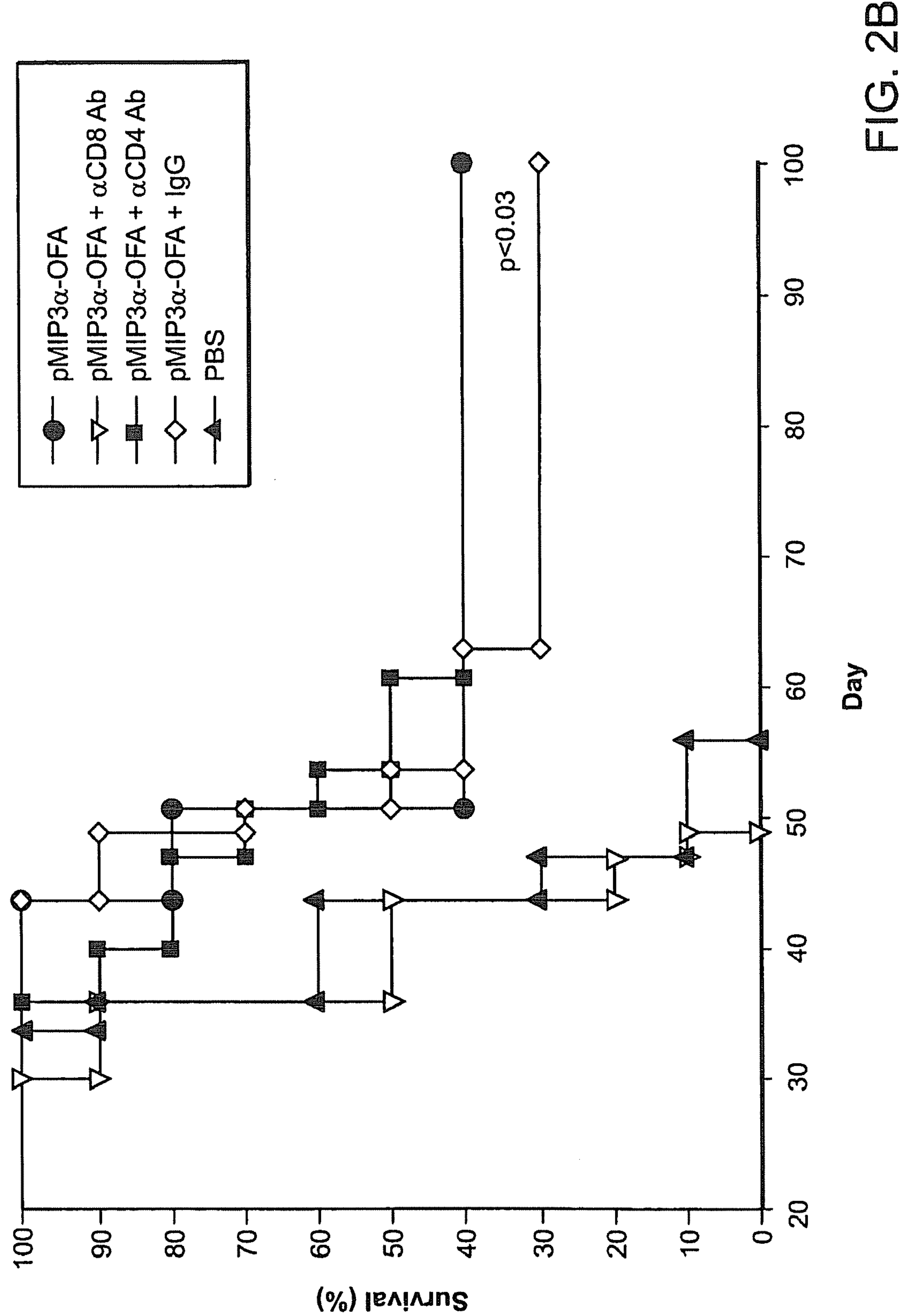

Tumor protection depends on induction of effector $CD8^+$ T cells. Mice immunized with pmDF2β-OFA or pMIP3α-OFA generated not only OFA-specific IgG1 antibodies (open triangle, FIG. 1*b*), but also significant levels of IgG2a antibody (closed triangle, FIG. 1*b*), indicating that they might produce Th1 responses[19]. Moreover, mice immunized with the vaccines generated cytolytic T cells (CTLs) capable of specific killing of A20 tumor cells in vitro (FIG. 2*a*). The CTLs were specific to OFA, as they did not lyse irrelevant HLA-matched MOPC315 cells, which did not express OFA (FIG. 2*a*). The response was dependent on the ability of the vaccine to target CCR6, since splenocytes from mice immunized with the construct expressing OFA fused to a mutant MIP3α (pMIP3α-D-OFA, FIG. 2*a*) did not kill A20 lymphoma cells. Since mice immunized with pMIP3α-D-OFA were also not protected (FIG. 4), it is tempting to speculate that the protection was mediated by these CTLs. To study this, $CD8^+$ or $CD4^+$ effector cells were depleted in mice immunized with pMIP3α-OFA by injecting specific antibodies prior to the challenge with A20 lymphoma cells. Injections of isotype-matched irrelevant IgG (pMIP3α-OFA+IgG, FIG. 2*b*), or the depletion of effector $CD4^+$ T cells (pMIP3α-OFA+αCD4 Ab, FIG. 2*b*) did not have any effects and mice immunized with pMIP3α-OFA remained protected. In contrast, the protection was completely abolished in mice that were depleted of effector $CD8^+$ T cells (pMIP3α-OFA+αCD8 Ab, FIG. 2*b*). Taken together, these data clearly indicate that, as we also reported for Id-mediated anticancer protection[9], the protection was primarily dependent on the activation of cellular immunity, particularly effector $CD8^+$ T cells, but not humoral responses despite the fact that both Id and OFA-iLRP are expressed on the cell surface. Thus, the breadth of the CCR6-targeting chemoattractant-based OFA vaccines is in their ability to elicit tumor-specific $CD8^+$ cytolytic T cell responses.

Figure 3A:
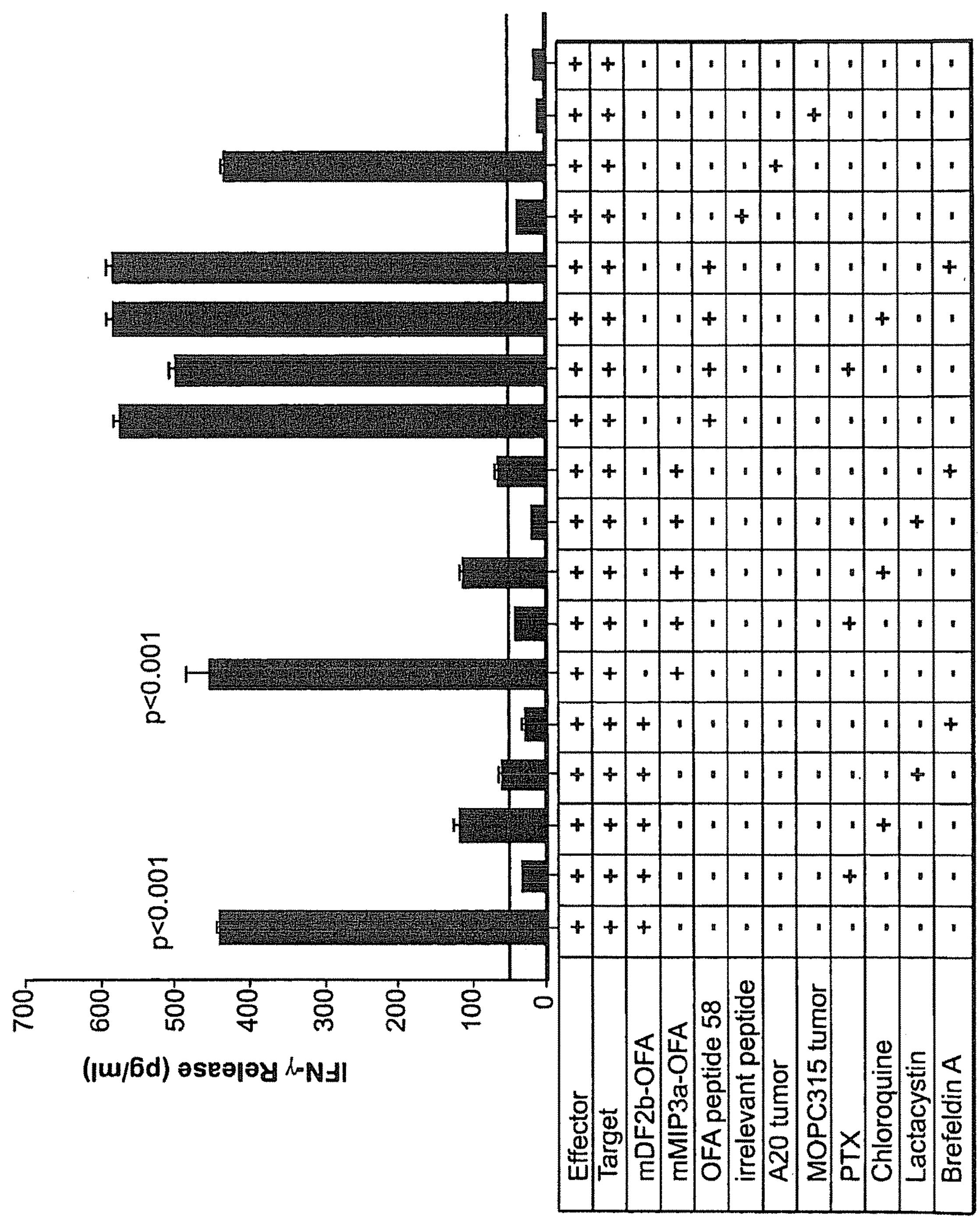
FIGS. 3A-C. (A) Chemoattractants facilitate the CCR6-mediated uptake, processing and presentation of OFA to MHC Class I molecules. Naïve BALB/C mouse iDCs (target cells) were incubated overnight with 100 ng/ml MIP3α-OFA or mDF2β-OFA. Then, after extensive washings and irradiation, they were co-cultured with immune effector splenocytes from BALB/C mice (immunized with the $iLR_{58-66}$ peptide/IFA) and IFN-γ release was measured after overnight incubation. Effector cell specificity was validated using splenocytes pulsed with 1 μg/ml of the $iLR_{58-66}$ (OFA peptide) or MOPC315 peptides (irrelevant peptide); or incubating with $OFA^{+}$ A20 lymphoma or $OFA^{-}$ MOPC315 tumor cells. Control DCs treated with MIP3α fused with an irrelevant tumor antigen or MC148-D-mOFA (data not shown) or mixture of untreated effector cells with splenocytes (E+T) failed to stimulate T cells. Some iDC were also treated in presence of 0.4 M sucrose, or pertussis toxin (PTX), or chloroquine, or brefeldin A, or lactacystin. P-values refer to comparisons after treatment with chlroquine. (B) Co-localization study. To enable internalization, the pre-chilled on ice cells were placed at 37° C. for the time indicated by the column headings. Green, MIP3α-fusions stained with anti-myc mAb 1.9 μg/mL and goat anti-mouse Alexa 488 2 μg/mL. Red fluorophore, Alexa 568 conjugated to goat anti-rabbit IgG, specific for either clathrin (top raw), LAMP (middle row) and proteasomes (bottom row). Merged signal is yellow. Transmission light image is of the 0 min time cell. Scale bar is 5 μm (white rectangle). (C) Processed OFA is presented on MHC class I molecules. iDCs were incubated with mDF2β-OFA or MIP3α-OFA in presence of neutralizing anti-MHC class I ($H-2^{d}$) or isotype-matched control antibodies. Same treatment was performed for control iDCs incubated with 1 μg/ml the OFA or MOPC315 peptides. P-values refer to comparisons with control Abs. Shown, representative data of at least two (C) and three (A and B) independent experiments yielding similar results.
Figure 3B:
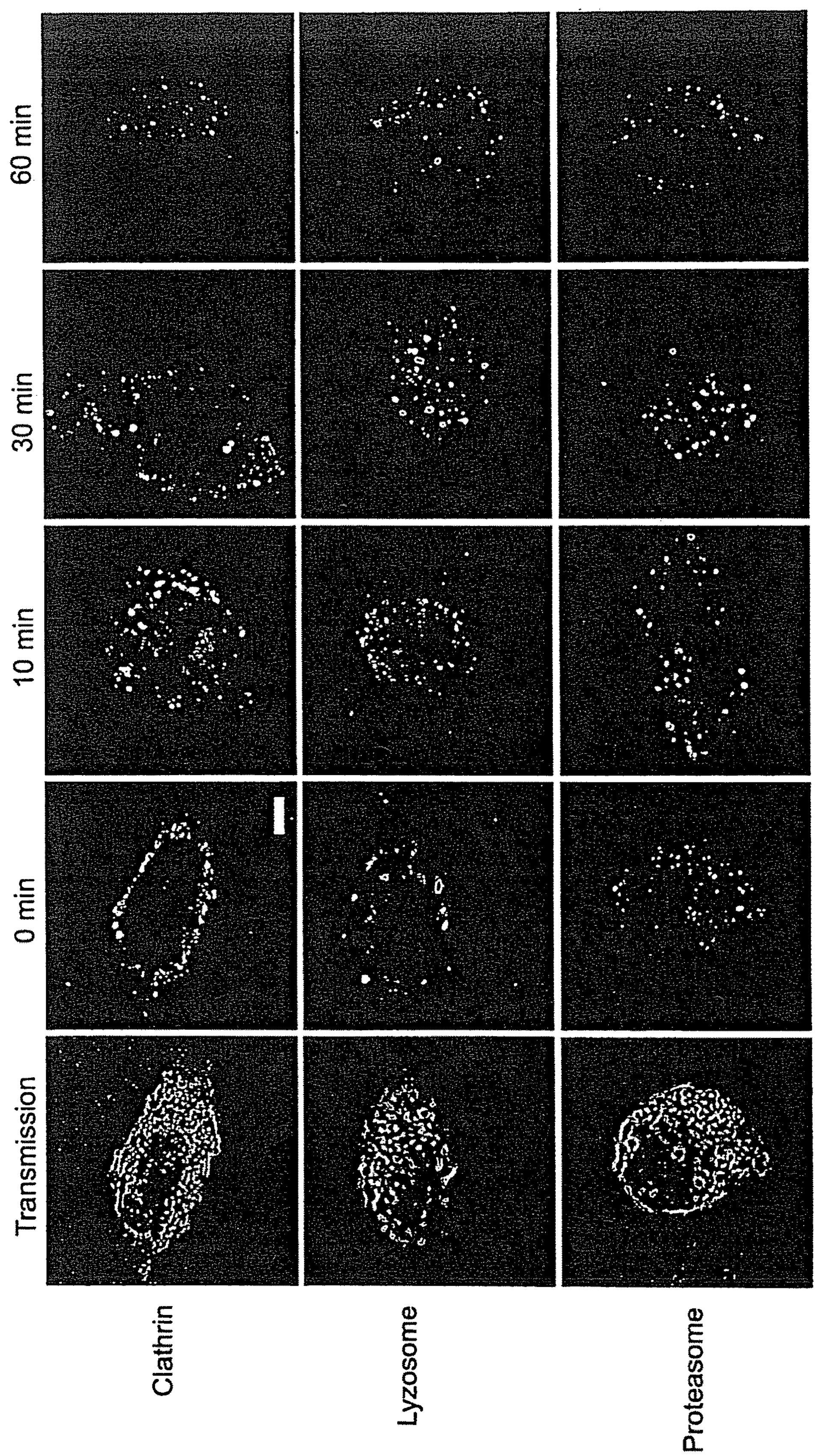
Figure 3C:
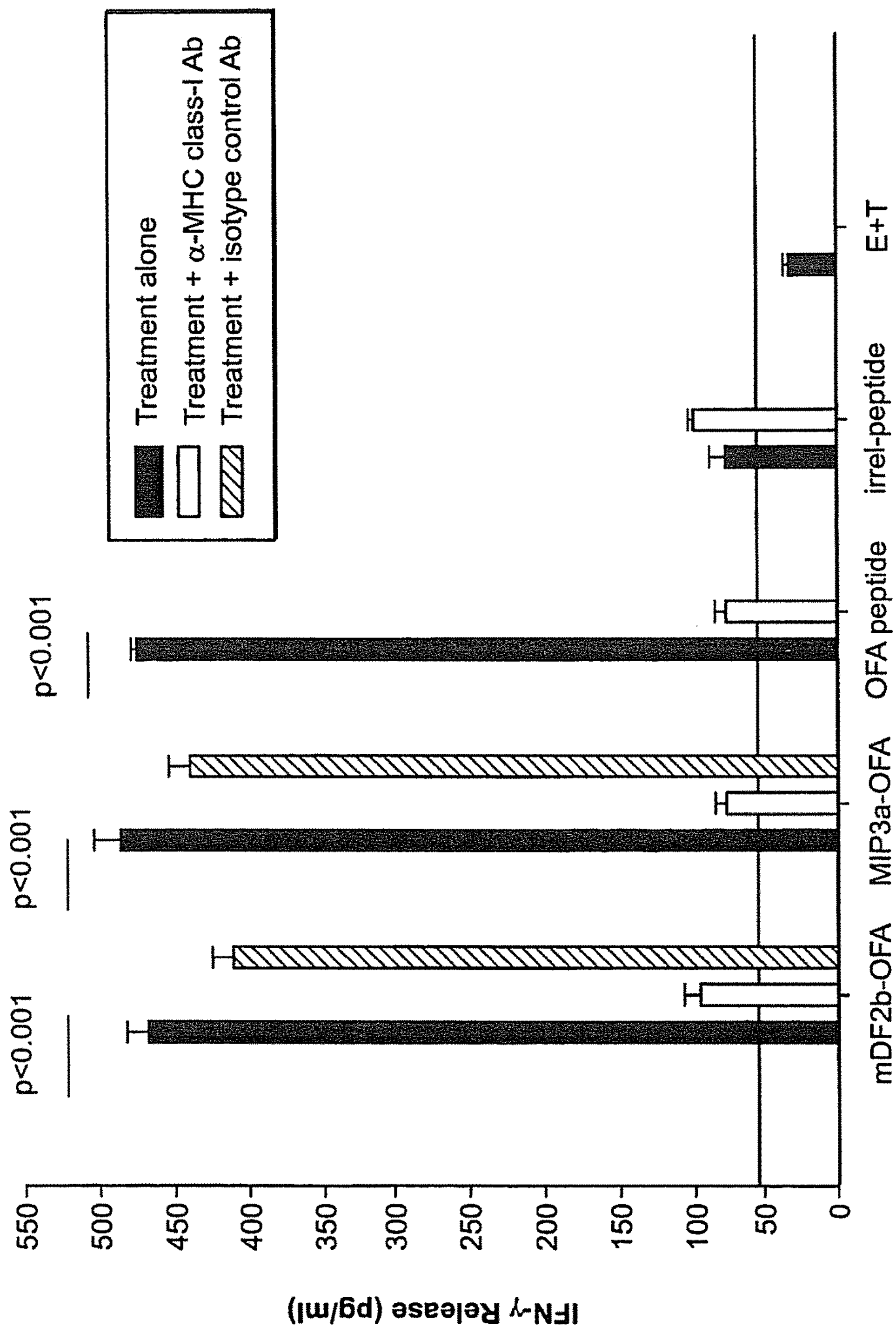

The CCR6-targeted OFA is efficiently taken up and cross-presented to MHC class I molecules. CCR6 would efficiently internalize upon binding with its ligands MIP3α or mDF2β[9]. Similarly, unlike control OFA constructs (OFA alone or fused with mutant chemokines), MIP3α-OFA or mDF2β-OFA were taken up through CCR6 expressed on murine BM iDC (data not shown), suggesting that the CTL responses observed might be due cross-presentation of the internalized OFA. To test this, naïve BM iDCs from BALB/C mice were incubated overnight with nM concentrations of purified recombinant MIP3α-OFA or mDF2β-OFA proteins. Then, after extensive washing and irradiation steps, the cells were mixed with immune splenocytes from syngeneic mice immunized with the peptide OFA-$iLRP_{58-66}$ in IFA, which elicited CTLs capable of specific killing of A20 lymphoma cells in vitro, but not control HLA-matched MOPC315 cells that did not express OFA (FIG. 2*a*). The assumption was that, if CCR6 mediated cross-presentation, APCs incubated with MIP3α-OFA or mDF2β-OFA, but not free OFA, would stimulate the OFA-$iLRP_{58-66}$ peptide-specific T cells. As shown in FIG. 3*a*, only iDCs incubated with as little as 100 ng/ml MIP3α- or mDF2β-OFA fusion proteins induced significant IFNγ secretion from the OFA peptide-specific T cells, suggesting that chemoattractant fused OFA was processed and presented to MHC class I molecules. Control DCs incubated with MIP3α-OFA or mDF2βsFv20 (irrelevant tumor antigen fusions, data not shown) did not stimulate the splenocytes, ruling out non-specific effects from the chemoattractants used. Thus, these data indicate that MIP3α-OFA was efficiently cross-presented, which involved an active receptor-mediated process, as pertussis toxin (PTX, which abrogates Giα-coupled receptor signaling, FIG. 3*a*), or high hypertonic sucrose solution (which inhibits clathrin-coated pit dependent endocytosis, data not shown) completely abolished ability of APCs to stimulate T cells. Similarly, chloroquine, the serine and cysteine protease inhibitor of lysosomal protein degradation, or brefeldin A, a fungal metabolite that inhibits vesicle transport of newly synthesized MHC class molecules between the endoplasmic reticulum (ER) and Golgi[20], completely abrogated the response (FIG. 3*a*), indicating the importance of lysosomal activity in the chemoattractant-induced MHC class I presentation of OFA. Proteins were shown to be processed directly within endosomal/lysosomal compartments and loaded to MHC class I molecules, which resided in classical MHC class II compartments, utilizing TAP-independent and $NH_4Cl$-sensitive cross-presentation pathways[21,22]. However, the CCR6-targeted OFA utilized classical cross-presentation pathway in the cytosol, since lactacystin, a specific inhibitor of proteasomal protein degradation, completely abrogated the response (FIG. 3*a*). The pharmacological inhibitors used in this experiment did not cause non-specific suppressions, since they did not affect stimulation of T cells induced by iDCs that were directly pulsed with OFA-$iLRP_{58-66}$ peptide (that did not require internalization and processing, FIG. 3*a*). These findings are supported by the confocal microscopy studies demonstrating that MIP3α-fusions, prior to internalization, were colocalized with clathrin vesicles on the cell surface (0 min, FIG. 3*b*). However, within 10 min after internalization of MIP3α-fusions, they were found in lyzosomes or colocalized with proteasomes in the cytosol (FIG. 3*b*). The processed MIP3α-fusions were presumably degraded within 1 hour after the internalization by lyzosomal enzymes and proteasomes (since the colocalized signal disappeared by 60 min incubation, FIG. 3*b*). Presumably, 60 min is sufficient to present processed peptides to MHC molecules, since iDCs incubated with MIP3α-OFA for as little as one hour were capable of stimulating immune T cells (though at much lower levels, data not shown). The peptides were presented onto $H\text{-}2^d$ molecules, as the blocking antibody, but not control isotype matched antibody, completely abolished ability of iDCs incubated with MIP3α-OFA or mDF2β-OFA to stimulate immune T cells (FIG. 3*c*). Taken together, these data clearly demonstrate that potency of MIP3α-OFA or mDF2β-OFA is in their ability to use the CCR6-mediated uptake, processing and cross-presentation pathways. As a result, the vaccine elicited both $CD4^+$ T helper, as recently reported[10], and cytolytic $CD8^+$ T cell responses leading to protection from A20 lymphoma, known for its resistance to immunotherapy[23;24]. Thus, it is tempting to speculate that lack of tumor protection in mice immunized with OFA-$iLRP_{58-66}$ peptide/IFA (data not shown) might be attributed to the absence of the T helper responses, although they generated CTLs capable of killing of A20 tumor cells in vitro (FIG. 2*a*).

Conclusion. The superiority of the CCR6-targeting OFA vaccines are in their ability to elicit not only $CD8^+$ CTLs (that recognized multiple OFA epitopes), but also in induction of Th1 helper $CD4^+$ T cell responses.

Since this otherwise non-immunogenic OFA-iLRP is not expressed in normal adult tissues, the vaccine formulation can be also utilized as a preventive vaccine for induction of protective antitumor memory responses in healthy people at high risk for cancer.

Moreover, the vaccines of the invention have been shown to cause long lasting protective responses in mice.

Incorporation by Reference

The contents of all references, patents, pending patent applications and published patents, cited throughout this application are hereby expressly incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

The following documents are referred to above and generally specified by superscript number corresponding to the reference number set forth below. Thus, for example, the first document of Cogin et al. *Anticancer Res.* 19:5535-5542 is referred to above with a superscript 1.

1. Coggin, J. H., Jr., A. L. Barsoum, and J. W. Rohrer. 1999. 37 kiloDalton oncofetal antigen protein and immature laminin receptor protein are identical, universal T-cell inducing immunogens on primary rodent and human cancers. *Anticancer Res.* 19:5535-5542.
2. Bendandi, M., C. D. Gocke, C. B. Kobrin, F. A. Benko, L. A. Sternas, R. Pennington, T. M. Watson, C. W. Reynolds, B. L. Gause, P. L. Duffey, E. S. Jaffe, S. P. Creekmore, D. L. Longo, and L. W. Kwak. 1999. Complete molecular remissions induced by patient-specific vaccination plus granulocyte-monocyte colony-stimulating factor against lymphoma. *Nat. Med.* 5:1171-1177.
3. Timmerman, J. M. 2003. Immunotherapy for lymphomas. *Int. J. Hematol.* 77:444-455.
4. Savelyeva, N., C. A. King, E. S. Vitetta, and F. K. Stevenson. 2005. Inhibition of a vaccine-induced antitumor B cell response by soluble protein antigen in the absence of continuing T cell help. *Proc. Natl. Acad. Sci. U.S.A.* 102:10987-10992.
5. Coggin, J. H., Jr., A. L. Barsoum, and J. W. Rohrer. 1998. Tumors express both unique TSTA and crossprotective 44 kDa oncofetal antigen. *Immunol Today.* 19:405-408.
6. Siegel, S., A. Wagner, D. Kabelitz, M. Marget, J. Coggin, Jr., A. Barsoum, J. Rohrer, N. Schmitz, and M. Zeis. 2003. Induction of cytotoxic T-cell responses against the oncofetal antigen-immature laminin receptor for the treatment of hematologic malignancies. *Blood* 102:4416-4423.
7. Siegel, S., A. Wagner, B. Friedrichs, A. Wendeler, L. Wendel, D. Kabelitz, J. Steinmann, A. Barsoum, J. Coggin, J. Rohrer, P. Dreger, N. Schmitz, and M. Zeis. 2006. Identification of HLA-A*0201-presented T cell epitopes derived from the oncofetal antigen-immature laminin receptor protein in patients with hematological malignancies. *J. Immunol.* 176:6935-6944.
8. Biragyn, A., K. Tani, M. C. Grimm, S. D. Weeks, and L. W. Kwak. 1999. Genetic fusion of chemokines to a self tumor antigen induces protective, T-cell dependent antitumor immunity. *Nature Biotechnology* 17:253-258.
9. Biragyn, A., M. Surenhu, D. Yang, P. A. Ruffini, B. A. Haines, E. Klyushnenkova, J. J. Oppenheim, and L. W. Kwak. 2001. Mediators of innate immunity that target immature, but not mature, dendritic cells induce antitumor immunity when genetically fused with nonimmunogenic tumor antigens. *J. Immunol.* 167:6644-6653.
10. Biragyn, A., P. A. Ruffini, M. Coscia, L. K. Harvey, S. S. Neelapu, S. Baskar, J. M. Wang, and L. W. Kwak. 2004. Chemokine receptor-mediated delivery directs self-tumor antigen efficiently into the class II processing pathway in vitro and induces protective immunity in vivo. *Blood* 104:1961-1969.
11. Schiavo, R., D. Baatar, P. Olkhanud, F. E. Indig, N. Restifo, D. Taub, and A. Biragyn. 2006. Chemokine receptor targeting efficiently directs antigens to MHC class I pathways and elicits antigen-specific CD8+ T-cell responses. *Blood.* 107:4597-4605.
12. Sallusto, F., B. Palermo, D. Lenig, M. Miettinen, S. Matikainen, I. Julkunen, R. Forster, R. Burgstahler, M. Lipp, and A. Lanzavecchia. 1999. Distinct patterns and kinetics of chemokine production regulate dendritic cell function. *Eur. J. Immunol* 29:1617-1625.
13. Dieu, M. C., B. Vanbervliet, A. Vicari, J. M. Bridon, E. Oldham, S. Ait-Yahia, F. Briere, A. Zlotnik, S. Lebecque, and C. Caux. 1998. Selective recruitment of immature and mature dendritic cells by distinct chemokines expressed in different anatomic sites. *J. Exp. Med.* 188:373-386.
14. Hawiger, D., K. Inaba, Y. Dorsett, M. Guo, K. Mahnke, M. Rivera, J. V. Ravetch, R. M. Steinman, and M. C. Nussenzweig. 2001. Dendritic cells induce peripheral T cell unresponsiveness under steady state conditions in vivo. *J. Exp. Med.* 194:769-779.
15. Buchner, J., I. Pastan, and U. Brinkmann. 1992. A method for increasing the yield of properly folded recombinant fusion proteins: single-chain immunotoxins from renaturation of bacterial inclusion bodies. *Anal. Biochem.* 205:263-270.
16. Bogen, B. and J. D. Lambris. 1989. Minimum length of an idiotypic peptide and a model for its binding to a major histocompatibility complex class II molecule. *EMBO J.* 8:1947-1952.
17. Fields, R. C., J. J. Osterholzer, J. A. Fuller, E. K. Thomas, P. J. Geraghty, and J. J. Mule. 1998. Comparative analysis of murine dendritic cells derived from spleen and bone marrow. *J. Immunother.* 21:323-339.
18. Partridge, J. J., J. O. Lopreiato, Jr., M. Latterich, and F. E. Indig. 2003. DNA damage modulates nucleolar interaction of the Werner protein with the AAA ATPase p97/VCP. *Mol. Biol. Cell* 14:4221-4229.
19. Finkelman, F. D., J. Holmes, I. M. Katona, J. F. Urban, Jr., M. P. Beckmann, L. S. Park, K. A. Schooley, R. L. Coffman, T. R. Mosmann, and W. E. Paul. 1990. Lymphokine control of in vivo immunoglobulin isotype selection. *Annu. Rev. Immunol.* 8:303-333.
20. Misumi, Y., Y. Misumi, K. Miki, A. Takatsuki, G. Tamura, and Y. Ikehara. 1986. Novel blockade by brefeldin A of intracellular transport of secretory proteins in cultured rat hepatocytes. *J. Biol. Chem.* 261:11398-11403.
21. Lizee, G., G. Basha, J. Tiong, J. P. Julien, M. Tian, K. E. Biron, and W. A. Jefferies. 2003. Control of dendritic cell cross-presentation by the major histocompatibility complex class I cytoplasmic domain. *Nat. Immunol* 4:1065-1073.
22. Gromme, M., F. G. Uytdehaag, H. Janssen, J. Calafat, R. S. van Binnendijk, M. J. Kenter, A. Tulp, D. Verwoerd, and J. Neefjes. 1999. Recycling MHC class I molecules and endosomal peptide loading. *Proc. Natl. Acad. Sci. U.S.A* 96:10326-10331.
23. Kim, K. J., L. C. Kanellopoulos, R. M. Merwin, D. H. Sachs, and R. Asofsky. 1979. Establishment and characterization of BALB/c lymphoma lines with B cell properties. *J. Immunol.* 122:549-554.
24. Biragyn, A. and L. W. Kwak. 1999. B-cell malignancies as a model for cancer vaccines: from prototype protein to next generation genetic chemokine fusions. *Immunol Rev.* 170:115-126.
25. Antony, P. A., C. A. Piccirillo, A. Akpinarli, S. E. Finkelstein, P. J. Speiss, D. R. Surman, D. C. Palmer, C. C. Chan, C. A. Klebanoff, W. W. Overwijk, S. A. Rosenberg, and N. P. Restifo. 2005. CD8+ T cell immunity against a tumor/self-antigen is augmented by CD4+ T helper cells and hindered by naturally occurring T regulatory cells. *J. Immunol* 174:2591-2601.
26. Ahlers, J. D., I. M. Belyakov, M. Terabe, R. Koka, D. D. Donaldson, E. K. Thomas, and J. A. Berzofsky. 2002. A push-pull approach to maximize vaccine efficacy: abrogating suppression with an IL-13 inhibitor while augmenting help with granulocyte/macrophage colony-stimulating factor and CD40L. *Proc. Natl. Acad. Sci. US.A.* 99:13020-13025.
27. Dunn, G. P., L. J. Old, and R. D. Schreiber. 2004. The immunobiology of cancer immunosurveillance and immunoediting. Immunity. 21:137-148.
28. Biragyn, A., P. A. Ruffini, C. A. Leifer, E. Klyushnenkova, A. Shakhov, O. Chertov, A. K. Shirakawa, J. M. Farber, D. M. Segal, J. J. Oppenheim, and L. W. Kwak. 2002. Toll-like receptor 4-dependent activation of dendritic cells by beta-defensin 2. *Science* 298:1025-1029.
29. Wang, Y., C. G. Kelly, M. Singh, E. G. McGowan, A. S. Carrara, L. A. Bergmeier, and T. Lehner. 2002. Stimulation of Th1-polarizing cytokines, C—C chemokines, maturation of dendritic cells, and adjuvant function by the peptide binding fragment of heat shock protein 70. *J. Immunol.* 169:2422-2429.
30. Wang, Y., C. G. Kelly, J. T. Karttunen, T. Whittall, P. J. Lehner, L. Duncan, P. MacAry, J. S. Younson, M. Singh, W. Oehlmann, G. Cheng, L. Bergmeier, and T. Lehner. 2001. CD40 is a cellular receptor mediating mycobacterial heat shock protein 70 stimulation of CC-chemokines. *Immunity.* 15:971-983.
31. Ruffini, P. A., A. Biragyn, M. Coscia, L. K. Harvey, S. C. Cha, B. Bogen, and L. W. Kwak. 2004. Genetic fusions with viral chemokines target delivery of nonimmunogenic antigen to trigger antitumor immunity independent of chemotaxis. *J. Leukoc. Biol.* 76:77-85.
32. Kaminski, M. S., K. Kitamura, D. G. Maloney, and R. Levy. 1987. Idiotype vaccination against murine B cell lymphoma, inhibition of tumor immunity by free idiotype protein. *J. Immunol* 138:1289-1296.
33. Syrengelas, A. D., Chen, T. T., and Levy, R. 1996. DNA immunization induces protective immunity against B-cell lymphoma. *Nat. Med.* 2:1038-1041.
34. King, C. A., Spellerberg, M. B., Zhu, D., Rice, J., Sahota, S. S., Thompsett, A. R., Hamblin, T. J., Radl, J., and Stevenson, F. K. 1998. DNA vaccines with single-chain Fv fused to fragment C of tetanus toxin induce protective immunity against lymphoma and myeloma. *Nat. Med.* 4:1281-1286.
35. Manetti, C., E. Rouvier, E. Gautherot, E. Loucif, J. Barbet, and J. M. Le Doussal. 1997. Targeting BCL1 lymphoma with anti-idiotype antibodies: biodistribution kinetics of directly labeled antibodies and bispecific antibody-targeted bivalent haptens. *Int. J. Cancer* 71:1000-1009.
36. Ruffini, P. A., S. S. Neelapu, L. W. Kwak, and A. Biragyn. 2002. Idiotypic vaccination for B-cell malignancies as a model for therapeutic cancer vaccines: from prototype protein to second generation vaccines. *Haematologica* 989-1001.
37. Stevenson, F. K., Zhu, D., King, C. A., Ashworth, L. J., Kumar, S., and Hawkins, R. E. 1995. Idiotypic DNA vaccines against B-cell lymphoma. *Immunol. Rev.* 145: 211-228.
38. Rohrer, J. W., A. L. Barsoum, and J. H. Coggin, Jr. 2006. Identification of oncofetal antigen/immature laminin receptor protein epitopes that activate BALB/c mouse OFA/iLRP-specific effector and regulatory T cell clones. *J. Immunol.* 176:2844-2856.

What is claimed is:

1. A polypeptide comprising a tumor-associated embryonic antigen translationally fused with a CCR6-targeting chemoattractant ligand, wherein the tumor-associated embryonic antigen is OFA-iLRP, and the chemoattractant ligand is β-defensin DF2β, wherein the polypeptide comprises the amino acid sequence of SEQ ID Nos: 2 or 20.

2. A polypeptide comprising a tumor-associated embryonic antigen translationally fused with a chemoattractant ligand, wherein the tumor-associated embryonic antigen is OFA-iLRP and the chemoattractant ligand is MIP3α/CCL20, wherein the polypeptide comprises the amino acid sequence of SEQ ID NOs: 4, 12, 18, 22, 24, or 30.

3. The polypeptide of claim 1, further comprising a polypeptide linker between the tumor-associated embryonic antigen and the chemoattractant ligand.

4. A cancer vaccine comprising the polypeptide of claim 1.

5. A kit comprising the vaccine of claim 4 and instructions for use.

* * * * *